(12) United States Patent
Lee et al.

(10) Patent No.: US 10,233,212 B2
(45) Date of Patent: Mar. 19, 2019

(54) COMPOUNDS, LINKER-DRUGS AND LIGAND-DRUG CONJUGATES

(71) Applicant: Industrial Technology Research Institute, Hsinchu (TW)

(72) Inventors: On Lee, Hsinchu (TW); Mei-Hsuan Tsai, Nantou (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 15/341,117

(22) Filed: Nov. 2, 2016

(65) Prior Publication Data

US 2018/0016300 A1    Jan. 18, 2018

Related U.S. Application Data

(60) Provisional application No. 62/250,107, filed on Nov. 3, 2015.

(51) Int. Cl.

| | | |
|---|---|---|
| *A01N 43/40* | (2006.01) | |
| *A61K 31/44* | (2006.01) | |
| *C07K 7/02* | (2006.01) | |
| *A61K 47/68* | (2017.01) | |
| *C07K 5/02* | (2006.01) | |
| *A61K 47/55* | (2017.01) | |

(52) U.S. Cl.
CPC .............. *C07K 7/02* (2013.01); *A61K 47/551* (2017.08); *A61K 47/6817* (2017.08); *A61K 47/6889* (2017.08); *C07K 5/0207* (2013.01)

(58) Field of Classification Search
CPC   A61K 47/6889; A61K 47/6811; A61K 47/65; A61K 38/00; A61K 47/64; A61K 51/088
See application file for complete search history.

(56) References Cited

U.S. PATENT DOCUMENTS

| | | | |
|---|---|---|---|
| 7,091,186 B2 | 8/2006 | Senter et al. | |
| 7,659,241 B2 | 2/2010 | Senter et al. | |
| 7,989,434 B2 | 8/2011 | Feng | |
| 8,034,959 B2 | 10/2011 | Ng et al. | |
| 8,288,352 B2 | 10/2012 | Doronina et al. | |
| 8,343,928 B2 | 1/2013 | Doronina et al. | |
| 8,470,980 B2 | 6/2013 | Hutchinson et al. | |
| 8,609,105 B2 | 12/2013 | Senter et al. | |
| 8,703,714 B2 | 4/2014 | Doronina et al. | |
| 8,871,720 B2 | 10/2014 | Doronina et al. | |
| 8,877,706 B2 | 11/2014 | Li et al. | |
| 8,889,855 B2 | 11/2014 | Deng | |
| 8,906,376 B2 | 12/2014 | Senter et al. | |
| 9,062,094 B2 | 6/2015 | Rau et al. | |
| 2009/0318668 A1 | 12/2009 | Beusker et al. | |
| 2010/0062008 A1 | 3/2010 | Senter et al. | |
| 2011/0020343 A1 | 1/2011 | Senter et al. | |
| 2011/0027274 A1 | 2/2011 | Cheng et al. | |
| 2012/0107332 A1 | 5/2012 | Jeffrey | |
| 2012/0225089 A1 | 9/2012 | Bouchard et al. | |
| 2015/0017246 A1 | 1/2015 | Huang | |
| 2015/0044238 A1 | 2/2015 | Doronina et al. | |
| 2015/0110815 A1 | 4/2015 | Park et al. | |
| 2015/0165063 A1 | 6/2015 | Flygare et al. | |
| 2015/0299337 A1 | 10/2015 | Ochiai et al. | |
| 2016/0130356 A1 | 5/2016 | DeSander et al. | |

FOREIGN PATENT DOCUMENTS

| | | |
|---|---|---|
| CN | 101980725 A | 2/2011 |
| CN | 101573384 A | 2/2013 |
| CN | 102973947 A | 3/2013 |
| CN | 101490087 A | 11/2013 |
| JP | 6-293795 A | 10/1994 |
| JP | 7-188285 A | 7/1995 |
| JP | 2006-500333 A | 1/2006 |
| JP | 2009-501800 A | 1/2009 |

(Continued)

OTHER PUBLICATIONS

Vippagunta et al., "Crystalline Solids", Advanced Drug Delivery Reviews, vol. 48, pp. 3-26, 2001. (Year: 2001).*
Gavezzotti, "Are Crystal Structures Predictable?", Accounts of Chemical Research, vol. 27, pp. 309-314, 1994. (Year: 1994).*
European Search Report for Appl. No. 16196894.6 dated Mar. 17, 2017.
European Search Report for Appl. No. 16196894.6 dated May 16, 2017.
Doronina et al., "Development of potent monoclonal antibody auristatin conjugates for cancer therapy", Nature Biotechnology, vol. 21, No. 7 Jul. 2003, pp. 778-784 (8 pages total), with a correction to the article (from Nature Biotechnology, vol. 21, No. 8, Aug. 2003, p. 941).

(Continued)

*Primary Examiner* — Rachael E Bredefeld
*Assistant Examiner* — Kaipeen E Yang
(74) *Attorney, Agent, or Firm* — Birch, Stewart, Kolasch & Birch, LLP

(57) ABSTRACT

A compound of formula (I) or a pharmaceutically acceptable salt or solvate thereof is provided. In formula (I), R1, R2 and R3 are each, independently, hydrogen, amino, nitro, halogen, hydroxyl, C1-C6 alkoxy, carboxylic acid, C1-C6 alkoxycarbonyl, C1-C6 amino, C1-C6 aminocarbonyl, C1-C6 alkyl, branched C1-C6 alkyl, C1-C6 cycloalkyl, C1-C6 heterocyclic, aryl or heteroaryl, provided at least one of R1 and R3 is an amino group. A linker-drug and a ligand-drug conjugate including the compound are also provided.

(I)

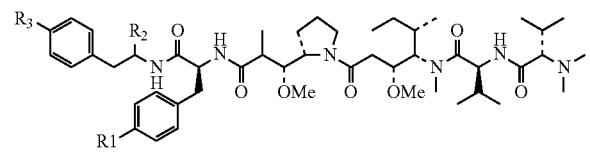

12 Claims, 2 Drawing Sheets

(56) References Cited

FOREIGN PATENT DOCUMENTS

| | | |
|---|---|---|
| JP | 2014-521319 A | 8/2014 |
| JP | 2015-505850 A | 2/2015 |
| TW | 201515662 A | 5/2015 |
| TW | 201605481 A | 2/2016 |
| WO | WO 90/14844 A2 | 12/1990 |
| WO | WO 91/13904 A1 | 9/1991 |
| WO | WO 95/09864 A1 | 4/1995 |
| WO | WO 2004/010957 A2 | 2/2004 |
| WO | WO 2005/082023 A2 | 9/2005 |
| WO | WO 2005/112919 A2 | 12/2005 |
| WO | WO 2006/060533 A2 | 6/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/089149 A2 | 8/2007 |
| WO | WO 2008/034124 A2 | 3/2008 |
| WO | WO 2008/083312 A2 | 7/2008 |
| WO | WO 2008/103693 A2 | 8/2008 |
| WO | WO 2009/017394 A1 | 2/2009 |
| WO | WO 2009/099741 A1 | 8/2009 |
| WO | WO 2010/009124 A2 | 1/2010 |
| WO | WO 2010/062171 A2 | 6/2010 |
| WO | WO 2011/130598 A1 | 10/2011 |
| WO | WO 2011/133039 A2 | 10/2011 |
| WO | WO 2012/113847 A1 | 8/2012 |
| WO | WO 2012/166560 A1 | 12/2012 |
| WO | WO 2013/055990 A1 | 4/2013 |
| WO | WO 2013/068874 A1 | 5/2013 |
| WO | WO 2013/072813 A2 | 5/2013 |
| WO | WO 2013/122823 A1 | 8/2013 |
| WO | WO 2013/149946 A1 | 10/2013 |
| WO | WO 2013/149948 A1 | 10/2013 |
| WO | WO 2013/166155 A1 | 11/2013 |
| WO | WO 2013/173391 A1 | 11/2013 |
| WO | WO 2013/181597 A2 | 12/2013 |
| WO | WO 2013/185117 A1 | 12/2013 |
| WO | WO 2013/190292 A2 | 12/2013 |
| WO | WO 2013/192360 A1 | 12/2013 |
| WO | WO 2014/008375 A1 | 1/2014 |
| WO | WO 2014/064423 A1 | 5/2014 |
| WO | WO 2014/065661 A1 | 5/2014 |
| WO | WO 2014/067960 A2 | 5/2014 |
| WO | WO 2014/068443 A1 | 5/2014 |
| WO | WO 2014/072482 A1 | 5/2014 |
| WO | WO 2014/080251 A1 | 5/2014 |
| WO | WO 2014/088432 A1 | 6/2014 |
| WO | WO 2014/093379 A1 | 6/2014 |
| WO | WO 2014/094353 A1 | 6/2014 |
| WO | WO 2014/094354 A1 | 6/2014 |
| WO | WO 2014/100762 A1 | 6/2014 |
| WO | WO 2015/054659 A1 | 4/2015 |
| WO | WO 2015/123679 A1 | 8/2015 |

OTHER PUBLICATIONS

Doronina et al., "Novel Peptide Linkers for Highly Potent Antibody-Auristatin Conjugate," Bioconjugate Chemistry, vol. 19, No. 10, 2008 (published online Sep. 20, 2008), pp. 1960-1963.
European Search Report for Appl. No. 16196898.7 dated Mar. 23, 2017.
Sun et al., "Reduction-Alkylation Strategies for the Modification of Specific Monoclonal Antibody Disulfides", Bioconjugate Chemistry, vol. 16, No. 5, 2005, pp. 1282-1290 (22 pages total).
Taiwanese Office Action and Search Report issued in Taiwanese Application No. 105135454 dated Aug. 9, 2017.
Industrial Technology Research Institute, "Smart Target Drug Delivery Technology and Application Development Project" (Year 103, December), Jan. 2015, [retrieved on Nov. 1, 2017], Retrieved from the Internet.
Office Action of JP Application No. 2016-214926 dated Dec. 14, 2017.
Office Action of JP Application No. 2016-215442 dated Dec. 20, 2017.
Japanese Office Action dated Sep. 5, 2018 for JP 2016-214926.
McCombs, J.R., et al, "Antibody Drug Conjugates: Design and Selection of Linker, Payload and Conjugation Chemistry," The AAPS Journal, Mar. 2015, vol. 17, No. 2, pp. 339-351.
Taiwanese Office Action for Appl. No. 105135455 dated Feb. 6, 2018.
Badescu et al., "Bridging Disulfides for Stable and Defined Antibody Drug Conjugates," Bioconjugate Chemistry, vol. 25, May 3, 2014, pp. 1124-1136.
Dubowchik et al., "Cathepsin B-Sensitive Dipeptide Prodrugs. 1. A Model Study of Structural Requirements for Efficient Release of Doxorubicin," Bioorganic & Medicinal Chemistry Letters, vol. 8, 1998, pp. 3341-3346.
Jeffrey et al., "Design, Synthesis, and in Vitro Evaluation of Dipeptide-Based Antibody Minor Groove Binder Conjugates," Journal of Medical Chemistry, vol. 48, No. 5, 2005 (Published on Web Feb. 5, 2005), pp. 1344-1358.
Jeffrey et al., "Dipeptide-based highly potent doxorubicin antibody conjugates," Bioorganic & Medicinal Chemistry Letters, vol. 16, 2006 (available online Nov. 3, 2005), pp. 358-362.
Liang et al., "Novel cathepsin B-sensitive paclitaxel conjugate: Higher water solubility, better efficacy and lower toxicity," Journal of Controlled Release, vol. 160, 2012 (available online Mar. 3, 2012), pp. 618-629.
Toki et al., "Protease-Mediated Fragmentation of p-Amidobenzyl Ethers: A New Strategy for the Activation of Anticancer Prodrugs," Journal of Organic Chemistry, vol. 67, No. 6, 2002 (Published on Web Feb. 12, 2002), pp. 1866-1872.
Verma et al., "The cryptophycins as potent payloads for antibody drug conjugates," Bioorganic & Medicinal Chemistry Letters, vol. 25, 2015 (available online Jan. 2, 2015), pp. 864-868.

* cited by examiner

COMPOUNDS, LINKER-DRUGS AND LIGAND-DRUG CONJUGATES

CROSS REFERENCE TO RELATED APPLICATIONS

This application claims the benefit of U.S. Provisional Application No. 62/250,107, filed Nov. 3, 2015, the entirety of which is incorporated by reference herein.

TECHNICAL FIELD

The technical field relates to an auristatine derivative, a novel linker, a linker-drug and a ligand-drug conjugate including the auristatine derivative.

BACKGROUND

Antibodies have high-degree identification abilities with respect to their corresponding antigens, and many cytotoxic drug molecules cannot be used for cancer therapy because they cannot selectively kill cancer cells. Therefore, the connection of antibodies and highly toxic drugs (such as toxins) becomes a highly selective and specific conjugated drug. The concept of Antibody-Drug Conjugates (ADCs) was proposed more than 30 years ago. The world's major pharmaceutical companies and many small and medium-sized biotechnology companies are investing a lot of money and material resources, or by means of cooperation, to carry out the development of novel ADC drugs.

At present, more than forty ADC drugs have been tested in different phases of clinical trials. Successful use of various ADC drugs in clinical trials has shown that the development of novel ADC drugs is an important task in assisting human beings to meet anti-cancer medical needs.

SUMMARY

One embodiment of the disclosure provides a compound of formula (I) or a pharmaceutically acceptable salt or solvate thereof:

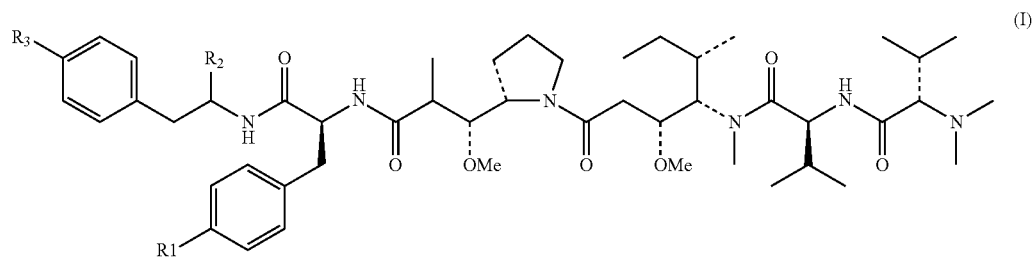

In formula (I), $R_1$, $R_2$ and $R_3$ are each, independently, hydrogen, amino, nitro, halogen, hydroxyl, C1-C6 alkoxy, carboxylic acid, C1-C6 alkoxycarbonyl, C1-C6 amino, C1-C6 aminocarbonyl, normal C1-C6 alkyl, branched C1-C6 alkyl, C1-C6 cycloalkyl, C1-C6 heterocyclic, aryl or heteroaryl, provided at least one of R1 and R3 is an amino group.

One embodiment of the disclosure provides a compound of formula (II) or a pharmaceutically acceptable salt or solvate thereof:

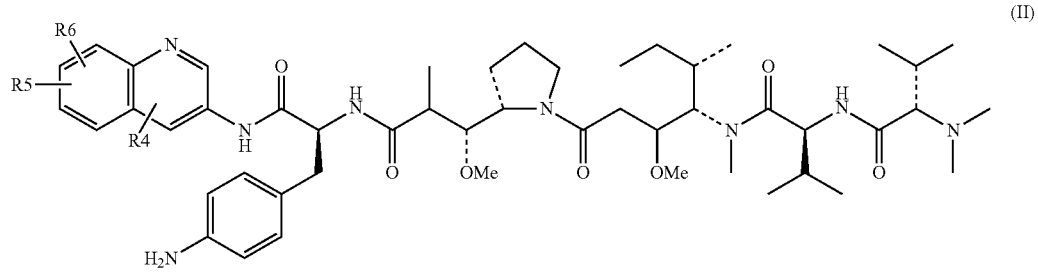

In formula (II), R4, R5 and R6 are each, independently, hydrogen, amino, nitro, halogen, hydroxyl, C1-C6 alkoxy, carboxylic acid, C1-C6 alkoxycarbonyl, C1-C6 amino, C1-C6 aminocarbonyl, normal C1-C6 alkyl, branched C1-C6 alkyl, C1-C6 cycloalkyl, C1-C6 heterocyclic, aryl or heteroaryl.

One embodiment of the disclosure provides a linker-drug of formula (III) or a pharmaceutically acceptable salt or solvate thereof:

C-SAAs-AAs-D      (III)

In formula (III), C- is a conjugating unit selected from the group consisting of

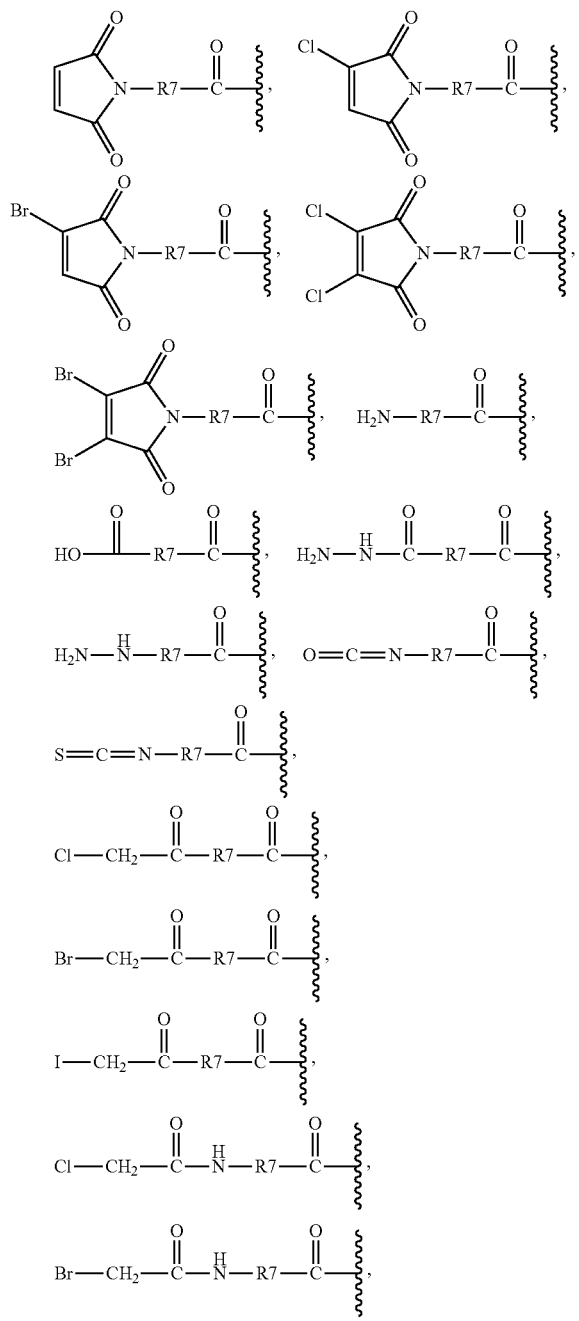

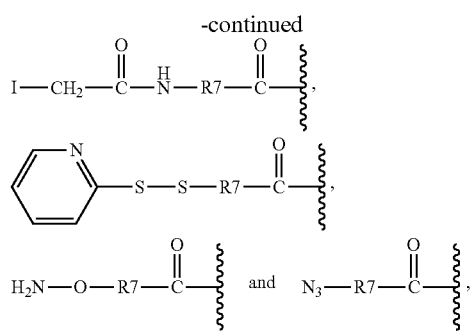

wherein R7 is selected from the group consisting of —C1-C10 alkylene-, —C3-C8 carbocyclo-, —O—(C 1-C8alkyl)-, -arylene-, —C1-C10 alkylene-arylene-, -arylene-C1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, —(C3-C8 heterocyclo)-C1-C10 alkylene-, —(CH$_2$CH$_2$O)$_r$— and —(CH$_2$CH$_2$O)$_r$—CH$_2$—, and r is an integer ranging from 1 to 10.

In formula (III), -SAAs- is a sugar amino acid unit of formula (IV):

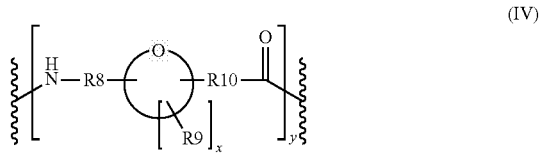

In formula (IV), x is an integer ranging from 1 to 8, y is an integer ranging from 1 to 4,

is a tetrahydrofuran, dihydrofuran, tetrahydropyran or dihydropyran ring, R8 and R10 are each, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 is, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring.

In formula (III), -AAs- is a peptide unit of formula (V):

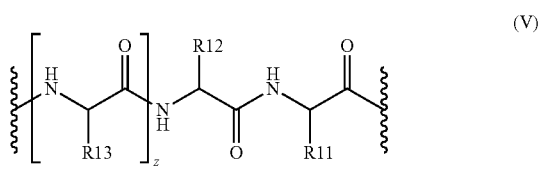

In formula (V), z is an integer ranging from 0 to 10, R11 is —(CH$_2$)$_3$NHC(=NH)NH$_2$, —(CH$_2$)$_3$NH$_2$, —(CH$_2$)$_3$NHCONH$_2$, —(CH$_2$)$_4$NHC(=NH)NH$_2$, —(CH$_2$)$_4$NH$_2$ or —(CH$_2$)$_4$NHCONH$_2$, R12 is H, methyl, ethyl, propyl, isopropyl, cyclopropyl, butyl, sec-butyl, isobutyl, tert-butyl, cyclobutyl, phenyl or benzyl, R13 is hydrogen, methyl, isopropyl, cyclopropyl, butyl, sec-butyl, isobutyl, tert-butyl, cyclobutyl, cyclohexyl, phenyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl, 3-pyridylmethyl or 4-pyridylmethyl.

In formula (III), -D is a cytotoxic agent selected from the group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

One embodiment of the disclosure provides a ligand-drug conjugate of formula (VI) or a pharmaceutically acceptable salt or solvate thereof:

L-(C-SAAs-AAs-D)p     (VI)

In formula (VI), p is an integer ranging from 1 to 20, and L- is a ligand unit selected from the group consisting of full-length antibodies, antibody fragments, proteins, smaller molecular weight proteins, polypeptides, oligopeptides, aptamers, lectins, glycoproteins, lipoproteins, glycolipids, vitamins, nutrient-transport molecules, hormones, monosaccharides, disaccharides, oligosaccharides, polysaccharides and any other cell binding molecules or substance. In this formula, L- is further attached to the disclosed -C-SAAs-AAs-D.

A detailed description is given in the following embodiments with reference to the accompanying drawings.

BRIEF DESCRIPTION OF THE DRAWINGS

The present invention may be more fully understood by reading the subsequent detailed description and examples with references made to the accompanying drawings, wherein.

DETAILED DESCRIPTION

Figure 1:
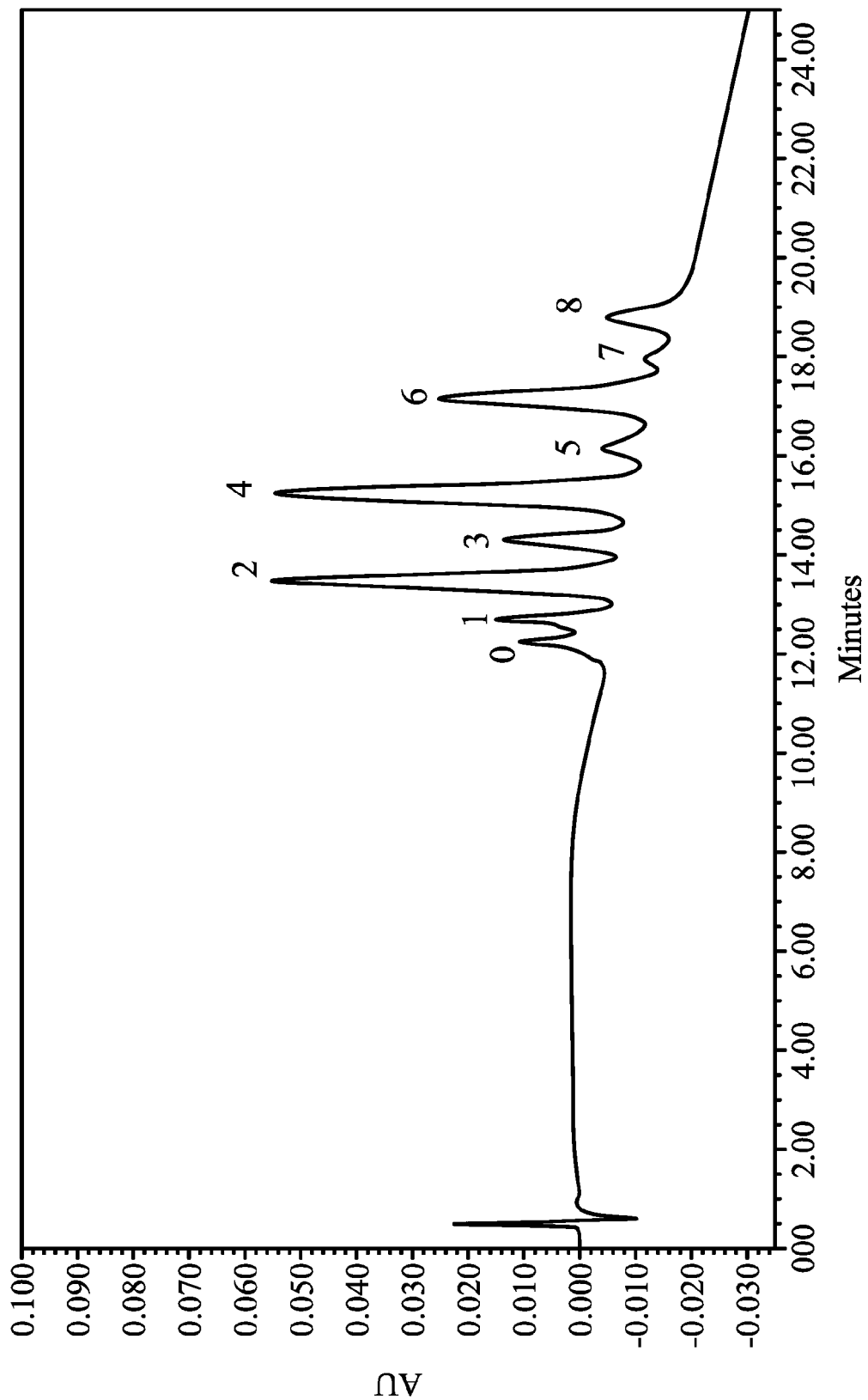
FIG. 1 shows a HIC profile of Erbitux-MC-SAA1-Val-Cit-APEA.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Compounds of the Disclosure

Auristatine Derivatives having an Aniline Moiety

The disclosure provides a novel auristatine derivative, which is characterized as having an aniline moiety to be a linking point for attaching to linkers, ligands or delivery molecules and also potentializes the toxin to have higher anticancer activity against a series of human cancer cell lines. In one embodiment, the auristatine derivative is an aniline moiety-containing compound of formula (I), and a pharmaceutically acceptable salt or solvate thereof is also provided in the disclosure.

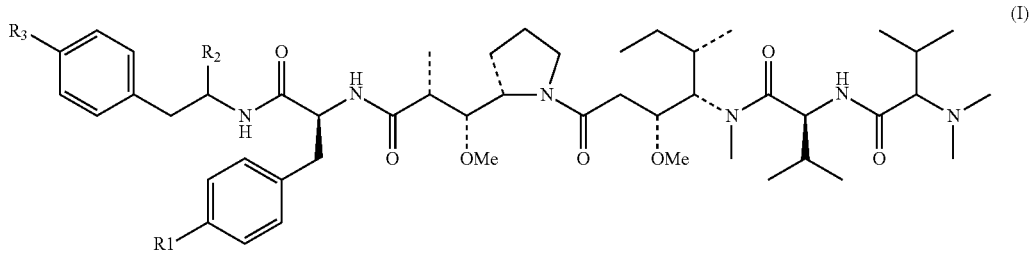

(I)

In formula (I), each of R1, R2 and R3 can be, independently, hydrogen, amino, nitro, halogen, hydroxyl, C1-C6 alkoxy, carboxylic acid, C1-C6 alkoxycarbonyl, C1-C6 amino, C1-C6 aminocarbonyl, normal C1-C6 alkyl, branched C1-C6 alkyl, C1-C6 cycloalkyl, C1-C6 heterocyclic, aryl or heteroaryl, and provided at least one of R1 and R3 is an amino group.

In one embodiment, R1 is hydrogen, R2 is hydrogen, carboxylic acid, C1-C6 alkoxycarbonyl, C1-C6 aminocarbonyl or C1-C6 alkyl, and R3 is amino.

In another embodiment, the auristatine F derivative is an aniline moiety-containing compound of formula (II), and a pharmaceutically acceptable salt or solvate thereof is also provided in the disclosure.

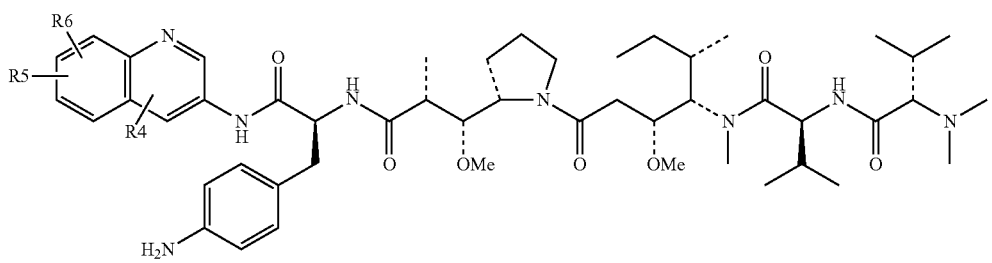

In formula (II), each of R4, R5 and R6 can be, independently, hydrogen, amino, nitro, halogen, hydroxyl, C1-C6 alkoxy, carboxylic acid, C1-C6 alkoxycarbonyl, C1-C6 amino, C1-C6 aminocarbonyl, C1-C6 alkyl, branched C1-C6 alkyl, C1-C6 cycloalkyl, C1-C6 heterocyclic, aryl or heteroaryl.

In one embodiment, R4, R5 and R6 are hydrogen.

Linkers Containing Sugar Amino Acids

The disclosure provides a novel sugar amino acid(s)-containing linker which is characterized as having a cathepsin B recognized dipeptide in its C-terminal and a high hydrophilic sugar amino acid(s) moiety in its N-terminal to improve the aqueous solubility of said linker or linker-containing substance. Both the carboxylic group in the C-terminal and the amino group in the N-terminal of the linker can be a linking point for attaching spacers, linkers, ligands, drugs, toxins, imaging molecules, antibodies, peptides or delivery molecules.

The linker unit of the disclosure comprises a sugar amino acid unit (-SAAs-) and a peptide unit (-AAs-). The peptide unit can be dipeptide, tripeptide, tetrapeptide, pentapeptide, hexapeptide, heptapeptide, octapeptide, nonapeptide, decapeptide, undecapeptide or dodecapeptide.

In one embodiment, the sugar amino acid unit (-SAAs-) is represented by formula (IV):

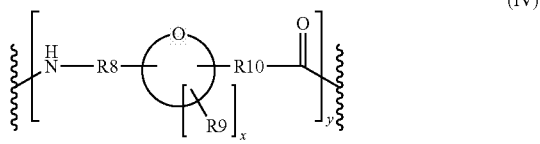

In formula (IV), x is an integer ranging from 1 to 8, y is an integer ranging from 1 to 4,

can be a tetrahydrofuran, dihydrofuran, tetrahydropyran or dihydropyran ring, each of R8 and R10 can be, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 may be, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring.

In the disclosure, examples of said sugar amino acids include but are not limited to:

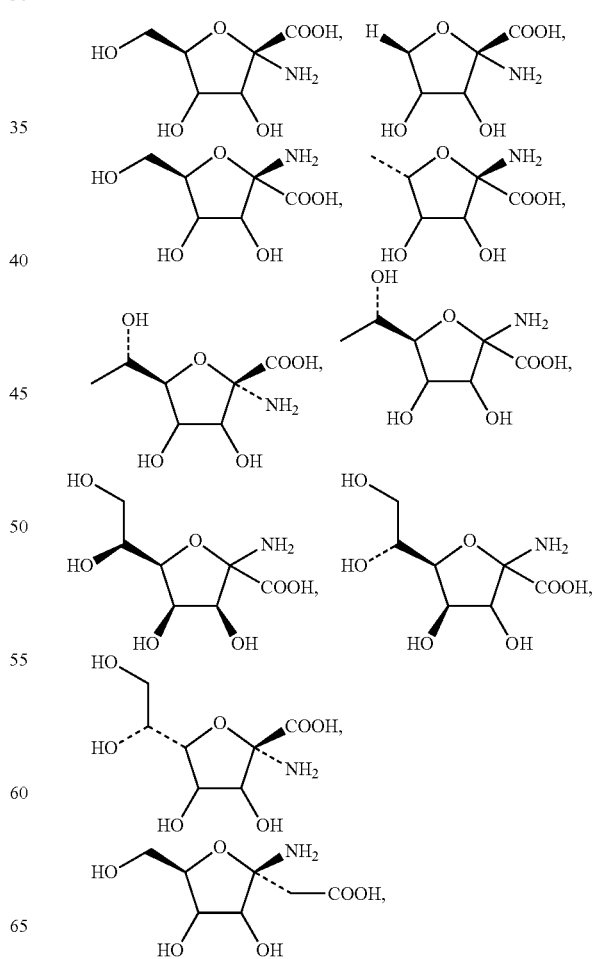

-continued
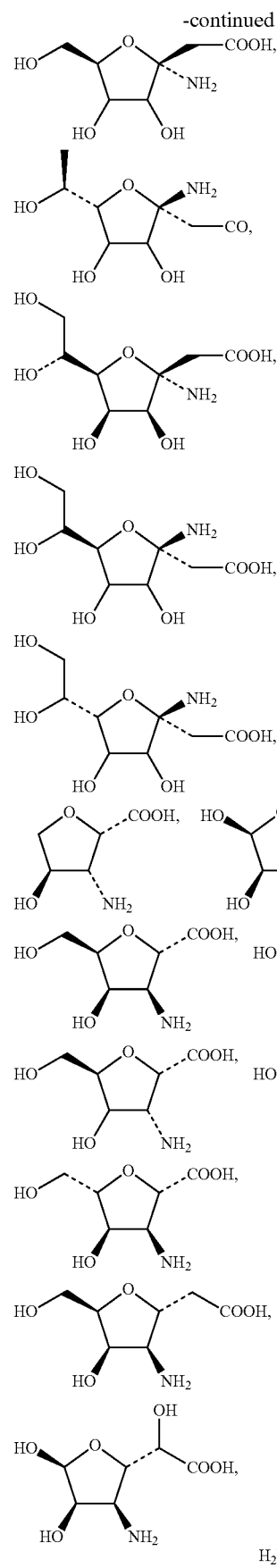
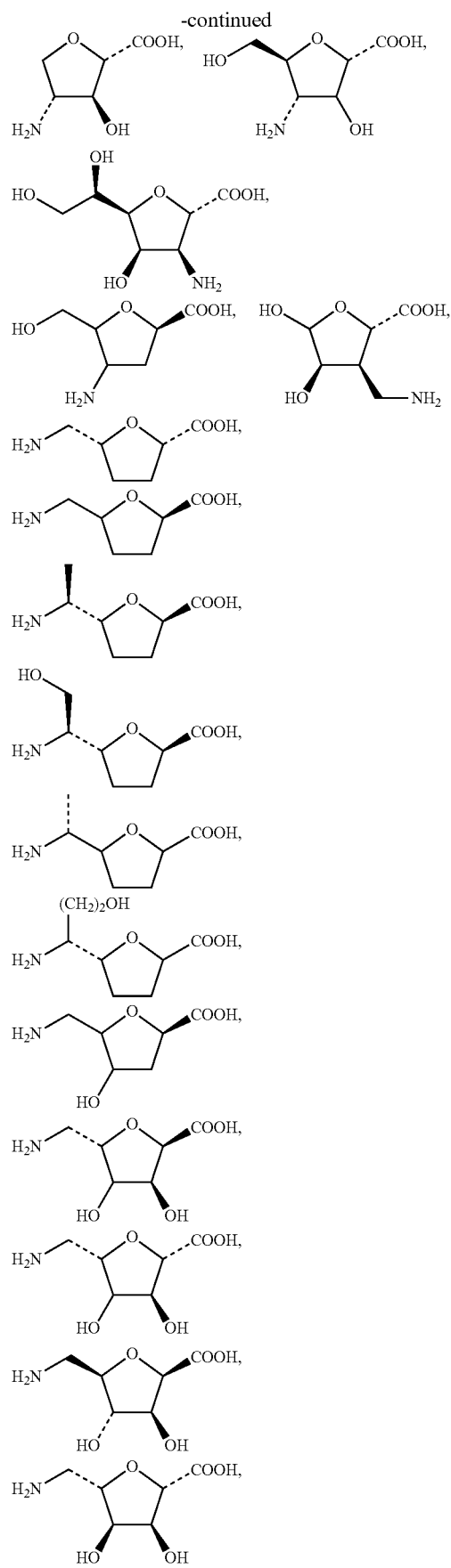

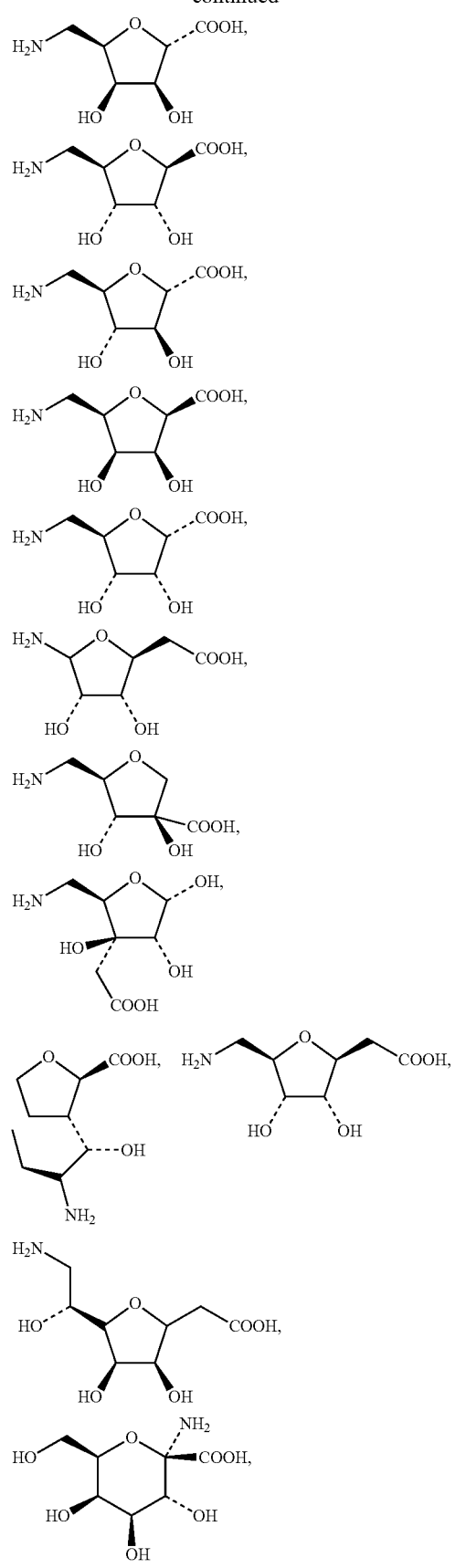
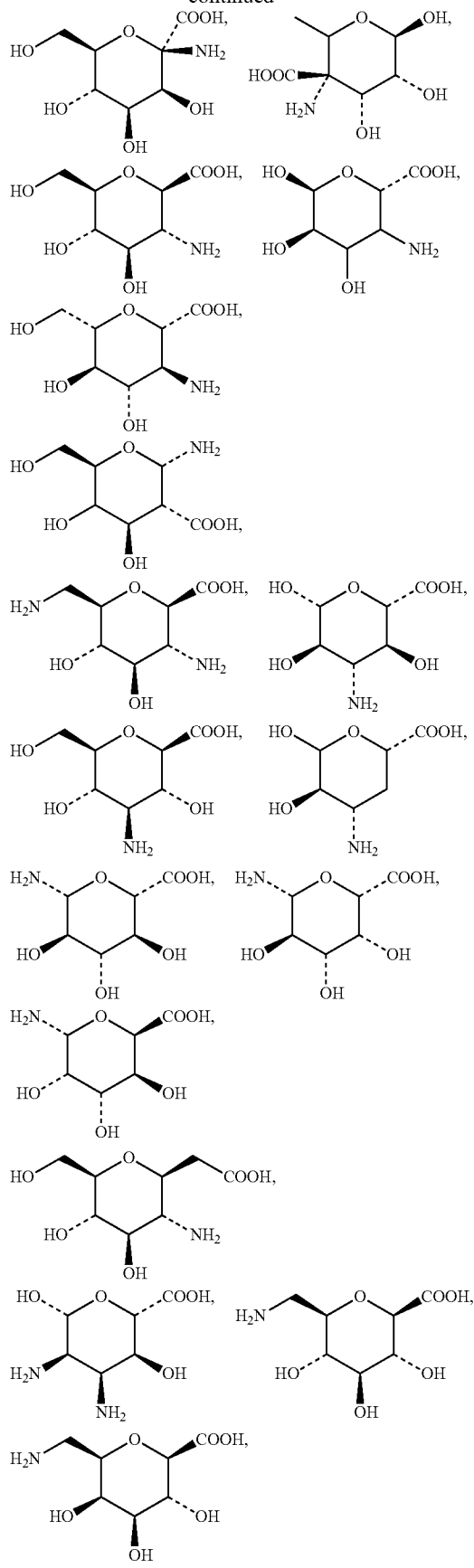

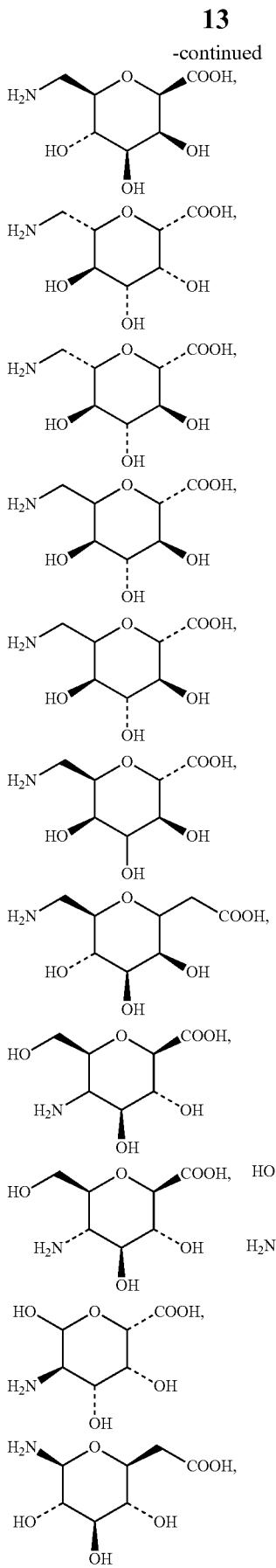

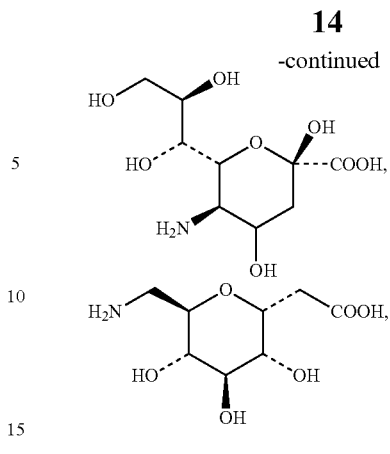

In one embodiment, the peptide unit (-AAs-) is represented by formula (V):

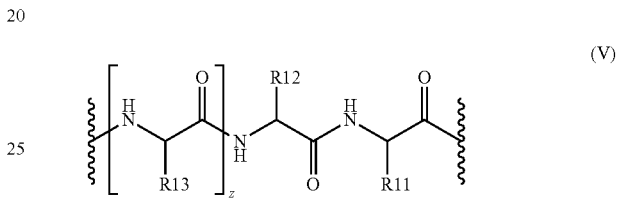

In formula (V), z is an integer ranging from 0 to 10, R11 can be $-(CH_2)_3NHC(=NH)NH_2$, $-(CH_2)_3NH_2$, $-(CH_2)_3$ $NHCONH_2$, $-(CH_2)_4NHC(=NH)NH_2$, $-(CH_2)_4$ $NH_2$ or $-(CH_2)_4NHCONH_2$, R12 can be H, methyl, ethyl, propyl, isopropyl, cyclopropyl, butyl, sec-butyl, isobutyl, tert-butyl, cyclobutyl, phenyl or benzyl, R13 can be hydrogen, methyl, isopropyl, cyclopropyl, butyl, sec-butyl, isobutyl, tert-butyl, cyclobutyl, cyclohexyl, phenyl, benzyl, p-hydroxybenzyl, $-CH_2OH$, $-CH(OH)CH_3$, $-CH_2CH_2SCH_3$, $-CH_2CONH_2$, $-CH_2COOH$, $-CH_2CH_2CONH_2$, $-CH_2CH_2COOH$, $-(CH_2)_3NHC(=NH)NH_2$, $-(CH_2)_3$ $NH_2$, $-(CH_2)_3NHCOCH_3$, $-(CH_2)_3NHCHO$, $-(CH_2)_4$ $NHC(=NH)NH_2$, $-(CH_2)_4$ $NH_2$, $-(CH_2)_4NHCOCH_3$, $-(CH_2)_4NHCHO$, $-(CH_2)_3$ $NHCONH_2$, $-(CH_2)_4$ $NHCONH_2$, $-CH_2CH_2CH(OH)$ $CH_2NH_2$, 2-pyridylmethyl, 3-pyridylmethyl or 4-pyridylmethyl.

The peptide unit can be enzymatically cleaved by one or more enzymes, for example, by a tumor-associated protease to liberate a drug unit (-D).

Linker-drug

One embodiment of the disclosure provides a linker-drug of formula (III) or a pharmaceutically acceptable salt or solvate thereof:

C-SAAs-AAs-D (III)

In formula (III), C- is a conjugating unit selected from the group consisting of

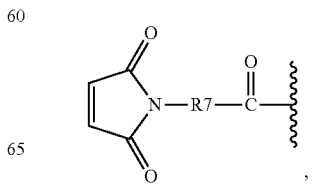

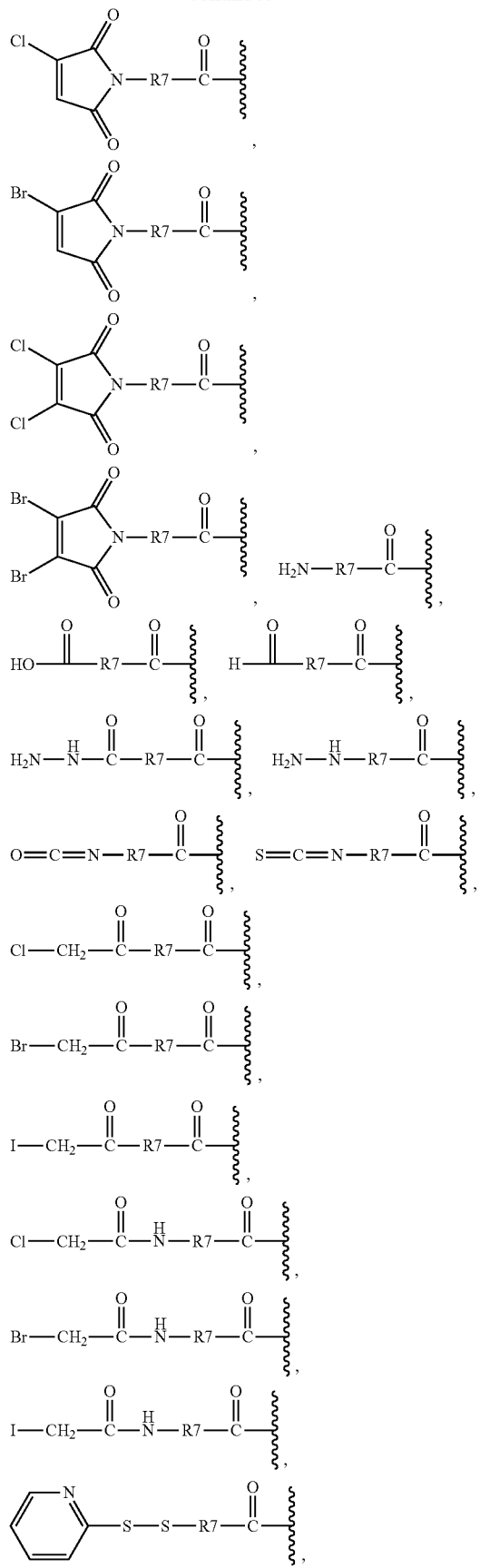

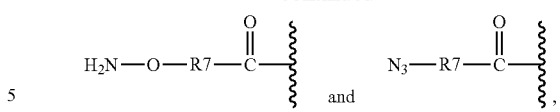

wherein R7 is selected from the group consisting of —C1-C10 alkylene-, —C3-C8 carbocyclo-, —O—(C1-C8 alkyl)-, -arylene-, —C1-C10 alkylene-arylene-, -arylene-C 1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, —(C3-C8 heterocyclo)-C1-C10 alkylene-,—(CH$_2$CH$_2$O)$_r$— and —(CH$_2$CH$_2$O)$_r$—CH$_2$—, and r is an integer ranging from 1 to 10.

In formula (III), -SAAs- is a sugar amino acid unit of formula (IV):

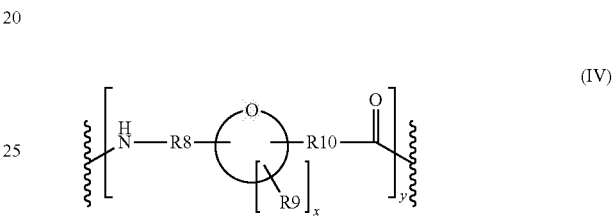

(IV)

In formula (IV), x is an integer ranging from 1 to 8, y is an integer ranging from 1 to 4,

can be a tetrahydrofuran, dihydrofuran, tetrahydropyran or dihydropyran ring, each of R8 and R10 can be, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 may be, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring.

In formula (III), -AAs- is a peptide unit of formula (V):

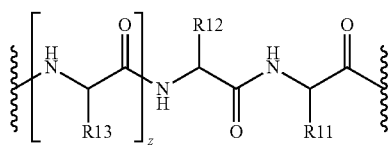

In formula (V), z is an integer ranging from 0 to 10, R11 can be —(CH$_2$)$_3$NHC(=NH)NH$_2$, —(CH$_2$)$_3$NH$_2$, —(CH$_2$)$_3$ NHCONH$_2$, —(CH$_2$)$_4$NHC(=NH)NH$_2$, —(CH$_2$)$_4$ NH$_2$ or —(CH$_2$)$_4$NHCONH$_2$, R12 may be H, methyl, ethyl, propyl, isopropyl, cyclopropyl, butyl, sec-butyl, isobutyl, tert-butyl, cyclobutyl, phenyl or benzyl, R13 may be hydrogen, methyl, isopropyl, cyclopropyl, butyl, sec-butyl, isobutyl, tert-butyl, cyclobutyl, cyclohexyl, phenyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$ NHCHO, —(CH$_2$)$_4$NHC(=NH)NH$_2$, —(CH$_2$)$_4$ NH$_2$, —(CH$_2$)$_4$NHCOCH$_3$, —(CH$_2$)$_4$NHCHO, —(CH$_2$)$_3$ NHCONH$_2$, —(CH$_2$)$_4$NHCONH$_2$, —CH$_2$CH$_2$CH(OH) CH$_2$NH$_2$, 2-pyridylmethyl, 3-pyridylmethyl or 4-pyridylmethyl.

In formula (III), -D is a cytotoxic agent selected from the group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

In one embodiment, C- is the conjugating unit selected from the group consisting of

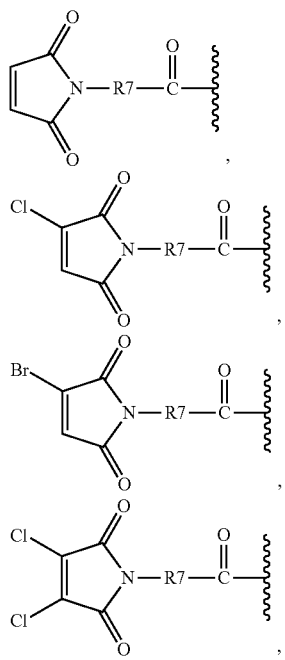

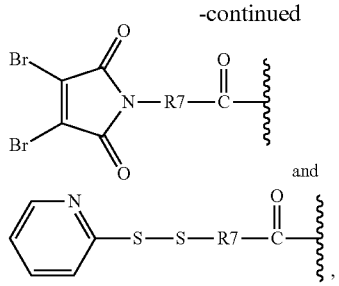

wherein R7 is selected from the group consisting of -1,5-pentylene-, -1,6-hexylene-, -1,4-cyclohexylene-, —(CH$_2$CH$_2$O)$_r$—CH$_2$— and —(CH$_2$CH$_2$O)$_r$—CH$_2$—CH$_2$—, and r is an integer ranging from 2-5.

In one embodiment, -SAAs- is the sugar amino acid unit selected from the group consisting of

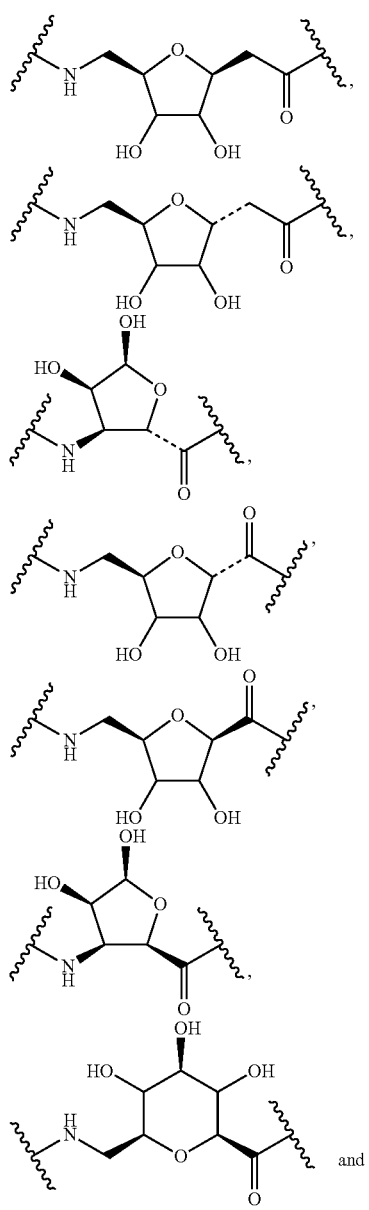

and

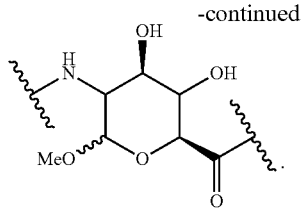

In one embodiment, -AAs- is the peptide unit selected from the group consisting of -Val-Cit-, -Val-Lys-, -Val-Arg-, -Phe-Cit-, -Phe-Lys- and -Phe-Arg-.

In one embodiment, -D is the cytotoxic agent selected from the group consisting of In formula (VI), p is an integer ranging from 1 to 20, and L- is a ligand unit selected from the group consisting of full-length antibodies, antibody fragments, proteins, smaller molecular weight proteins, polypeptides, oligopeptides, aptamers, lectins, glycoproteins, lipoproteins, glycolipids, vitamins, nutrient-transport molecules, hormones, monosaccharides, disaccharides, oligosaccharides, polysaccharides and any other cell binding molecules or substance.

In formula (VI), C- is a conjugating unit selected from the group consisting of,

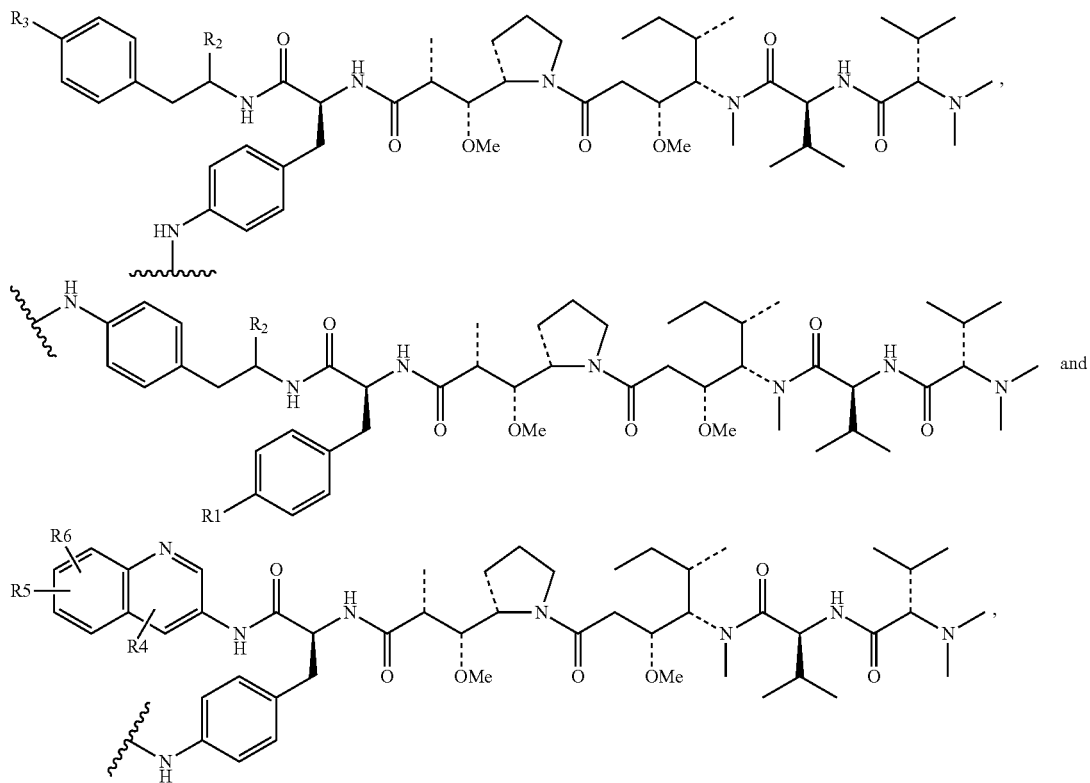

wherein R1, R2, R3, R4, R5 and R6 are each, independently, hydrogen, amino, nitro, halogen, hydroxyl, methoxy, ethoxy, carboxylic acid, methoxycarbonyl, ethoxycarbonyl, methylamino, dimethylamino, ethylamino, diethylamino, 1-pyrrolidinyl, 1-piperidinyl, 1-piperazinyl, aminocarbonyl, methylaminocarbonyl, dimethylaminocarbonyl, ethylaminocarbonyl, diethylaminocarbonyl, 1-pyrrolidinylcarbonyl, 1-piperidinylcarbonyl, 1-piperazinylcarbonyl, methyl, ethyl, propyl, isopropyl or phenyl.

Ligand Drug Conjugates

One embodiment of the disclosure provides a ligand-drug conjugate of formula (VI) or a pharmaceutically acceptable salt or solvate thereof:

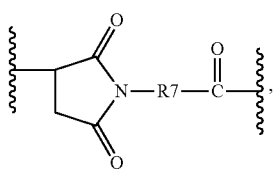

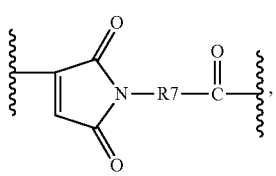

L-(C-SAAs-AAs-D)p          (VI)

-continued

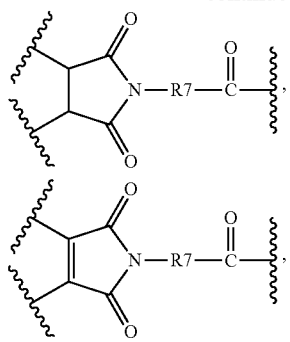

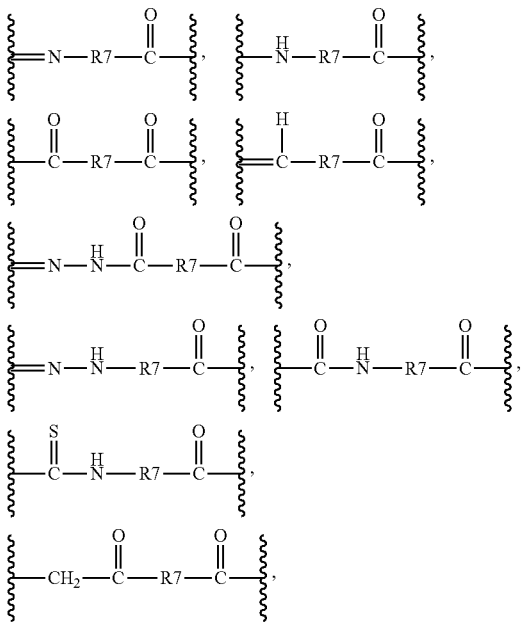

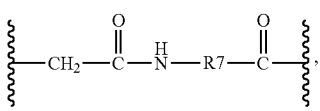

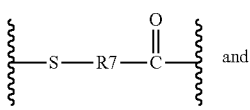 and

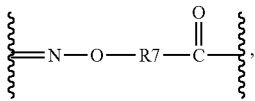

wherein R7 is selected from the group consisting of —C1-C10 alkylene-, —C3-C8 carbocyclo-, —O—(C1-C8 alkyl)-, -arylene-, —C1-C10 alkylene-arylene-, -arylene-C1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, —(C3-C8 heterocyclo)-C1-C10 alkylene-, —(CH$_2$CH$_2$O)$_r$— and —(CH$_2$CH$_2$O)$_r$—CH$_2$—, and r is an integer ranging from 1 to 10.

In formula (VI), -SAAs- is a sugar amino acid unit of formula (IV):

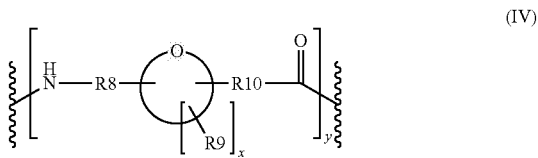 (IV)

In formula (IV), x is an integer ranging from 1 to 8, y is an integer ranging from 1 to 4,

can be a tetrahydrofuran, dihydrofuran, tetrahydropyran or dihydropyran ring, each of R8 and R10 may be, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 may be, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring.

In formula (VI), -AAs- is a peptide unit of formula (V):

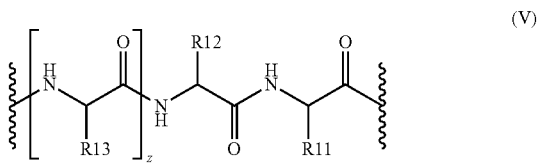 (V)

In formula (V), z is an integer ranging from 0 to 10, R11 can be —(CH$_2$)$_3$NHC(=NH)NH$_2$, —(CH$_2$)$_3$NH$_2$, —(CH$_2$)$_3$NHCONH$_2$, —(CH$_2$)$_4$NHC(=NH)NH$_2$, —(CH$_2$)$_4$NH$_2$ or —(CH$_2$)$_4$NHCONH$_2$, R12 can be H, methyl, ethyl, propyl, isopropyl, cyclopropyl, butyl, sec-butyl, isobutyl, tert-butyl, cyclobutyl, phenyl or benzyl, R13 can be hydrogen, methyl, isopropyl, cyclopropyl, butyl, sec-butyl, isobutyl, tert-butyl, cyclobutyl, cyclohexyl, phenyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$ NHCHO, —(CH$_2$)$_4$NHC(=NH)NH$_2$, —(CH$_2$)$_4$ NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl, 3-pyridylmethyl or 4-pyridylmethyl.

In formula (VI), -D is a cytotoxic agent selected from the group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

In one embodiment, the ligand unit (L-) is an antibody that binds to an antigen.

In one embodiment, the antibody can be a chimeric antibody, a humanized antibody or a functionally active fragment thereof.

In one embodiment, the antibody is attached to a linker unit through a cysteine residue of the antibody.

In formula (VI), p is an integer ranging from 2 to 8, or an integer of 4.

In one embodiment, the ligand unit can be folate, methotrexate or a folate receptor binding ligand that binds to a folate receptor.

In one embodiment, the ligand unit can be a luteinizing hormone-releasing hormone (LHRH), a luteinizing hormone-releasing hormone agonist, a luteinizing hormone-releasing hormone antagonist or a luteinizing hormone-releasing hormone receptor binding ligand that binds to a luteinizing hormone-releasing hormone receptor.

In one embodiment, C- in formula (VI) is the conjugating unit selected from the group consisting of

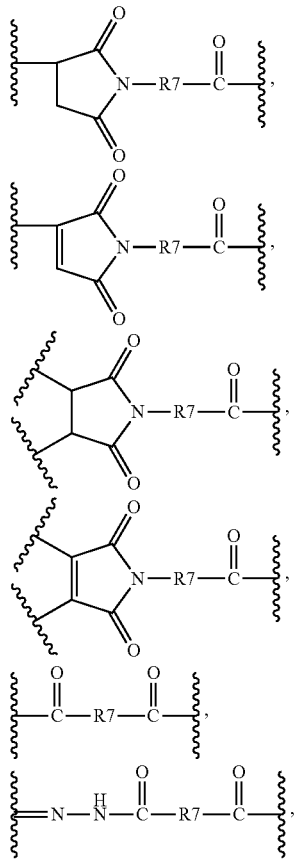

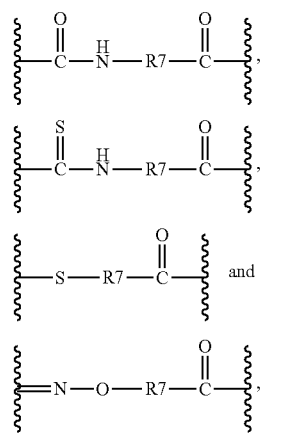

wherein R7 is selected from the group consisting of -1,5-pentylene-, -1,6-hexylene-, -1,4-cyclohexylene-, —(CH$_2$CH$_2$O)$_r$—CH$_2$— and —(CH$_2$CH$_2$O)$_r$—CH$_2$—CH$_2$—, and r is an integer ranging from 2-5.

In one embodiment, -SAAs- in formula (VI) is the sugar amino acid unit selected from the group consisting of

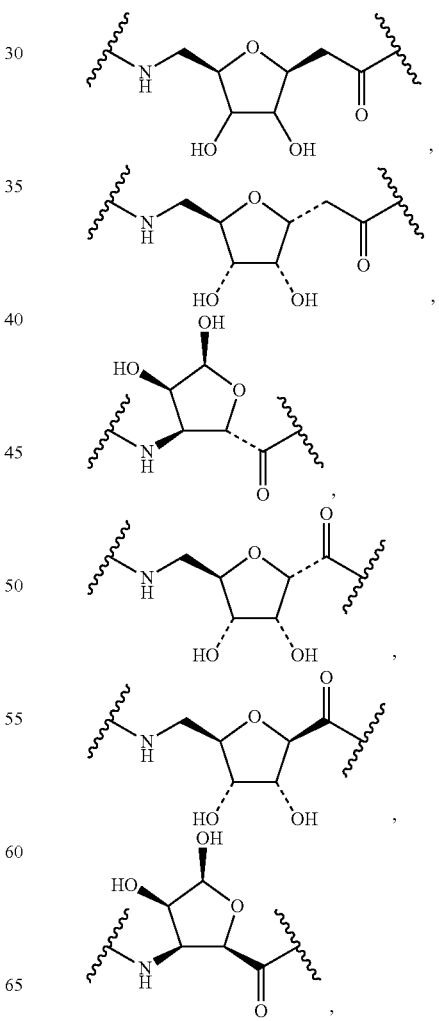

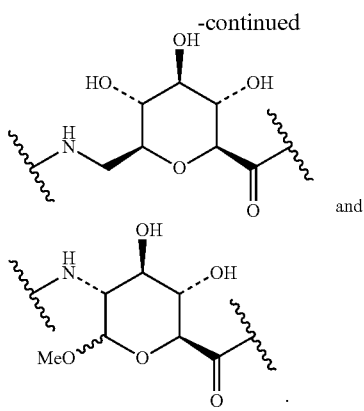

In one embodiment, -AAs- in formula (VI) is the peptide unit selected from the group consisting of -Val-Cit-, -Val-Lys-, -Val-Arg-, -Phe-Cit-, -Phe-Lys- and -Phe-Arg-.

In one embodiment, -D in formula (VI) is the cytotoxic agent selected from the group consisting of

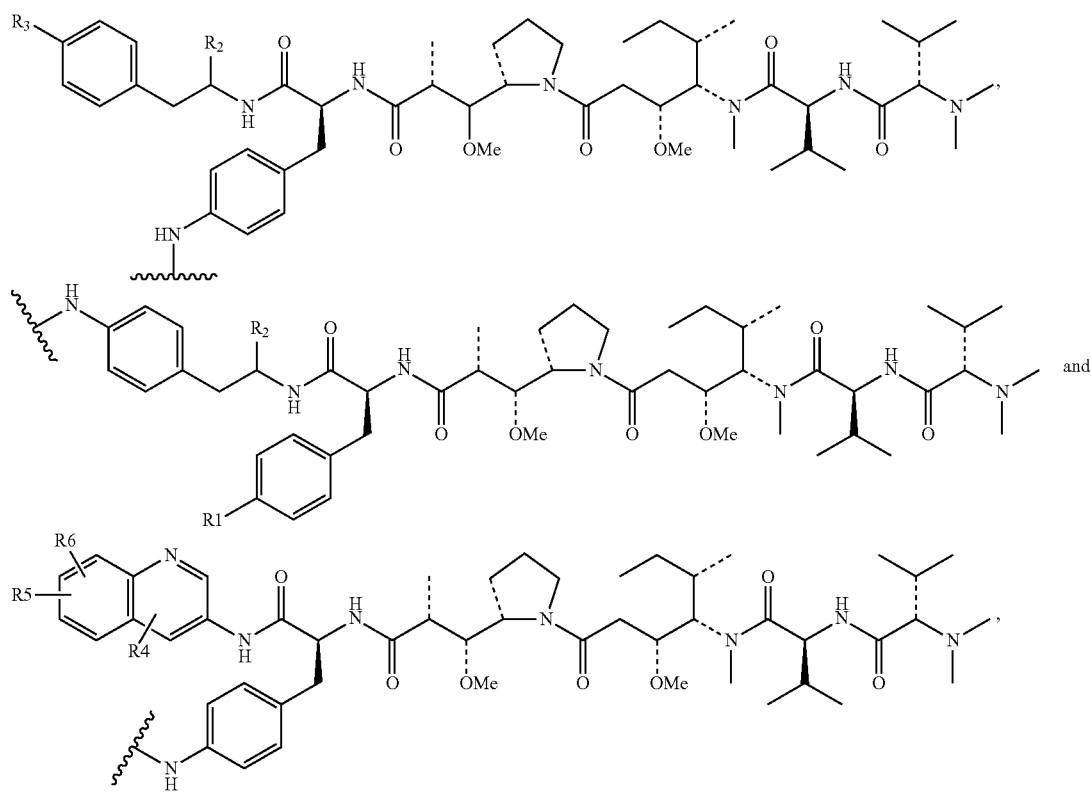

wherein R1, R2, R3, R4, R5 and R6 are each, independently, hydrogen, amino, nitro, halogen, hydroxyl, methoxy, ethoxy, carboxylic acid, methoxycarbonyl, ethoxycarbonyl, methylamino, dimethylamino, ethylamino, diethylamino, 1-pyrrolidinyl, 1-piperidinyl, 1-piperazinyl, aminocarbonyl, methylaminocarbonyl, dimethylaminocarbonyl, ethylaminocarbonyl, diethylaminocarbonyl, 1-pyrrolidinylcarbonyl, 1-piperidinylcarbonyl, 1-piperazinylcarbonyl, methyl, ethyl, propyl, isopropyl or phenyl.

The disclosure also provides Ligand Drug Conjugates for targeted delivery of drugs. The Ligand Drug Conjugate comprises a Ligand unit covalently linked to at least one Drug unit. The Drug units can be covalently linked to the Ligand unit directly or via a Linker unit.

The Conjugating Unit

The Conjugating unit is capable of linking a Ligand unit to a Linker unit to a Drug unit. Useful functional groups that can be present on a Ligand, either naturally or via chemical manipulation include, but are not limited to, sulfhydryl, amino, hydroxyl, carbonyl, formyl, and carboxyl. Suitable functional groups are sulfhydryl and amino. In one embodiment, sulfhydryl groups may be generated by reduction of the intramolecular disulfide bonds of a Ligand. In another embodiment, sulfhydryl groups can be generated by reaction of an amino group of a lysine of a Ligand with Traut's reagent or other sulfhydryl generating reagents. In certain embodiments, the Ligand is a recombinant antibody and is engineered to carry one or more lysines or cysteines.

In one embodiment, the Conjugating unit forms one bond with one sulfur atom of the Ligand unit. The sulfur atom can be derived from a sulfhydryl group of a Ligand.

In another embodiment, the Conjugating unit forms two bonds with two sulfur atoms of the Ligand unit. The two sulfur atoms may be derived from two sulfhydryl groups of a Ligand. The two sulfhydryl groups can be derived from a disulfide bond of a Ligand.

In some embodiments, the Drug Unit can be calicheamicin, camptothecin, maytansinoid or anthracycline. In some embodiments, the Drug Unit can be taxane, topoisomerase inhibitor, vinca alkaloid or the like. In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, and vinca alkaloids. Other cytotoxic agents include, for example, CC-1065, SN-38, topotecan, doxorubicin, rhizoxin, cyanomorpholino-doxorubicin, echinomycin, combretastatin, netropsin, epothilone, estramustine, cryptophysin, cemadotin, maytansinoid, discodermolide, eleutherobins or mitoxantrone.

The Drug Unit

In some embodiments, the Drug Unit can be an anti-tubulin agent. Examples of anti-tubulin agents include, auristatin, taxane and vinca alkaloid. Other anti-tubulin agents include, for example, baccatin derivatives, cemadotin, colchicine, colcimid, combretastatins, cryptophycins, discodermolide, eleutherobin, estramustine, maytansinoid, nocodazole or taxane analog.

In certain embodiments, the cytotoxic agent can be maytansinoids or another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent can be dolastatin. In certain embodiments, the cytotoxic or cytostatic agent is of the auristatin class. Thus, in a specific embodiment, the cytotoxic or cytostatic agent is MMAE.

The Ligand Unit

The Ligand unit of the Conjugate Compounds includes within its scope any unit of a Ligand that binds or reactively associates or complexes with a receptor, antigen or other receptive moiety associated with a given target-cell population. A Ligand is a molecule that binds to, complexes with, or reacts with a moiety of a cell population sought to be targeted. In one aspect, the Ligand unit acts to deliver the Drug unit to the particular target cell population with which the Ligand unit reacts. Such Ligands include, but are not limited to, large molecular weight proteins such as, for example, full-length antibodies, antibody fragments, proteins, smaller molecular weight proteins, polypeptides, oligopeptides, aptamers, lectins, glycoproteins, non-peptides, vitamins, nutrient-transport molecules (such as, but not limited to, transferrin), or any other cell binding molecule or substance.

A Ligand unit can form a bond to a Linker unit or a Drug unit. A Ligand unit may form a bond to a Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These heteroatoms may be present on the Ligand in the Ligand's natural state, for example a naturally-occurring antibody, or may be introduced into the Ligand via chemical modification.

In one embodiment, a Ligand has a sulfhydryl group and the Ligand bonds to the Linker unit via the sulfhydryl group's sulfur atom. In another embodiment, the Ligand has one or more lysine residues that may be chemically modified to introduce one or more sulfhydryl groups. The Ligand unit bonds to the Linker unit via the sulfhydryl group. Reagents that can be used to modify lysines include, but are not limited to, N-succinimidyl S-acetylthioacetate (SATA) and 2-Iminothiolane hydrochloride (Traut's Reagent).

In another embodiment, the Ligand has one or more carbohydrate groups that may be chemically modified to have one or more sulfhydryl groups. The Ligand unit bonds to the Linker unit via the sulfhydryl group's sulfur atom. In yet another embodiment, the Ligand has one or more carbohydrate groups that may be oxidized to provide an aldehyde (—CHO) group (see, e.g., Laguzza et al., 1989, J. Med. Chem. 32(3):548-55). The corresponding aldehyde can form a bond with a reactive site on a portion of a Linker unit. Reactive sites that can react with a carbonyl group on a Ligand include, but are not limited to, hydrazine and hydroxylamine. Other protocols for the modification of proteins for the attachment or association of Drug units are described in Coligan et al., Current Protocols in Protein Science, vol. 2, John Wiley & Sons (2002), incorporated herein by reference.

The Ligand unit includes, for example a protein, polypeptide, or peptide, but are not limited to, transferrin, epidermal growth factors ("EGF"), bombesin, gastrin, gastrin-releasing peptide, platelet-derived growth factor, IL-2, IL-6, transforming growth factor ("TGF"), such as TGF-α or TGF-β, vaccinia growth factor ("VGF"), insulin and insulin-like growth factors I and II, lectins and apoprotein from low-density lipoprotein.

The Ligand unit also includes an antibody, such as polyclonal antibodies or monoclonal antibodies. The antibody may be directed to a particular antigenic determinant, including for example a cancer cell antigen, a viral antigen, a microbial antigen, a protein, a peptide, a carbohydrate, a chemical, nucleic acid, or fragments thereof. Methods of producing polyclonal antibodies are known in the prior art. A monoclonal antibody (mAb) to an antigen-of-interest can be prepared using any technique known in the prior art. These include, but are not limited to, the hybridoma technique originally described by Köhler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). Such antibodies can be of any immunoglobulin class including IgG, IgM, IgE, IgA, and IgD and any subclass thereof. The hybridoma producing the mAbs for use in the disclosure may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies can be made by any of numerous techniques known in the prior art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16).

The antibody may also be a bispecific antibody. Methods for making bispecific antibodies are known in the prior art. Traditional production of full-length bispecific antibodies is based on the coexpression of two immunoglobulin heavy chain-light chain pairs, where the two chains have different specificities (see, e.g., Milstein et al., 1983, Nature 305:537-539; International Publication No. WO 93/08829, Traunecker et al., 1991, EMBO J. 10:3655-3659).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies has a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details of generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies may be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that the antibody from which the fragment, derivative or analog is derived recognized. Specifically, in an exemplary embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences may be used in binding assays with the antigen by any binding assay method known in the prior art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3): 961-969).

Other useful antibodies include fragments of antibodies such as, but not limited to, F(ab')2 fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which may be made using standard recombinant DNA techniques, also may be used. (See, e.g., U.S. Pat. No. 4,816,567; and U.S. Pat. No. 4,816,397.) Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies may be produced by recombinant DNA techniques known in the prior art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229: 1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be used. Human antibodies can be prepared, for example, using transgenic mice that are incapable of expressing endogenous immunoglobulin heavy and light chain genes, but which may express human heavy and light chain genes. The transgenic mice are immunized in the normal fashion with a selected antigen, e.g., all or a portion of a polypeptide of the invention. Monoclonal antibodies directed against the antigen may be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. see, e.g., U.S. Pat. Nos. 5,625,126; 5,633,425; 5,569,825; 5,661, 016; and 5,545,806. Other human antibodies may be obtained commercially from, for example, Abgenix, Inc. (Freemont, Calif.) and Genpharm (San Jose, Calif.).

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies also can be produced using various techniques known in the prior art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative may contain one or more unnatural amino acids.

Antibodies may have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen may be obtained commercially or from other sources or produced by any method known to one of skill in the art such as, e.g., chemical synthesis or recombinant expression techniques. The nucleotide sequence encoding antibodies immunospecific for a cancer cell antigen may be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (Medimmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens may be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

In some embodiments, known antibodies for the treatment or prevention of an autoimmune disease are used in accordance with the compositions and methods of the invention. Antibodies immunospecific for an antigen of a cell that is responsible for producing autoimmune antibodies may be obtained from a commercial or other source or produced by any method known to one of skill in the art such as, e.g., chemical synthesis or recombinant expression techniques.

In some embodiments, the antibody is immunospecific for the treatment of an autoimmune disease such as, for example, anti-nuclear antibody; anti-ds DNA; anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL 70; anti-Jo; anti-U1 RNP; anti-La/SSB; anti-SSA; anti-SSB; anti-perital cells antibody; anti-histones; anti-RNP; C ANCA; P ANCA; anti centromere; anti fibrillarin, and anti-GBM antibody. In one embodiment, the Ligand binds to an activated lymphocyte that is associated with an autoimmune disease.

In certain embodiments, the antibody may bind to a receptor or a receptor complex expressed on a target cell (e.g., an activated lymphocyte). The receptor or receptor complex may comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNF R1, TNFR2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

In another specific embodiment, useful Ligands immunospecific for a viral or a microbial antigen are monoclonal antibodies. The antibodies can be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment or prevention of viral or microbial infection in accordance with the methods disclosed herein. Examples of antibodies available useful for the treatment of viral infection or microbial infection include, but are not limited to, SYNAGIS (Medimmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (e.g., *Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (e.g., *Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma ijaponicum, Schistosoma mansoni, Schistosoma haematobium*, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non A/Non B Hepatitis virus, Rhinoviridae, Coronaviridae, Rotoviridae, and Human Immunodeficiency Virus.

The antibody also can be an antibody that is present on a target cell or target cell population. For example, transmembrane polypeptides and other markers can be specifically expressed on the surface of one or more particular type(s) of target cells (e.g., a cancer cell) as compared to on one or more normal cells (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the prior art, and may prepare for use in generating antibodies using methods and information which are well known in the prior art.

EXAMPLES

The disclosure will be described in detail by the following examples. Among them, MMAE (a well-known toxin), auristatin F (AF, a well-known toxin) and vedotin (a well-known linker-toxin) were purchased from Concortis Biotherapeutics. Z-Val-Cit-OH, Z-Phe-Cit-OH and various sugar amino acids were synthesized based on the literatures.

The abbreviations used in linker, toxin and linker-toxin and their corresponding chemical structures are listed in Table 1.

TABLE 1
| | |
|---|---|
| SAA1 | 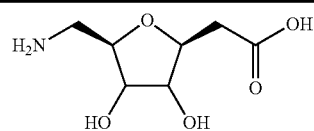 |
| SAA2 | 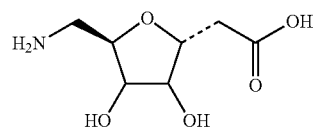 |
| SAA3 | 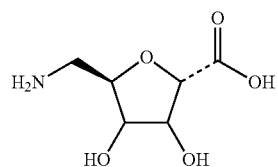 [SMILES: NC[C@H]1O[C@H](C(=O)O)C(O)C1O] |
| SAA4 | 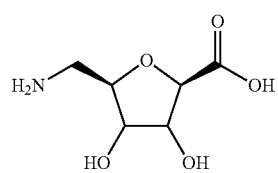 [SMILES: NC[C@H]1O[C@@H](C(=O)O)C(O)C1O] |
| SAA5 | 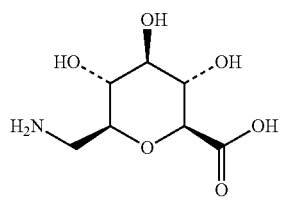 [SMILES: NC[C@@H]1O[C@H](C(=O)O)[C@@H](O)[C@H](O)[C@H]1O] |
| SAA6 | 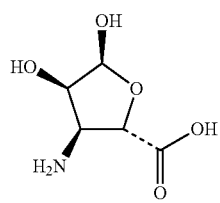 [SMILES: N[C@H]1[C@@H](O)[C@@H](O)O[C@@H]1C(=O)O] |
| SAA7 | 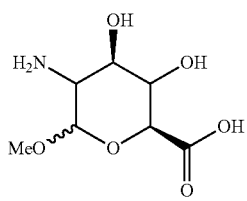 [SMILES: COC1O[C@H](C(=O)O)C(O)[C@H](O)C1N] |
| SAA8 | 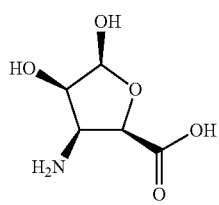 [SMILES: N[C@H]1[C@@H](O)[C@@H](O)O[C@H]1C(=O)O] |
| MC | 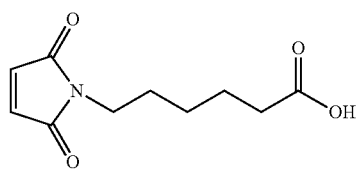 [SMILES: O=C(O)CCCCCN1C(=O)C=CC1=O] |

TABLE 1-continued
ZC
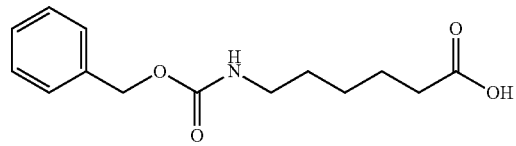 [SMILES: O=C(O)CCCCCNC(=O)OCc1ccccc1]
MC-OPFP
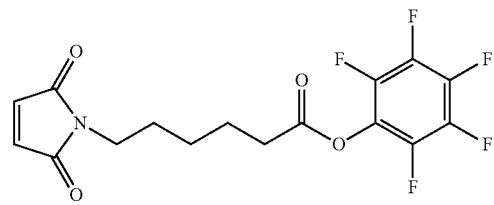 [SMILES: O=C(CCCCCN1C(=O)C=CC1=O)Oc1c(F)c(F)c(F)c(F)c1F]
Cl2MC
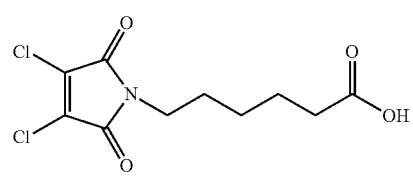 [SMILES: O=C(O)CCCCCN1C(=O)C(Cl)=C(Cl)C1=O]
Cl2MC-OPFP
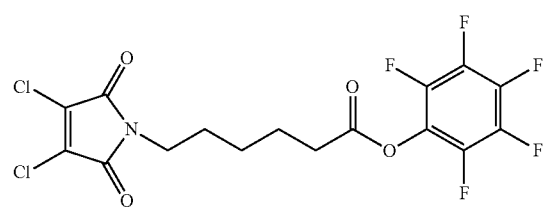 [SMILES: O=C(CCCCCN1C(=O)C(Cl)=C(Cl)C1=O)Oc1c(F)c(F)c(F)c(F)c1F]
Br2MC
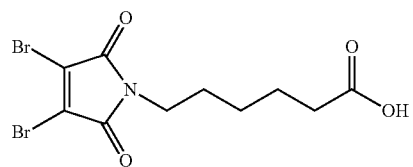
Br2MC-OPFP
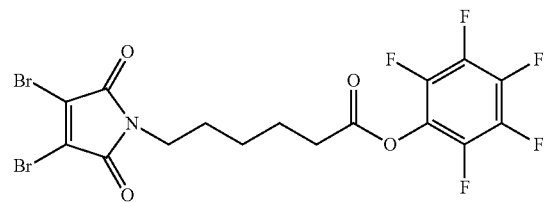
GA
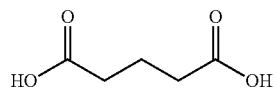
AF
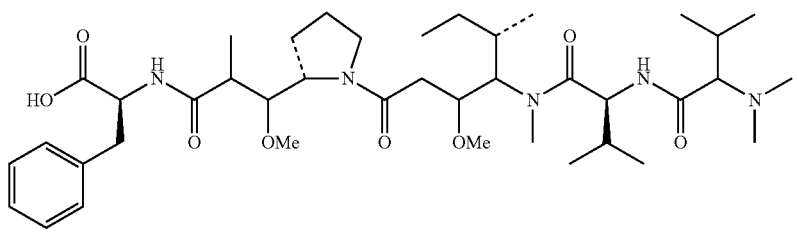

TABLE 1-continued
ANF 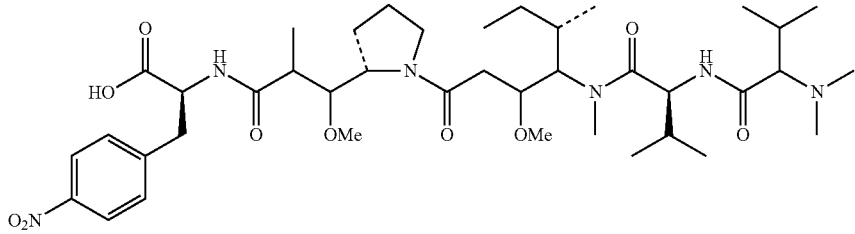
AAF 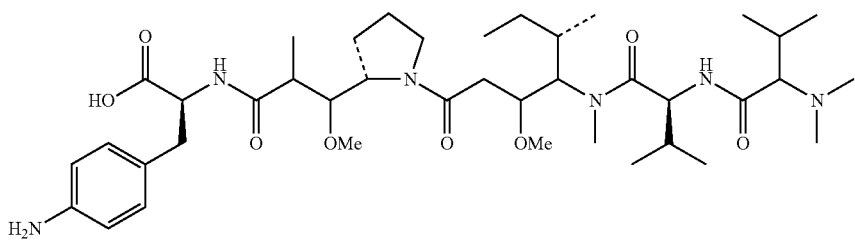
PEA 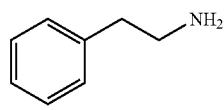
NPEA 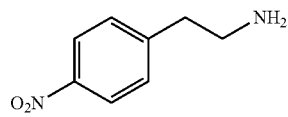 [SMILES: NCCc1ccc([N+](=O)[O-])cc1]
NPEA (COOR) 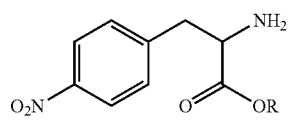
APEA 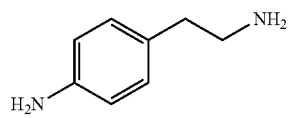
APEA (COOR) 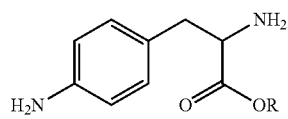
3AQ 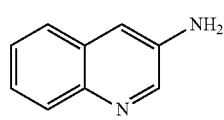 [SMILES: Nc1cnc2ccccc2c1]

<Toxin>

Example 1

Synthesis of NPEA-AF and APEA-AF

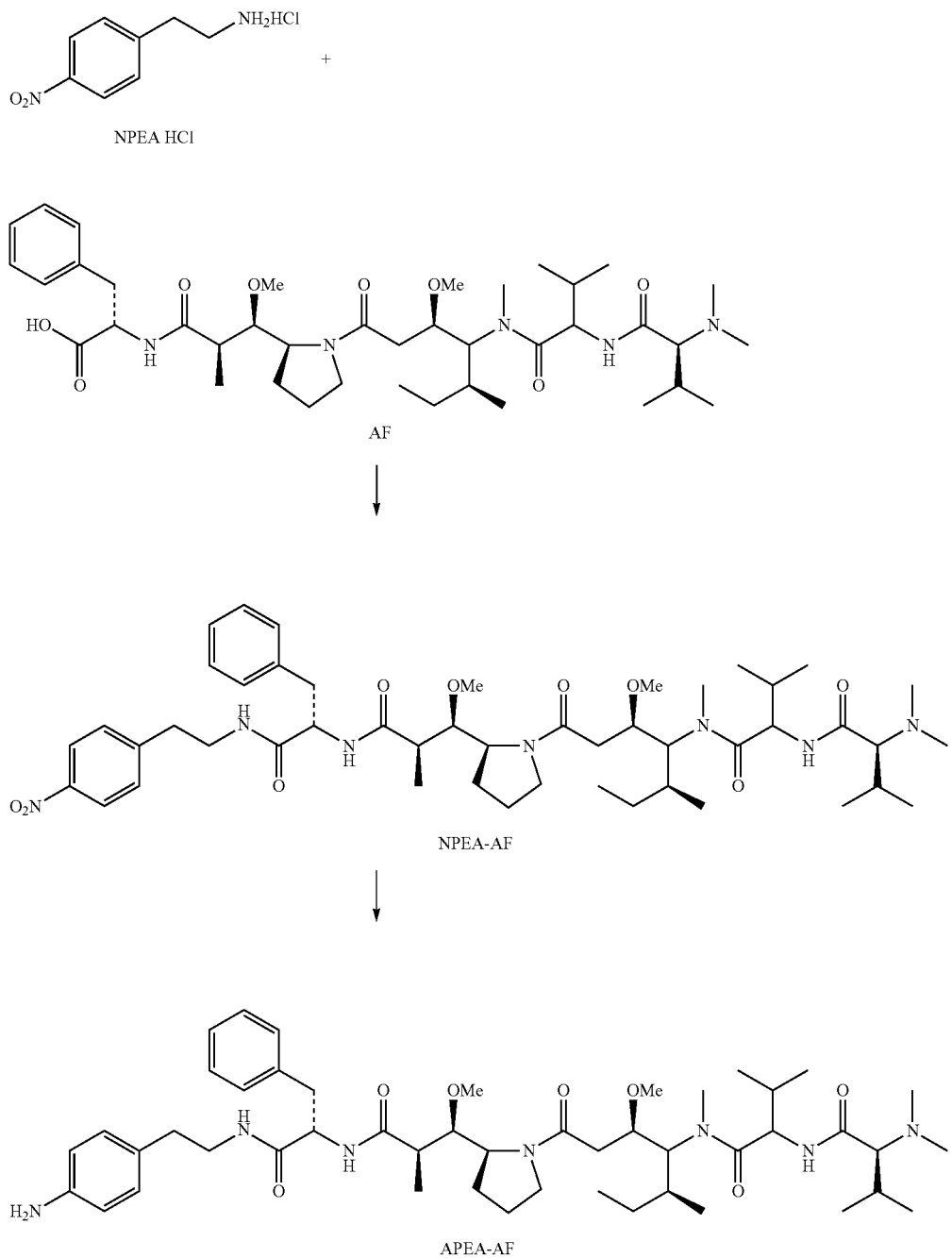

HATU (101 mg, 0.2654 mmol) was added to a stirred solution of AF (165 mg, 0.2212 mmol), 4-nitrophenethyl-amine hydrochloride (45 mg, 0.2212 mmol) and DIPEA (0.155 mL, 0.8847 mmol) in DMF (0.100 mL) and dichloromethane (1 mL). After stirring at room temperature for 12 hours, the solvents were removed and the residue was purified by preparative reverse phase HPLC, then lyophilized to afford NPEA-AF as a white powder (188 mg, 95%). LC-MS: NPEA-AF ($C_{48}H_{75}N_7O_9$) required [MH$^+$]= 894.6, found [MH$^+$]=895.6.

NPEA-AF (188 mg, 0.2103 mmol) was dissolved in ethanol (50 mL) and then mixed with HCl (0.4206 mmol) and palladium catalyst (22 mg). The mixture was stirred for 16 hours under hydrogen atmosphere. The catalyst was filtered off and washed with 20 mL ethanol. The solvent was removed under reduce pressure. The residue was mixed with water (10 mL) and then lyophilized to Afford APEA-AF as white powder (178 mg, 98%). LC-MS: APEA-AF ($C_{48}H_{77}N_7O_9$) required [MH$^+$]=864.6, found [MH$^+$]=865.5.

Example 2

Synthesis of NPEA(COOMe)-AF and NPEA(COOH)-AF

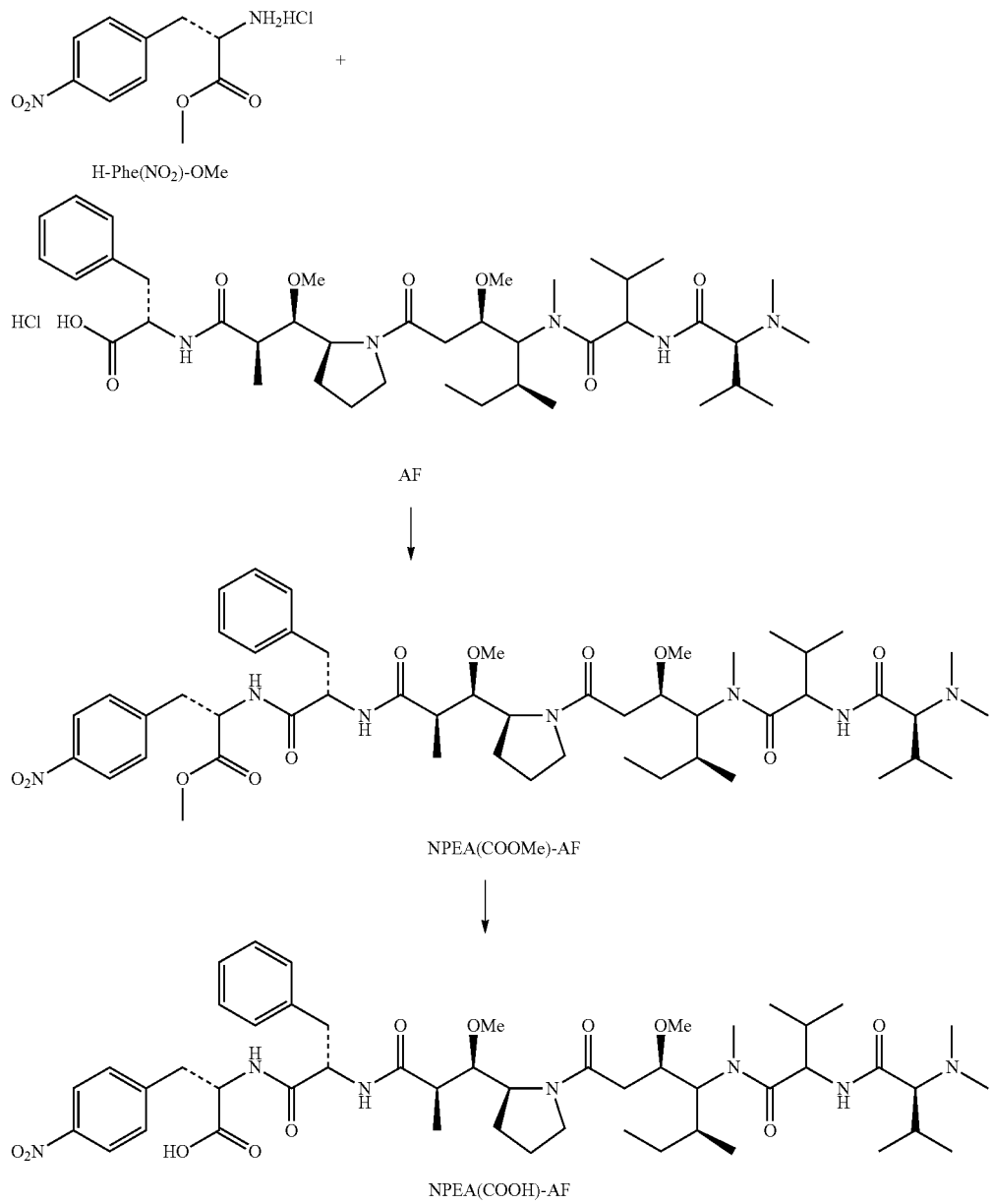

Auristatin F (200 mg, 0.26 mmol) was dissolved in small amount of DMF (1 mL) and then diluted with DCM (10 mL). The solution was immersed in an ice-bath and then L-(4-nitro)phenylalanine methyl ester hydrochloride (67 mg, 0.26 mmol) and HATU (117 mg, 0.31 mmol) were charged. After DIPEA (0.18 mL) was added, the reaction mixture was removed from the ice-bath and then stirred at room temperature overnight. The solvents were evaporated under reduced pressure and the residue was purified by preparative HPLC (46% acetonitrile in water with 0.1% TFA; UV 210 nm; ODS-3 column 30*250 mm; flow rate 25 mL/min) to afford NPEA(COOMe)-AF as white solid (175 mg, 72%). LC-MS: NPEA(COOMe)-AF ($C_{50}H_{77}N_7O_{11}$) required [MH$^+$]=952.6, found [MH$^+$]=952.5.

NPEA(COOMe)-AF (20 mg) was dissolved in a mixture of THF and water (1:1, 10 mL) and then treated with sodium hydroxide (2.5 mg). After 2 hours, the THF was evaporated under reduced pressure. The aqueous solution was acidified with 2N hydrochloric acid and then submitted to freeze-drying. The crude product was purified by preparative HPLC (46% acetonitrile in water with 0.1% TFA; UV 210 nm; ODS-3 column 30*250 mm; flow rate 24 mL/min) to afford NPEA(COOH)-AF as white solid (15 mg, 75%). LC-MS: NPEA(COOH)-AF ($C_{49}H_{75}N_7O_{11}$) required [MH$^+$]=938.6, found [MH$^+$]=939.3.

Example 3

Synthesis of APEA(COOMe)-AF and APEA(COOH)-AF

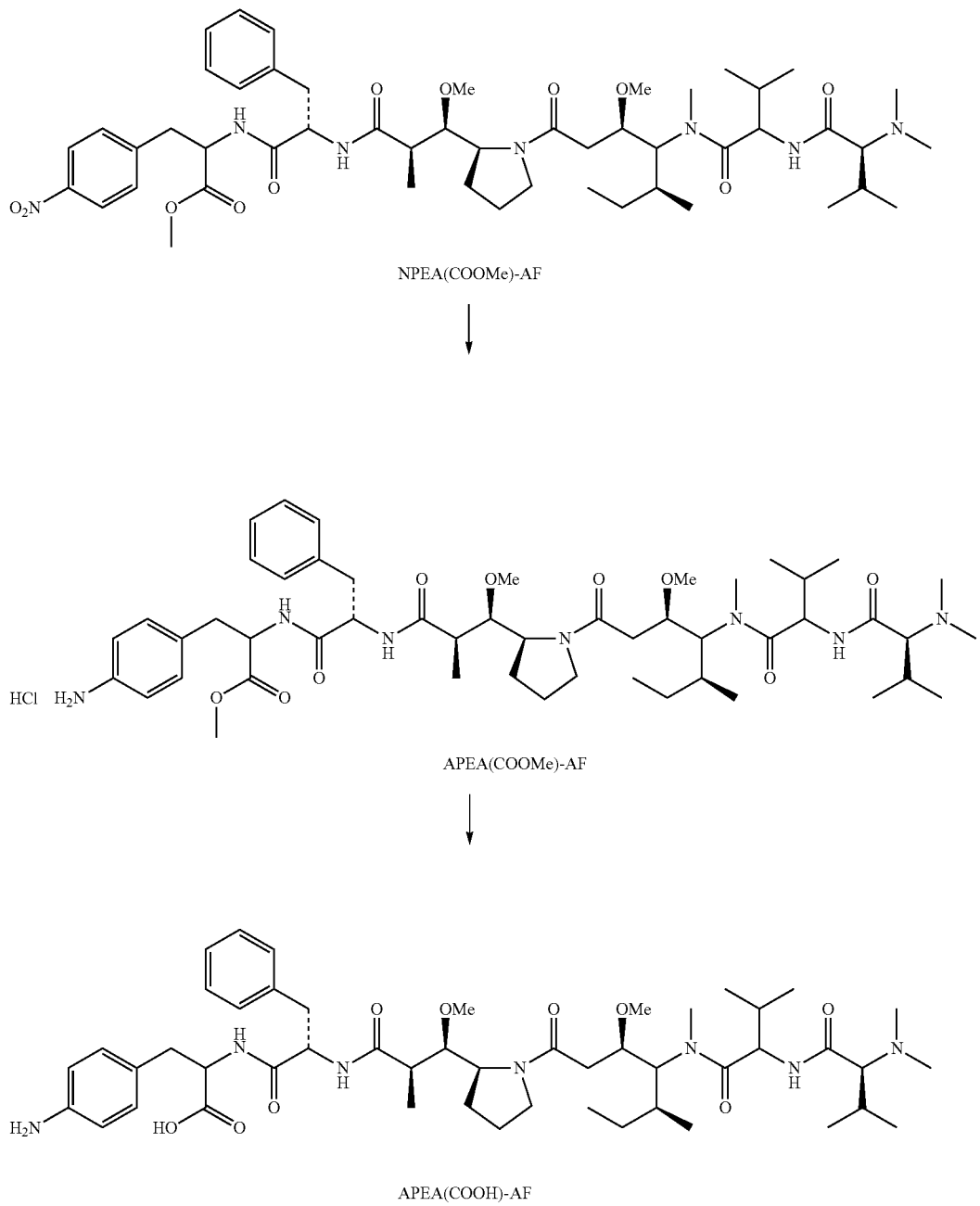

NPEA(COOMe)-AF (100 mg, 0.105 mmol) was dissolved in ethanol (10 mL) contains 2N hydrochloric acid (15 µL). After Pd/C (10%, 17 mg) was charged, the reaction was applied a hydrogen balloon and stirred overnight. The catalyst Pd/C was filtered off through a pad of celite and then the filtrate was evaporated under reduced pressure. The crude product was purified by preparative HPLC (33% ACN in water with 0.1% TFA; UV 210 nm; ODS-3 column 30*250 mm; flow rate 24 mL/min) to afford APEA(COOME)-AF as white solid (36 mg). LC-MS: NPEA(COOH)-AF ($C_{50}H_{79}N_7O_9$) required [MH$^+$]=922.6, found [MH$^+$]=923.5.

APEA(COOMe)-AF (25 mg) was dissolved in a mixture of THF and water (1:1, 10 mL) and then treated with sodium hydroxide (2.1 mg). After 2 hours, the THF was evaporated under reduced pressure. The aqueous solution was acidified with 2N hydrochloric acid and then submitted to freeze-drying. The crude product was purified by preparative HPLC (29% acetonitrile in water with 0.1% TFA; UV 210 nm; ODS-3 column 30*250 mm; flow rate 24 mL/min) to afford APEA(COOH)-AF as white solid (14 mg, 58%). LC-MS: APEA(COOH)-AF ($C_{49}H_{77}N_7O_9$) required [MH$^+$]=908.6, found [MH$^+$]=909.5.

Example 4
Synthesis of PEA-ANF and PEA-AAF
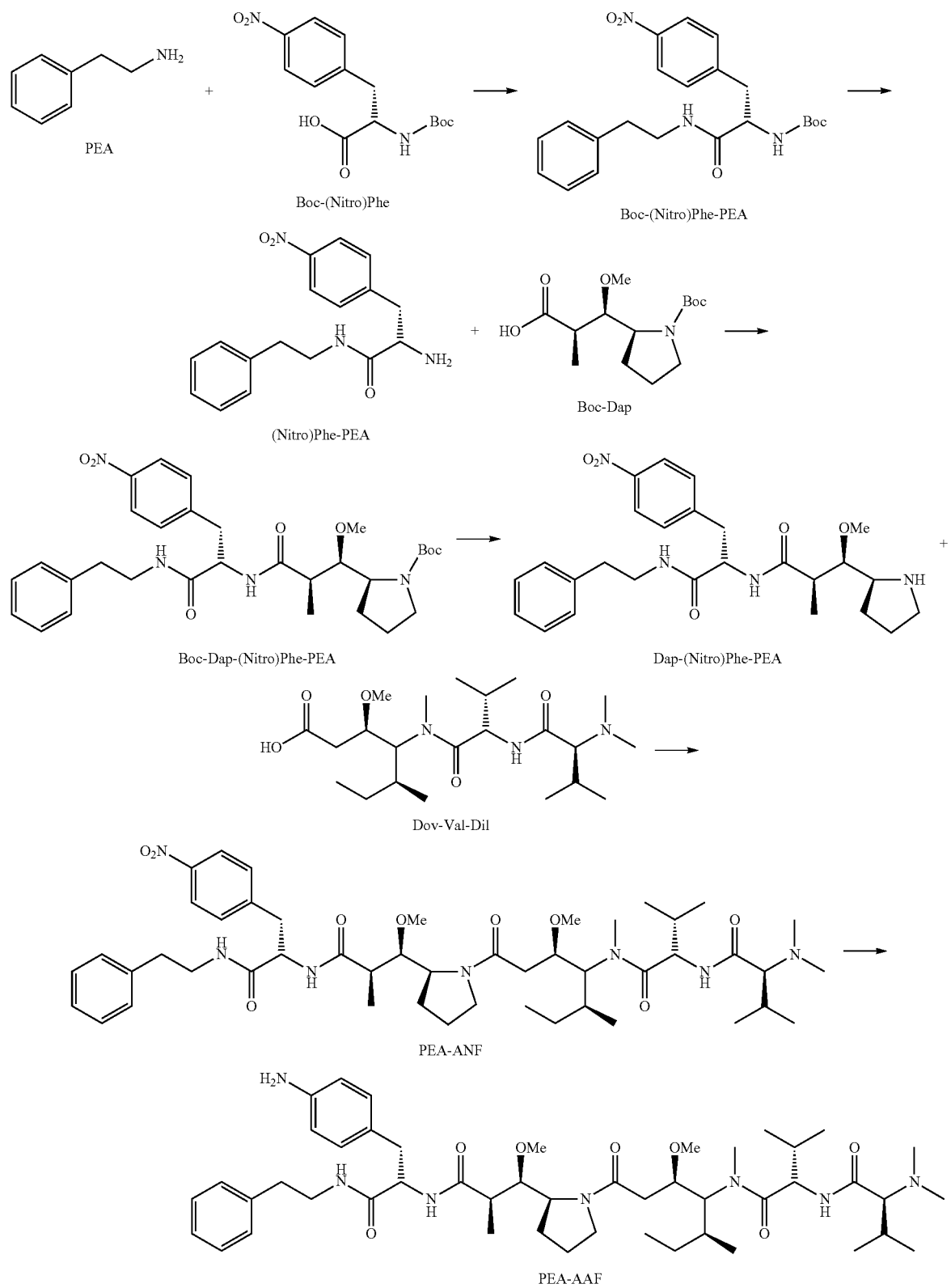

To a flask contains dichloromethane (200 mL) was added Boc-L-p-nitrophenylalanine (4.66 g, 15 mmol) and phenylethylamine (1.94 g, 16 mmol). Then, the coupling reagent N-ethoxycarbonyl-2-ethoxy-1,2-dihydroquinoline (EEDQ, 17 g, 17 mmol) was added into the solution and the mixture was stirred at room temperature overnight. The reaction was confirmed by TLC (EtOAc/n-Hex=1:1, Rf of product=0.5). The DCM was evaporated under reduced pressure. The solid product was boiled with h-hexane (200 mL) and filtered while hot. The solid product was washed with hot h-hexane (50 mL, 2 times) and aspirated to dry to afford Boc-(Nitro)Phe-PEA as off white powder (4.81 g, 77.6%).

Boc-(Nitro)Phe-PEA (4.80 g, 11.6 mmol) was dissolved in dichloromethane (150 mL) and then mixed with trifluoroacetic acid (6.84 g, 4.6 mL, 60 mmol). The solution was stand at room temperature overnight. The dichloromethane was evaporated under reduced pressure. The residue was mixed with THF (50 mL) and evaporated again. The residue was treated with 1N sodium carbonate solution (250 mL) and then extracted with dichloromethane (100 mL, 2 times). The organic solution was dried over anhydrous magnesium sulfate and filtered off. The filtrate was evaporated under reduced pressure and the light yellow residue was stirred with n-hexane (50 mL) until a solid formed. The n-hexane was evaporated under reduced pressure and the product was finally dried under high vacuum to afford quantitative (Nitro)Phe-PEA.

Dolaproline potassium salt (325 mg, 1.0 mmol) was dissolved in MeOH (20 mL) and then treated with teraethylammonium broimide (232 mg, 1.1 mmol). After 3 hours, the MeOH was evaporated under reduced pressure. The residue was treated with dichloromethane (10 mL) and then filtered to remove the KBr. The filtrate was mixed with (Nitro)Phe-PEA (422 mg, 1.1 mmol) and HATU (456 mg, 1.2 mmol). After stirring at room temperature overnight, the dichloromethane was evaporated under reduced pressure and the residue was purified by preparative HPLC (70% acetonitrile in water with 0.1% TFA; UV 210 nm; ODS-3 column 30*250 mm; flow rate 25 mL/min) to afford Boc-Dap-(Nitro)Phe-PEA as white solid (527 mg, yield 90%). LC-MS: Boc-Dap-(Nitro)Phe-PEA ($C_{31}H_{42}N_4O_7$) required [MH$^+$]=583.3, found [MH$^+$]=584.4.

Boc-Dap-(Nitro)Phe-PEA (527 mg, 0.9 mmol) was dissolved in dichloromethane (20 mL) and then treated with trifluoroacetic acid (7 mL). After 4 hours, the solvents were removed under reduced pressure. The residue was mixed with ethyl acetate (50 mL) and evaporated again. The residue was mixed with water (20 mL) and submitted to freeze-drying to afford Dap-(Nitro)Phe-PEA as white powder (426 mg, 98%). LC-MS: Dap-(Nitro)Phe-PEA ($C_{26}H_{34}N_4O_5$) required [MH$^+$]=483.3, found [MH$^+$]=484.3.

Dov-Val-Dil (64.5 mg, 0.15 mmol), Dap-(Nitro)Phe-PEA (72 mg, 0.15 mmol) and HATU (68 mg, 0.18 mmol) were dissolved in dichloromethane (20 mL) and then treated with DIPEA (86 mg, 0.66 mmol). After stirring at room temperature overnight, the dichloromethane was evaporated under reduced pressure and the residue was purified by preparative HPLC (43% acetonitrile in water with 0.1% TFA; UV 210 nm; ODS-3 column 30*250 mm; flow rate 25 mL/min) to afford PEA-ANF as white solid (96.7 mg, yield 72%). LC-MS: PEA-ANF ($C_{48}H_{75}N_7O_9$) required [MH$^+$]=894.6, found [MH$^+$]=895.6.

PEA-ANF (20 mg, 0.022 mmol) was dissolved in ethanol (30 mL) and then mixed with HCl (0.067 mmol). After a catalytic amount of 10% Pd/C (16 mg) was added, the reaction mixture was applied a hydrogen balloon and stirred overnight. After the catalyst was filtered off through a pad of celite, the filtrate was evaporated under reduced pressure to afford PEA-AAF as white solid (24.2 mg, 51%). LC-MS: PEA-AAF ($C_{48}H_{77}N_7O_7$) required [MH$^+$]=864.6, found [MH$^+$]=865.6.

Example 5

Synthesis of 3AQ-ANF and 3AQ-AAF

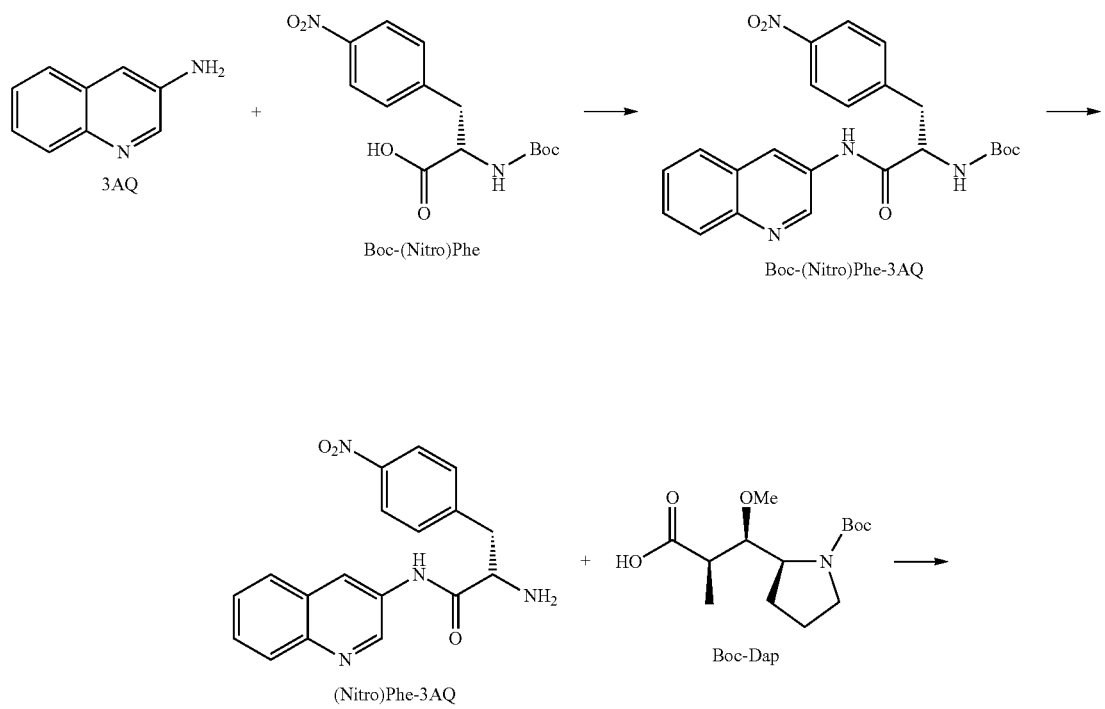

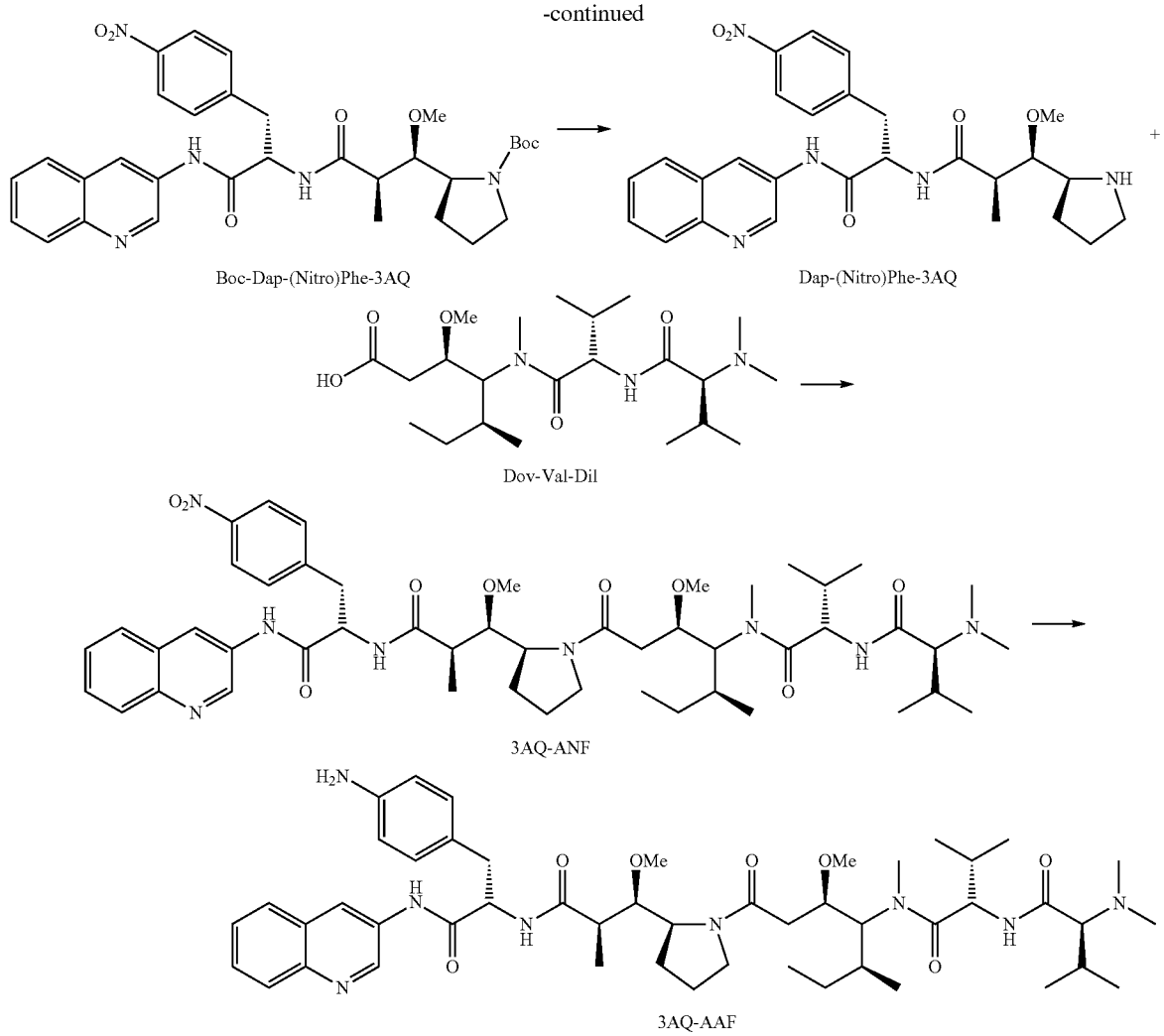

Boc-Dap-(Nitro)Phe-3AQ

Dap-(Nitro)Phe-3AQ

Dov-Val-Dil

3AQ-ANF

3AQ-AAF

Boc-(Nitro)Phe (46.55 g, 0.15 mol) was dissolved in dichloromethane (1 L) and then N-hydroxysuccinimide (17.26 g, 0.15 mol) and EDCI (28.76 g, 0.15 mol) were charged into the dichloromethane solution. After 4 hours, 3AQ (21.63 g, 0.15 mol) and ethylmorpholine (17.28 g, 0.15 mol) were charged into the dichloromethane solution and stirred at room temperature for 3 days. The dichloromethane was evaporated under reduced pressure. The residue was stirred with citric acid solution (1M, 500 mL) and ethyl acetate (500 mL) for 30 minutes. The solid product was filtered off, washed with water (200 mL, 2 times). The wet crude product was dissolved in hot acetone (1.5 L), dried over anhydrous magnesium sulfate and filtered. The filtrate was evaporated under reduced pressure to afford Boc-(Nitro)Phe-3AQ (31.52, 48.1%).

Boc-(Nitro)Phe-3AQ (30.55 g, 0.07 mol) was dissolved in dichloromethane (300 mL) and then treated with trifluoroacetic acid (50 mL, 74.45 g, 653 mmol). After stirred at room temperature overnight, the reaction mixture was evaporated under reduced pressure. Ethyl acetate (100 mL) was added to the oily residue and then evaporated under reduced pressure. This procedure was repeated for two more times and then diethyl ether (300 mL) was added to the oily product to force the trifluoroacetate to crash out. The solid product was suspended in a mixture of sodium carbonate solution (1 M, 500 mL) and methanol (500 mL) and stirred until it well suspended. The methanol was evaporated under reduced pressure and then the solid product was filtered off, washed with water (200 mL, 2 times). The wet product was then subjected to freeze-drying to afford (Nitro)Phe-3AQ (20.35 g, 86.4%).

Dolaproline potassium salt (487.5 mg, 1.5 mmol) was dissolved in MeOH (50 mL) and then treated with teraethylammonium bromide (316.4 mg, 1.4 mmol). After 4 hours, the MeOH was evaporated under reduced pressure. The residue was treated with dichloromethane (10 mL) and then filtered to remove the KBr. The filtrate was mixed with (Nitro)Phe-3AQ (556 mg, 1.65 mmol) and HATU (685 mg, 1.8 mmol). After stirring at room temperature overnight, the dichloromethane was evaporated under reduced pressure and the residue was purified by preparative HPLC (42% acetonitrile in water with 0.1% TFA; UV 210 nm; ODS-3 column 30*250 mm; flow rate 24 mL/min) to afford Boc-Dap-(Nitro)Phe-3AQ as white solid (781 mg, yield 86%). LC-MS: Boc-Dap-(Nitro)Phe-3AQ ($C_{32}H_{39}N_5O_7$) required [MH$^+$]=606.3, found [MH$^+$]=607.4.

Boc-Dap-(Nitro)Phe-3AQ (606 mg, 1 mmol) was dissolved in dichloromethane (10 mL) and then treated with trifluoroacetic acid (6 mL). After 2 hours, the solvents were removed under reduced pressure. The residue was mixed with ethyl acetate (50 mL) and evaporated again. The residue was mixed with water (20 mL) and submitted to freeze-drying to afford Dap-(Nitro)Phe-3AQ as white powder (500 mg, 99%). LC-MS: Dap-(Nitro)Phe-3AQ ($C_{27}H_{31}N_5O_5$) required [MH$^+$]=506.2, found [MH$^+$]=507.1.

Dov-Val-Dil (200 mg, 0.466 mmol), Dap-(Nitro)Phe-3AQ (236 mg, 0.466 mmol) and HATU (213 mg, 0.56 mmol) were dissolved in dichloromethane (5 mL) and then treated with DIPEA (267 mg, 2.05 mmol). After stirring at room temperature overnight, the dichloromethane was evaporated under reduced pressure and the residue was purified by preparative HPLC (43% acetonitrile in water with 0.1% TFA; UV 210 nm; ODS-3 column 30*250 mm; flow rate 25 mL/min) to afford 3AQ-ANF as white solid (345.2 mg, yield 82%). LC-MS: 3AQ-ANF ($C_{49}H_{72}N_8O_9$) required [MH$^+$]=917.5, found [MH$^+$]=918.5.

3AQ-ANF (105 mg, 0.114 mmol) was dissolved in ethanol (30 mL). After a catalytic amount of 10% Pd/C (10 mg) was added, the reaction mixture was applied a hydrogen balloon and stirred for 4 hours. After the catalyst was filtered off through a pad of celite, the filtrate was evaporated under reduced pressure. The residue was then purified by preparative HPLC (36% acetonitrile in water with 0.1% TFA; UV 210 nm; ODS-3 column 30*250 mm; flow rate 25 mL/min). The fraction contains 3AQ-ANF was evaporated under reduced pressure to remove acetonitrile. The acidic aqueous solution was basified with sodium carbonate and then filtered to obtain 3AQ-ANF (80 mg, 79%). LC-MS: 3AQ-ANF ($C_{49}H_{74}N_8O_7$) required [MH$^+$]=887.6, found [MH$^+$]=888.5.

<Sugar Amino Acid>

Example 6

Synthesis of Derivatives of Sugar Amino Acid 1 (SAA1) and Sugar Amino Acid 2 (SAA2)

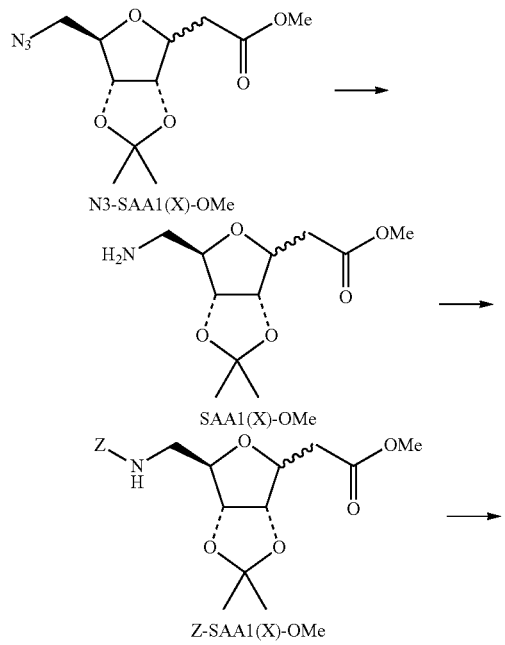

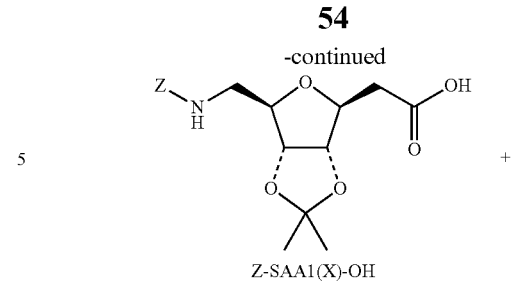

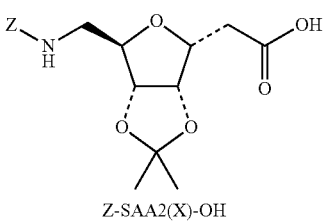

Ribose derivative N3-SAA1(X)-OMe (3.6 g) was dissolved in methanol. After a catalytic amount of Pd/C was added, a hydrogen balloon was applied to the reaction mixture and stirred overnight. The catalyst was filtered off through a pad of celite and the methanol was evaporated under reduced pressure to afford SAA1(X)-OMe as light yellow liquid (3.14 g).

To a solution of SAA1(X)-OMe (8.72 g) in DCM (300 mL) was added Z-OSu (9.75 g) and DIPEA (6.8 mL). After 17 hours, the reaction mixture was washed with 1N sodium carbonate. The organic layer was dried over anhydrous magnesium sulfate. The dichloromethane was evaporated under reduced pressure to afford crude Z-SAA1(X)-OMe as brown liquid (13.6 g).

The crude Z-SAA1(X)-OMe (1 g) was dissolved in THF (50 mL) and then treated with 1N KOH (6 mL). After 3 hours, the THF was evaporated under reduced pressure. The crude aqueous solution was mixed with DCM (100 mL) and then carefully acidified by citric acid solution until the pH reached about 3-4. The organic solution was washed with water several times and then dried over anhydrous magnesium sulfate. After the removal of dichloromethane, the crude liquid was purified by preparative HPLC (45% acetonitrile in water with 0.1% TFA; UV 210 nm; ODS-3 column 30×500 mm; flow rate 55 mL/min; Z-SAA1(X)-OH RT 11 min; Z-SAA2(X)-OH RT 12 min). The Z-SAA1(X)-OH and Z-SAA2(X)-OH solutions were immediately basified after collection. After the removal of acetonitrile, the aqueous solutions of Z-SAA1(X)-OH and Z-SAA2(X)-OH were mixed with dichloromethane and then carefully acidified by citric acid solution until the pH reached about 3-4. Both Z-SAA1(X)-OH and Z-SAA2(X)-OH solutions were then extracted with dichloromethane, and the organic layer was dried over anhydrous magnesium sulfate. After the removal of dichloromethane, 416 mg Z-SAA1(X)-OH and 104 mg Z-SAA2(X)-OH were obtained as semi-solid.

Example 7

Synthesis of Val-Cit-APEA-AF

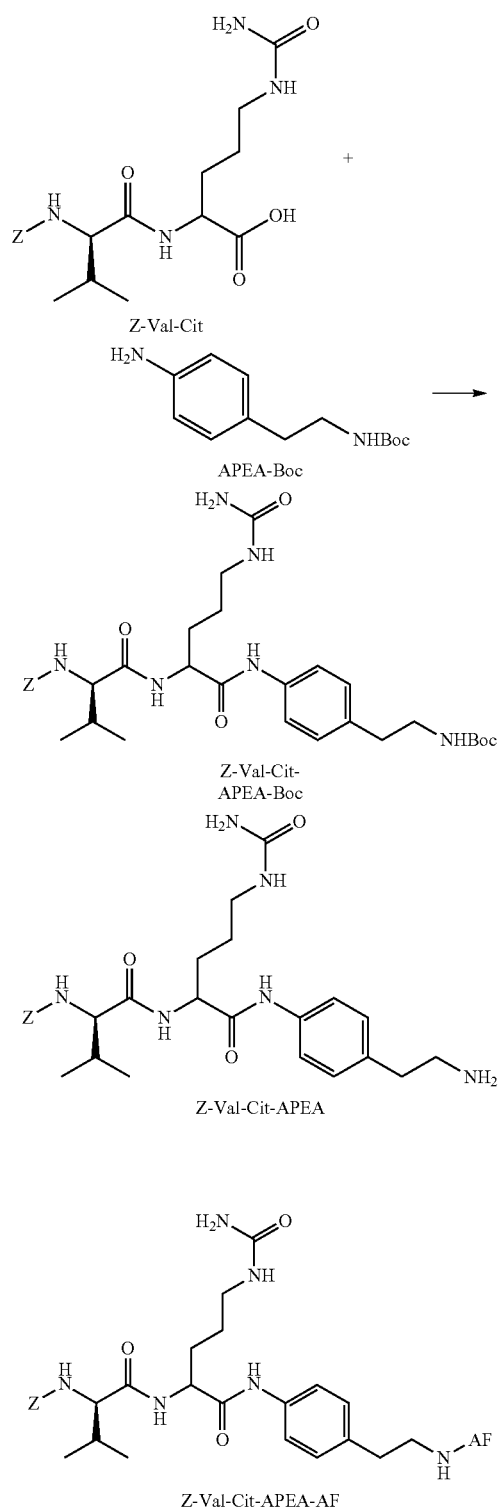

Z-Val-Cit (16.34 g, 40 mmol) and APEA-Boc (5.91 g, 25 mmol) were charged into a mixture of dichloromethane (1.5 L) and isopropanol (0.5 L) and stirred for 3 hours followed by adding EEDQ (9.89 g, 40 mmol). The turbid solution was stirred at room temperature. The undissolved Z-Val-Cit gradually disappeared and the solution gradually became turbid after one day due to the crashing out of the product. After 48 hours, the reaction was complete when checked with HPLC. The reaction mixture was evaporated under reduced pressure until a thick paste formed. The mixture was filtered off, and washed with isopropanol (400 mL, 2 times) and water (400 mL, 2 times). The solid product was suspended in water (800 mL) and submitted to freeze-drying to afford Z-Val-Cit-APEA-Boc as white powder (16.62 g. 61%).

Z-Val-Cit-APEA-Boc (18.80 g, 30 mmol) was charged into dichloromethane (200 mL) and then treated with trifluoroacetic acid (15 mL) overnight. The dichloromethane was evaporated under reduced pressure. Ethyl acetate (100 mL) was added to the oily residue and then evaporated under reduced pressure. This procedure was repeated two more times and then diethyl ether (300 mL) was added to the oily product to force the trifluoroacetate to crash out. The diethyl ether solution was dumped off. The solid product was stirred with ethyl acetate (500 mL) and then filtered. The solid product was suspended in sodium carbonate solution (1 M, 500 mL) and stirred until it well suspended. The mixture was centrifuged and then the supernatant solution was dumped off. The solid was re-suspended in water (500 mL) and centrifuged. This process was performed two times. The off white wet solid product was re-suspended in water (500 mL) and subjected to freeze-drying to afford Z-Val-Cit-APEA (9.87 g, 63%).

Auristatin F hydrochloride (626 mg, 0.8 mmol) was dissolved in a mixture of DMF (10 mL) and dichloromethane (10 mL). After Z-Val-Cit-APEA (506 mg, 0.96 mmol, 1.2 eq) and HATU (365 mg, 0.96 mmol, 1.2 eq) were added, the reaction mixture was immersed in an ice-bath followed by adding DIPEA (351 mg, 2.72 mmol, 3.4 eq). After 30 minutes, the ice-bath was removed and the reaction mixture was stirred at room temperature overnight. Then, the solvents were evaporated under reduced pressure and the crude product was purified by preparative HPLC (45% acetonitrile in water with 0.1% TFA; UV 210 nm; ODS-3 column 30*250 mm; flow rate 25 mL/min) to afford Z-Val-Cit-APEA-AF as white solid (574 mg; 51%). LC-MS: Z-Val-Cit-APEA-AF ($C_{67}H_{103}N_{11}O_{12}$) required [MH$^+$]=1254.8, found [MH$^+$]=1256.1.

Z-Val-Cit-APEA-AF (502 mg, 0.42 mmol) was dissolved in ethanol (30 mL) containing 2N hydrochloric acid (630 μL). After Pd/C (10%, 30 mg) was charged, the reaction mixture was applied a hydrogen balloon and stirred overnight. The catalyst Pd/C was filtered off through a pad of celite and then the filtrate was evaporated under reduced pressure. The product was mixed with water (10 mL) and submitted to freeze-drying to afford Val-Cit-APEA-AF as white solid (420 mg, 83%). LC-MS: Val-Cit-APEA-AF ($C_{59}H_{97}N_{11}O_{10}$) required [MH$^+$]=1121.5, found [MH$^+$]=1121.5.

<Linker-Toxin>

Example 8

Synthesis of MC-Val-Cit-APEA-AF

Val-Cit-APEA-Boc (65 mg) and MC-OPFP (50 mg) were dissolved in DMF (5 mL) and then DIPEA (0.023 mL) was added. After 5 hours, DMF and DIPEA were removed under reduced pressure. The crude product was then purified by preparative HPLC (50% acetonitrile in water with 0.1% TFA; UV 210 nm; ODS-3 column 50×500 mm; flow rate 80 mL/min; RT 13.60 min) to afford MC-Val-Cit-APEA-Boc as white solid (40 mg). LC-MS: 88 ($C_{34}H_{51}N_7O_8$) required [MH$^+$]=686.4, found [MH$^+$]=687.3.

MC-Val-Cit-APEA-Boc (40 mg) in DCM (5 mL) was treated with TFA (300 L) at room temperature. After 17 hours, DCM and TFA were removed under reduced pressure to afford MC-Val-Cit-APEA as light yellow solid (46 mg). LC-MS: MC-Val-Cit-APEA ($C_{29}H_{43}N_7O_6$) required [MH$^+$]= 586.3, found [MH$^+$]=586.7.

MC-Val-Cit-APEA (37 mg) and auristatin F (47 mg) were dissolved in a mixture of DCM and DMF (10:1, 3.7 mL). Then, HBTU (37 mg) and DIPEA (0.037 mL) were added. After 17 hours, DCM and DMF were removed under reduced pressure and the crude product was purified by preparative HPLC (40% acetonitrile in water with 0.1% TFA; UV 210 nm; ODS-3 column 30*250 mm; flow rate 25 mL/min; RT 14 min) to afford MC-Val-Cit-APEA-AF as white solid (9 mg). LC-MS: MC-Val-Cit-APEA-AF ($C_{70}H_{109}N_{11}O_{13}$) required [MH$^+$]=1312.8, found [MH$^+$]= 1315.2.

Example 9

Synthesis of MC-SAA1-Phe-Cit-APEA-AF

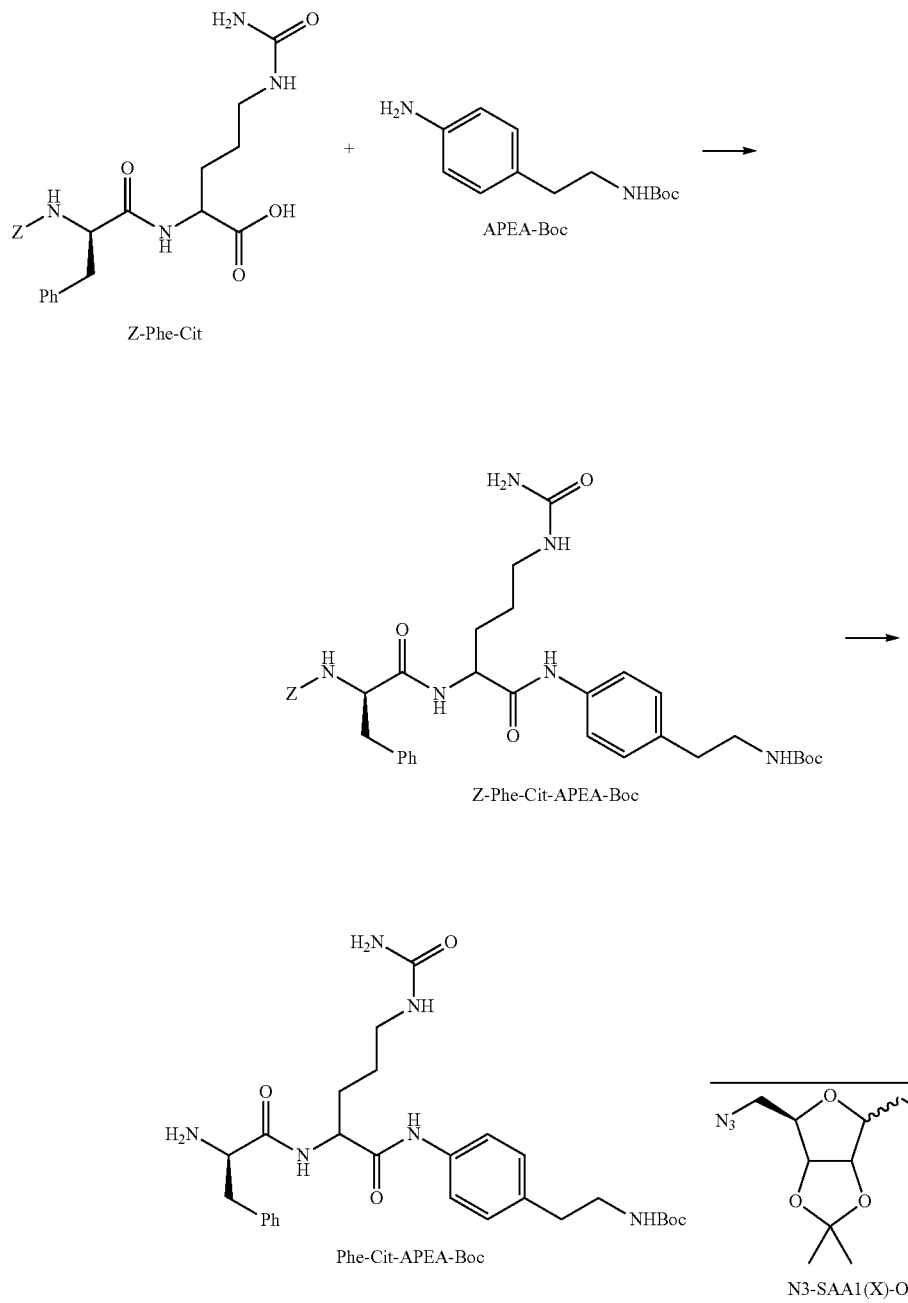

-continued
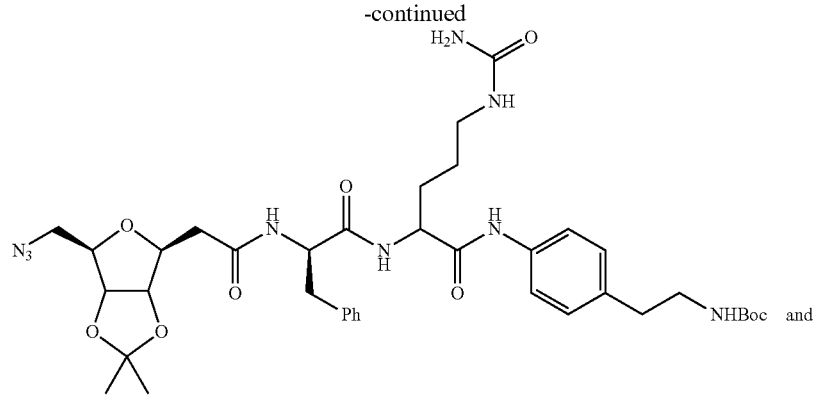
N3-SAA1(X)-Phe-Cit-APEA-Boc
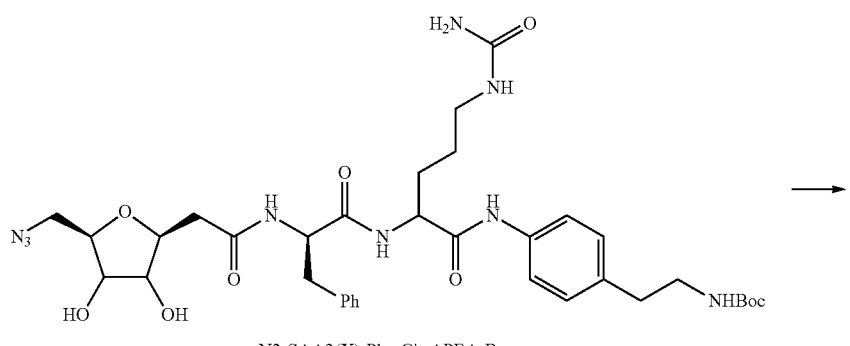
N3-SAA2(X)-Phe-Cit-APEA-Boc
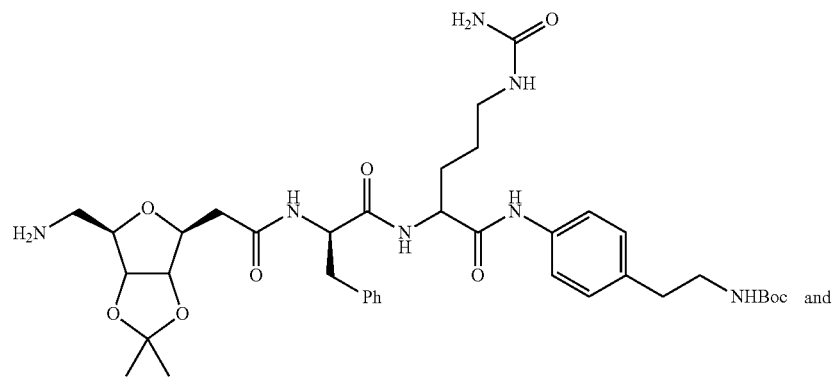
SAA1(X)-Phe-Cit-APEA-Boc and
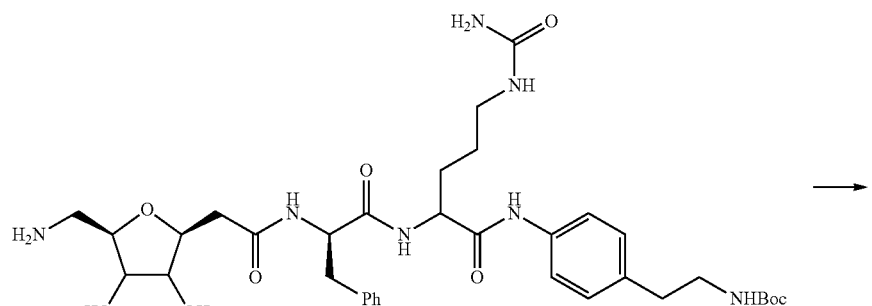
SAA1-Phe-Cit-APEA-Boc

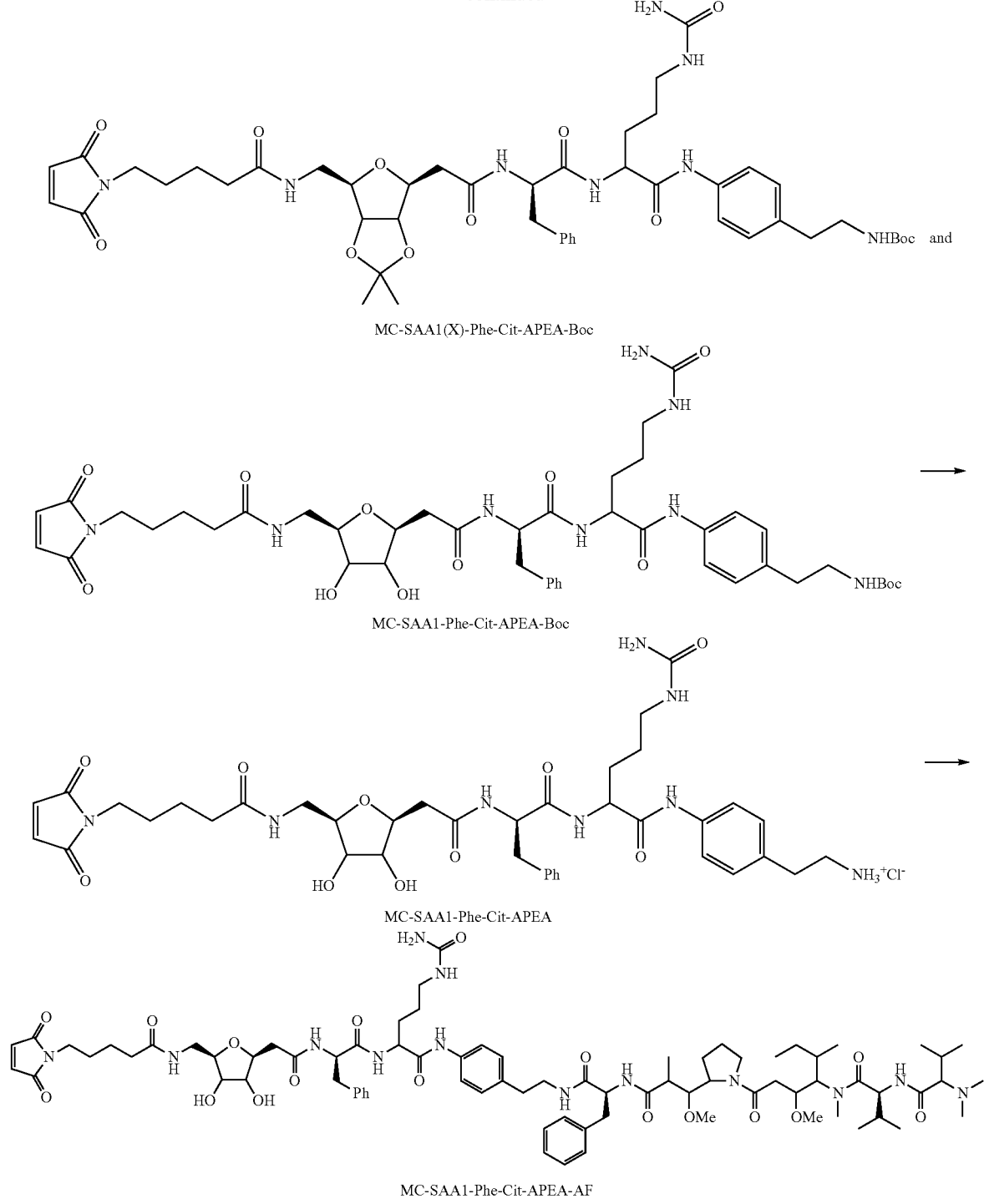

Z-Phe-Cit (9.13 g, 20 mmol) was charged into a mixture of dichloromethane (750 mL) and isopropanol (250 mL) and then stirred until the dipeptide was completely dissolved. Then, APEA-Boc (7.09 g, 30 mmol) and EEDQ (7.42 g, 30 mmol) were added and the mixture was stirred at room temperature for 3 days. The solvents were removed under reduced pressure and then diethyl ether (300 mL) was added to the residue. The mixture was filtered off and the crude product was re-suspended in diethyl ether (300 mL). This procedure was repeated 3 times. The collected solid product was finally dried under vacuum to afford Z-Phe-Cit-APEA-Boc (9.53 g, yield 70.6%). The product was characterized by PMR.

Z-Phe-Cit-APEA-Boc (2.02 g, 3 mmol) was dissolved in a mixture of THF (250 mL) and methanol (50 mL). After a catalytic amount of Pd/C (10%) was added, the reaction mixture was applied a hydrogen balloon and stirred overnight. After the catalyst was filtered off through a pad of celite, the filtrate was evaporated under reduced pressure to afford Phe-Cit-APEA-Boc as white solid (1.61 g, 99%).

To a solution of N3-SAA1(X)-OH (633 mg) and Phe-Cit-APEA-Boc (1.33 g) in a mixture of DCM and DMF (10:1, 110 mL) was added HBTU (1.118 g) and DIPEA (1.02 mL). After 17 hours, DCM was removed under reduced pressure. Water and diethyl ether were added to the remaining crude DMF solution and a beige solid was obtained after filtration. The solid was washed with concentrated aqueous citric acid solution several times to remove most of the HOBt and DMF. N3-SAA1(X)-Phe-Cit-APEA-Boc was finally purified by preparative HPLC (50% acetonitrile in water with 0.1% TFA; UV 210 nm; ODS-3 column 30×250 mm). Acetonitrile was evaporated under reduced pressure and the remaining aqueous solution was submitted to freeze-drying. A white solid was obtained (1 g) consisting of N3-SAA1(X)-Phe-Cit-APEA-Boc and N3-SAA1-Phe-Cit-APEA-Boc. LC-MS: N3-SAA1(X)-Phe-Cit-APEA-Boc ($C_{38}H_{53}N_9O_9$) required [MH$^+$]=780.9, found [MH$^+$]=781.8; N3-SAA1-Phe-Cit-APEA-Boc ($C_{35}H_{49}N_9O_9$) required [MH$^+$]=740.8, found [MH$^+$]=741.7.

The mixture of N3-SAA1(X)-Phe-Cit-APEA-Boc and N3-SAA1-Phe-Cit-APEA-Boc (100 mg) was dissolved in methanol (50 mL). After a catalytic amount of Pd/C (10%) was added, the reaction mixture was applied a hydrogen balloon and stirred overnight. After the catalyst was filtered off through a pad of celite, the methanol was removed under reduced pressure and a white solid was obtained (78 mg) consisting of SAA1(X)-Phe-Cit-APEA-Boc and SAA1-Phe-Cit-APEA-Boc.

To a solution of SAA1(X)-Phe-Cit-APEA-Boc and SAA1-Phe-Cit-APEA-Boc (210 mg) in MeOH (50 mL) was added MC-OPFP (103 mg) followed by the addition of DIPEA (0.047 mL). After 17 hours, the reaction mixture was concentrated. The crude product was purified by preparative HPLC (50% acetonitrile in water with 0.1% TFA; UV 210 nm; ODS-3 column 30×500 mm; flow rate 40 mL/min) to afford solution of MC-SAA1(X)-Phe-Cit-APEA-Boc and MC-SAA1-Phe-Cit-APEA-Boc.

The solution of MC-SAA1(X)-Phe-Cit-APEA-Boc and MC-SAA1-Phe-Cit-APEA-Boc was treated with concentrated hydrochloric acid (10 eq.). The reaction was monitored by analytical HPLC until the hydrolysis was complete. Acetonitrile was removed under reduced pressure and solid MC-SAA1-Phe-Cit-APEA was obtained after freeze-drying of the aqueous solution. LC-MS: MC-SAA1-Phe-Cit-APEA ($C_{40}H_{54}N_8O_{10}$) required [MH$^+$]=807.4, found [MH$^+$]=809.1.

MC-SAA1-Phe-Cit-APEA (110 mg) was dissolved in a mixture of DCM and DMF (10:1, 10 mL) and then auristatin F (93 mg), HBTU (55 mg), and DIPEA (0.077 mL) were added respectively. After 17 hours, DCM, DMF and DIPEA were removed under reduced pressure. The crude product was purified by preparative HPLC (35% acetonitrile in water with 0.1% TFA; UV 210 nm; ODS-3 column 30×250 mm; flow rate 40 mL/min). Acetonitrile in the target fraction was removed under reduced pressure and the remaining aqueous solution was submitted to freeze-drying to afford MHT-47 as white solid (20 mg). LC-MS: MC-SAA1-Phe-Cit-APEA-AF ($C_{80}H_{119}N_{13}O_{17}$) required [MH$^+$]=1534.9, found [MH$^+$]=1538.0.

Example 10

Synthesis of MC-SAA1-Val-Cit-APEA-AF

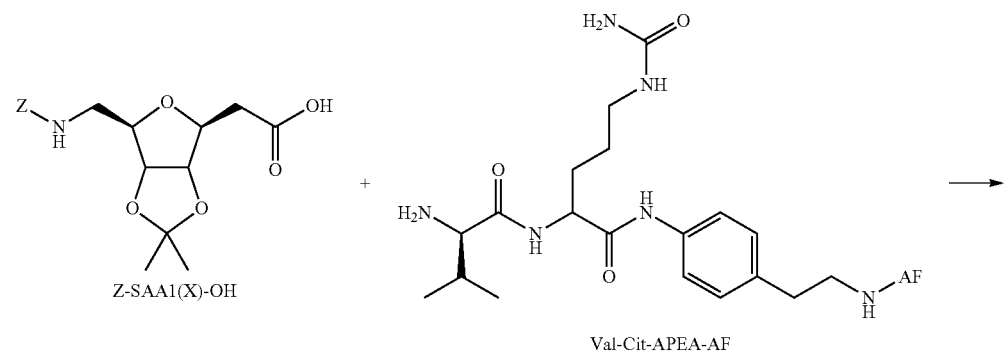

Z-SAA1(X)-OH + Val-Cit-APEA-AF

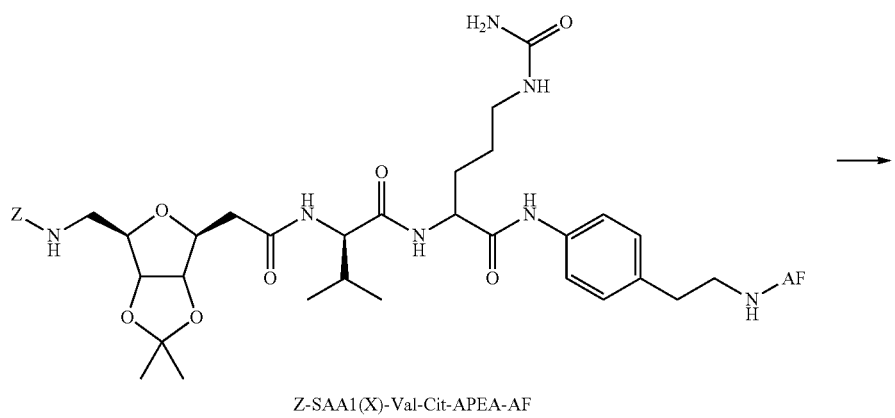

Z-SAA1(X)-Val-Cit-APEA-AF

-continued

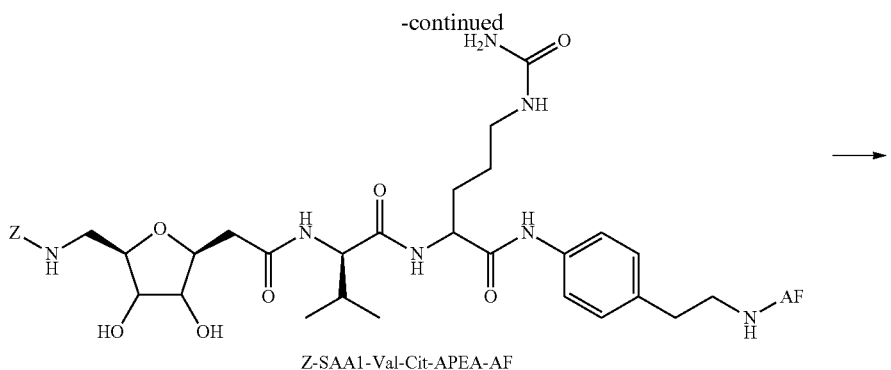
Z-SAA1-Val-Cit-APEA-AF

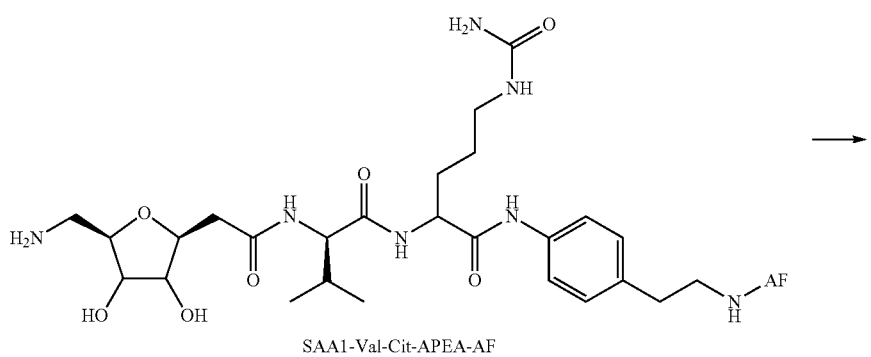
SAA1-Val-Cit-APEA-AF

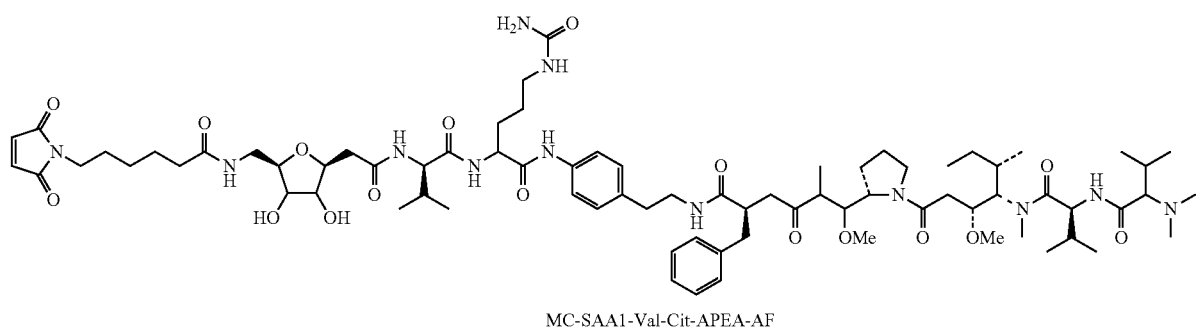
MC-SAA1-Val-Cit-APEA-AF

To a solution of Z-SAA1(X)-OH (26.1 mg) and Val-Cit-APEA-AF (80 mg) in a mixture of DCM and DMF (10:1, 4.4 mL) was added HBTU (32.5 mg) and DIPEA (0.029 mL) respectively. After 18 hours, the solvents were removed under reduced pressure and the crude product was purified by preparative HPLC (45% acetonitrile in water with 0.1% TFA; UV 210 nm; ODS-3 column 30×500 mm; flow rate 65 mL/min; RT 11 min). After the removal of acetonitrile, the aqueous solution was left in a fridge overnight until Z-SAA1(X)-Val-Cit-APEA-AF was completely transformed into Z-SAA1-Val-Cit-APEA-AF. The aqueous solution was then submitted to freeze-drying to afford Z-SAA1-Val-Cit-APEA-AF as white solid (63 mg, 63% yield over two steps).

Z-SAA1-Val-Cit-APEA-AF (63 mg) was dissolved in methanol (5 mL) followed by adding Pd/C catalyst. The reaction mixture was then applied a hydrogen balloon and stirred for 3 hours. The Pd/C was filtered off through a pad of celite and then the filtrate was evaporated under reduced pressure to afford SAA1-Val-Cit-APEA-AF as white solid (52.5 mg).

To a solution of SAA1-Val-Cit-APEA-AF (40 mg) and MC-OPFP (11.6 mg) in methanol (4 mL) was added DIPEA (0.0056 mL). The reaction was stirred overnight and then evaporated under reduced pressure. The crude product was purified by preparative HPLC (35% acetonitrile in water with 0.1% TFA; UV 210 nm; ODS-3 column 30×500 mm; flow rate 70 mL/min; RT 18 min) to afford MC-SAA1-Val-Cit-APEA-AF (MHT-71) as white solid (27 mg; 47%). LC-MS: MC-SAA1-Val-Cit-APEA-AF ($C_{76}H_{120}N_{13}O_{17}$) required [MH$^+$]=1486.9, found [MH$^+$]=1487.2.

Example 11

Synthesis of Cl2MC-SAA1-Val-Cit-APEA-AF

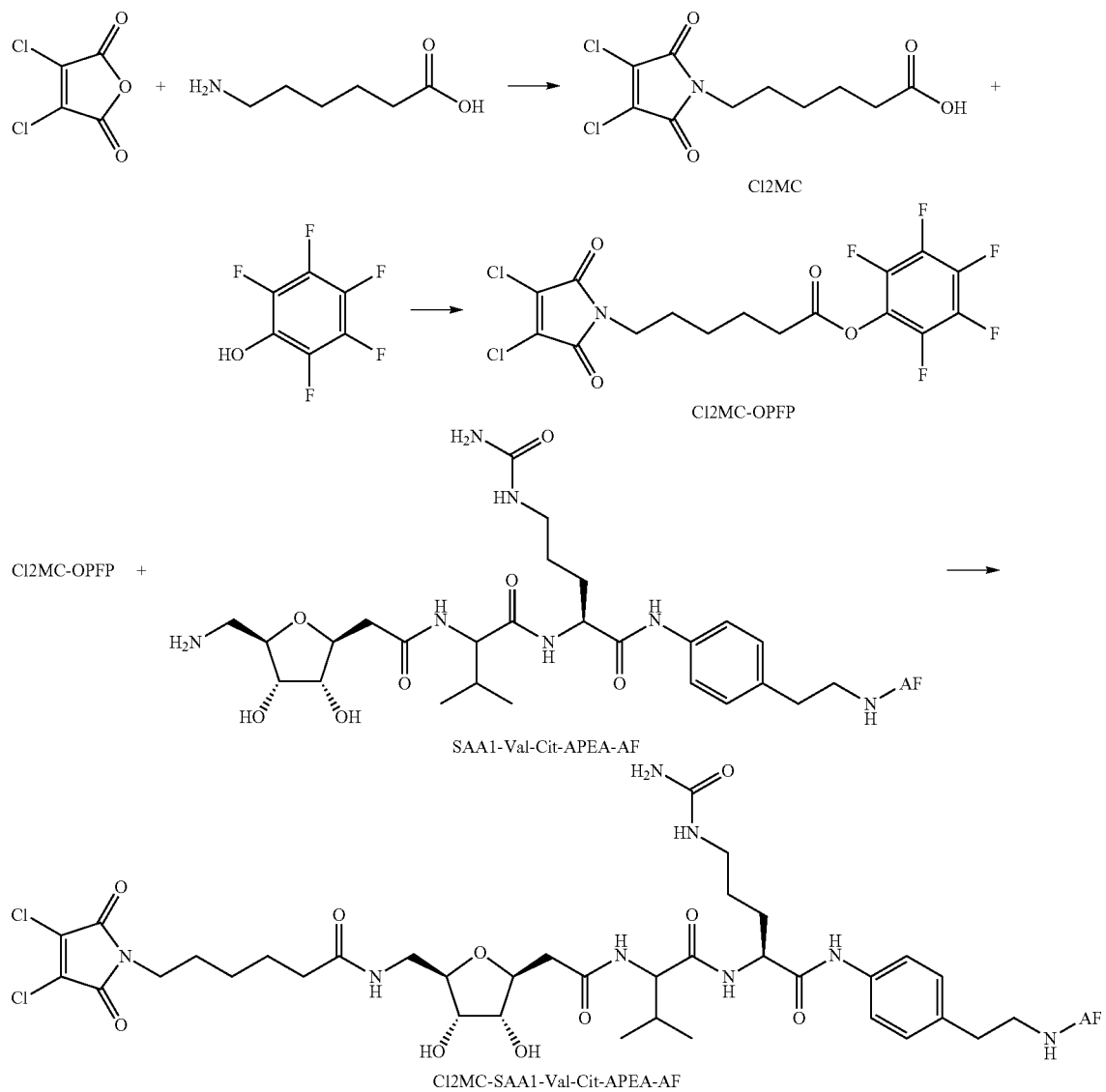

3,4-Dichloro-furan-2,5-dione (10.34 g, 0.0619 mol) was mixed with 6-aminocaproic acid (8.13 g, 0.0619) in glacial acetic acid (50 mL). The mixture was reflux for 12 hours. After the solvent was evaporated under reduced pressure, the residue was purified by flash column chromatography (EA/Hexane=2/3) to afford Cl2MC as white powder (12.48 g, 72%). LC-MS: Cl2MC ($C_{10}H_{11}Cl_2NO_4$) required [M-CO2]+=235.0, found [M-CO2]+=235.0.

To a solution of Cl2MC (1.06 g, 3.8 mmol) and pentafluorophenol (0.84 g, 4.5 mmol) in dichloromethane (25 mL) was added DCC (0.83 g, 4.0 mmol). The reaction mixture was stirred at room temperature for 12 hours and then filtered to remove the insoluble DCU. The reaction mixture was evaporated under reduced pressure until the volume reached about 10 ml. The solution was stored in a fridge at 4 degrees for 2 hours. The insoluble material was filtered off and the filtrate was purified by flash column chromatography (EA/Hexane=1/30 to 1/20) to afford Cl2MC-OPFP as white solids (1.39 g, 82%).

To a solution of SAA1-Val-Cit-APEA-AF (5.0 mg, 0.0039 mmol) and Cl2MC-OPFP (2.0 mg, 0.0046 mmol) in DMF (1 mL) was added DIPEA (0.002 mL, 0.0116 mmol). The mixture was stirred at room temperature for 1 hour and then evaporated under reduced pressure. The crude product was purified by preparative HPLC (35% acetonitrile in water with 0.1% TFA; UV 210 nm; ODS-3 column 30×250 mm; flow rate 25 mL/min) to afford Cl2MC-SAA1-Val-Cit-APEA-AF as white solid (3.0 mg; 50%). LC-MS: Cl2MC-SAA1-Val-Cit-APEA-AF ($C_{76}H_{117}Cl_2N_{13}O_{17}$) required [M+2H]2+=777.9, found [M+2H]2+=779.4.

Example 12
Synthesis of Br2MC-SAA1-Val-Cit-APEA-AF
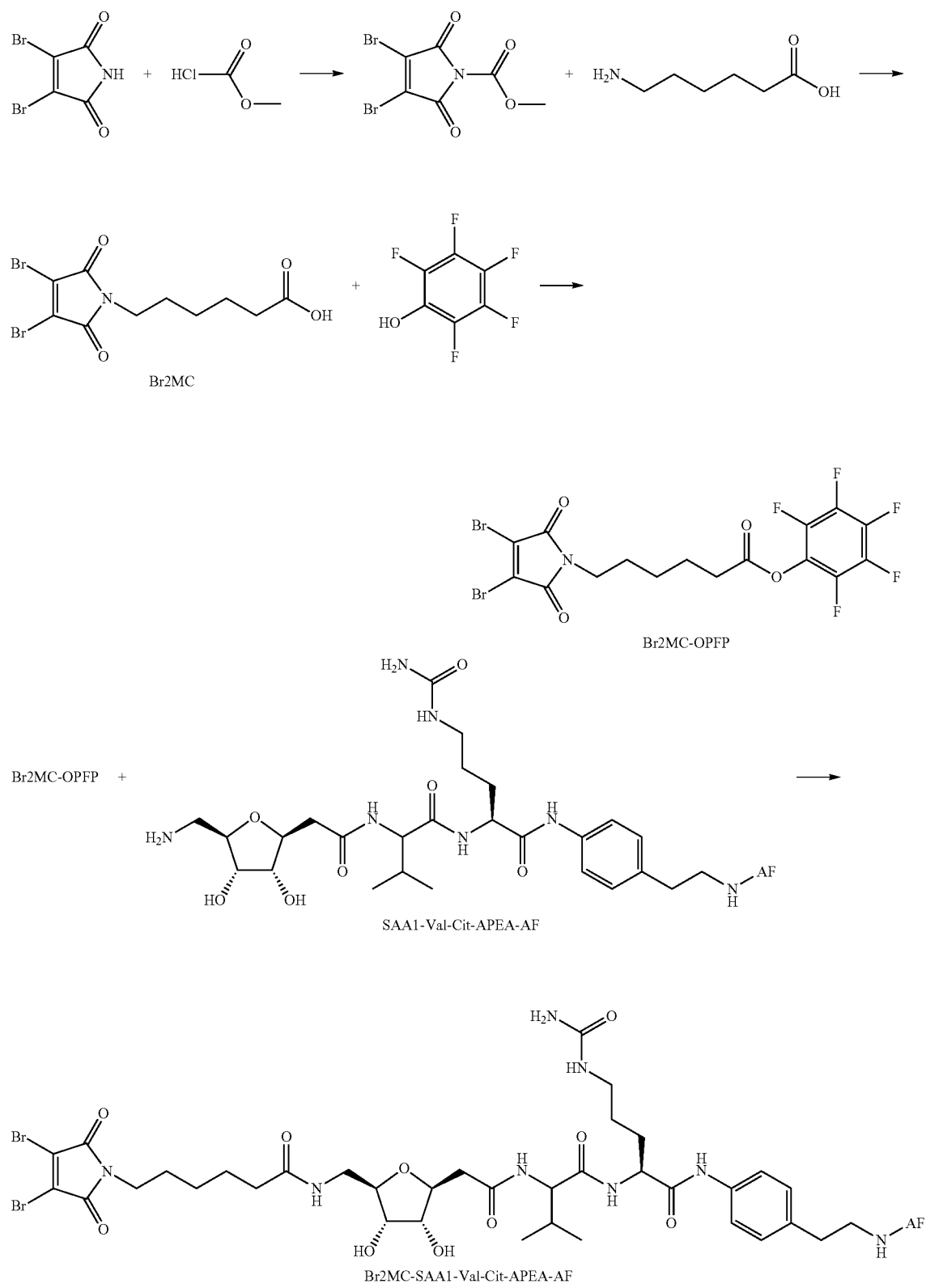

To a solution of 3,4-dibromo-pyrrol-2,5-dione (1.00 g, 3.92 mmol) and N-methylmorpholine (0.431 mL, 3.92 mmol) in THF (35 mL) was added methyl chloroformate (0.303 mL, 3.92 mmol). The reaction mixture was stirred at room temperature for 3 hours. Then, dichloromethane (40 mL) was added and the organic phase was washed with water (40 mL, 3 times). The organic solution was dried over anhydrous magnesium sulfate and then evaporated under reduced pressure to afford 3,4-dibromo-2,5-dioxo-2,5-dihydro-pyrrole-1-carboxylic acid methyl ester as pink powder (1.13 g, 93%).

6-Aminocaproic acid (476.0 mg, 3.6 mmol) was dissolved in a mixture of acetonitrile and water (3:2, 50 mL). The solution was cooled in an ice-bath and then treated with saturated sodium bicarbonate solution (1 mL), followed by 3,4-dibromo-2,5-dioxo-2,5-dihydro-pyrrole-1-carboxylic acid methyl ester (1.13 g, 3.6 mmol). The mixture was stirred at room temperature for 12 hours. The pH was then adjusted to 3-4 with citric acid solution and the mixture was evaporated under reduced pressure to remove acetonitrile. The residue was purified by flash column chromatography (EA/Hexane, 2/3) to afford Br2MC as white powder (1.33 g, 99%). LC-MS: Br2MC ($C_{10}H_{11}Br_2NO_4$) required [M+H]+=369.9, found [M+H]+=371.0.

To a solution of Br2MC (1.33 g, 3.86 mmol) and pentafluorophenol (0.80 g, 4.3 mmol) in dichloromethane (40 mL) was added DCC (0.79 g, 3.8 mmol). The reaction mixture was stirred at room temperature for 12 hours and then filtered to remove the insoluble DCU. The reaction mixture was evaporated under reduced pressure until the volume reached about 10 ml. The solution was stored in a fridge at 4 degrees for 2 hours. The insoluble material was filtered off and the filtrate was purified by flash column chromatography (EA/Hexane=1/30 to 1/20) to afford Br2MC-OPFP as white solids (1.50 g, 78%).

To a solution of SAA1-Val-Cit-APEA-AF (8.9 mg, 0.0069 mmol) and Br2MC-OPFP (4.5 mg, 0.0083 mmol) in DMF (1 mL) was added DIPEA (0.0036 mL, 0.0206 mmol). The mixture was stirred at room temperature for 1 hour and then evaporated under reduced pressure. The crude product was purified by preparative HPLC (35% acetonitrile in water with 0.1% TFA; UV 210 nm; ODS-3 column 30×250 mm; flow rate 25 mL/min) to afford Br2MC-SAA1-Val-Cit-APEA-AF as white solid (5.6 mg; 50%). LC-MS: Br2MC-SAA1-Val-Cit-APEA-AF ($C_{76}H_{117}Br_2N_{13}O_{17}$) required [M+H]+=1644.7, found [M+H]+=1645.1.

Example 13

Synthesis of MC-SAA1-Val-Cit-APEA(COOMe)-AF

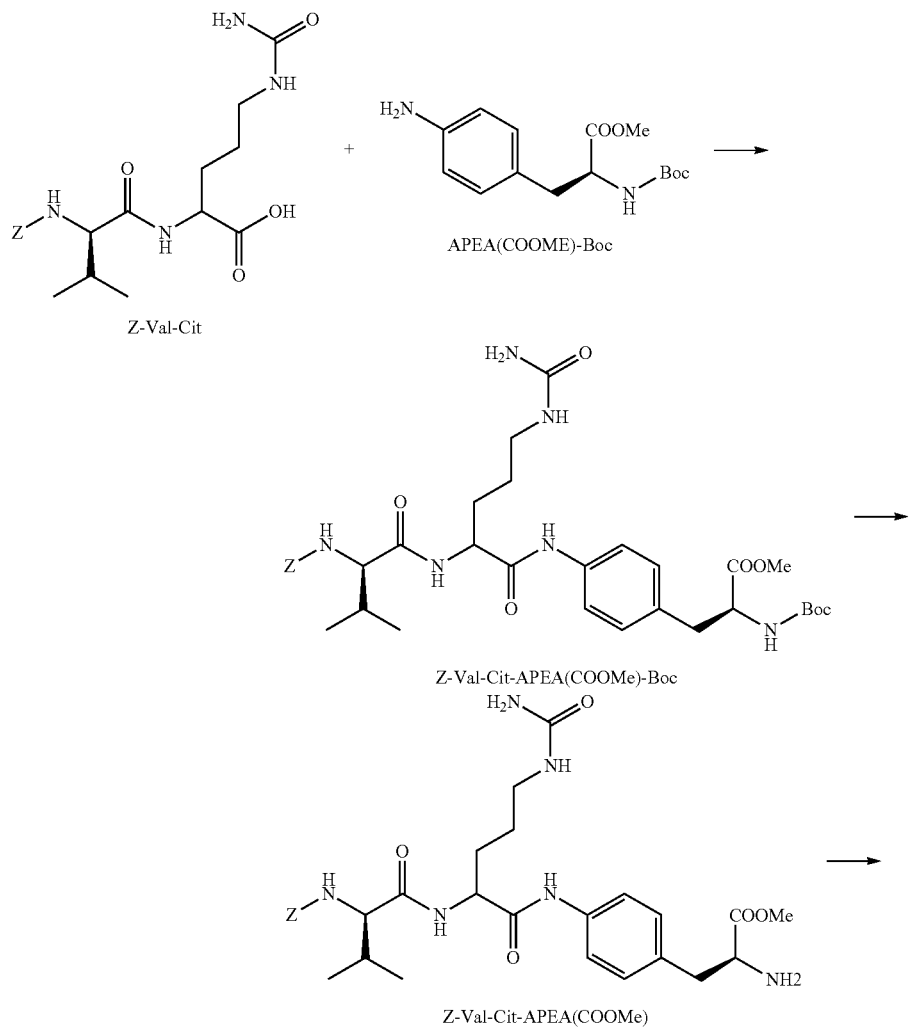

-continued
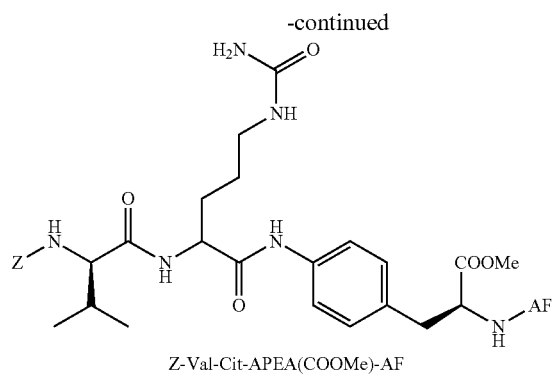
Z-Val-Cit-APEA(COOMe)-AF
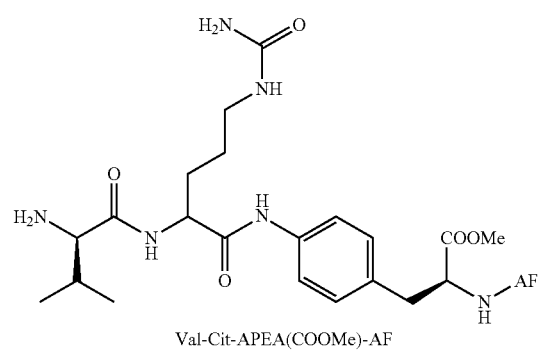
Val-Cit-APEA(COOMe)-AF
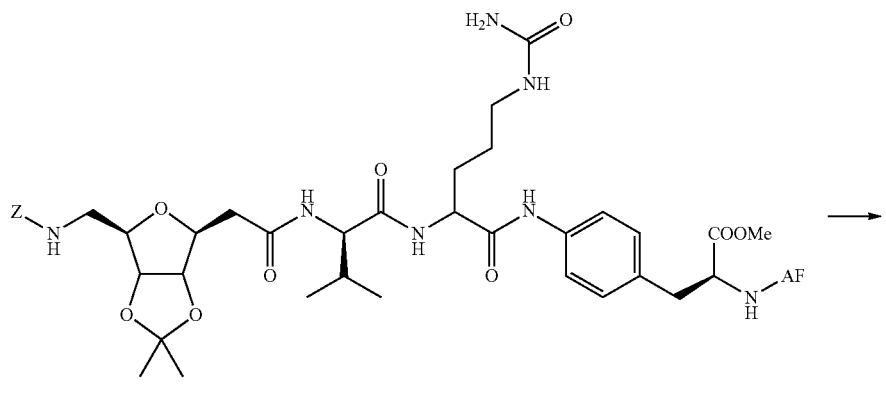
Z-SAA1(X)-Val-Cit-APEA(COOMe)-AF
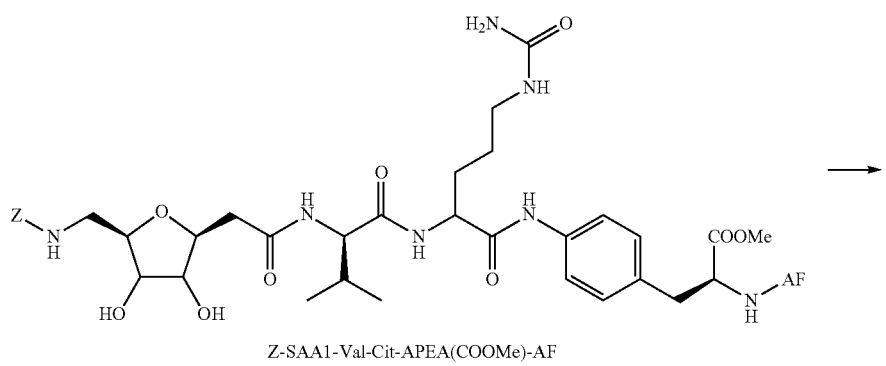
Z-SAA1-Val-Cit-APEA(COOMe)-AF

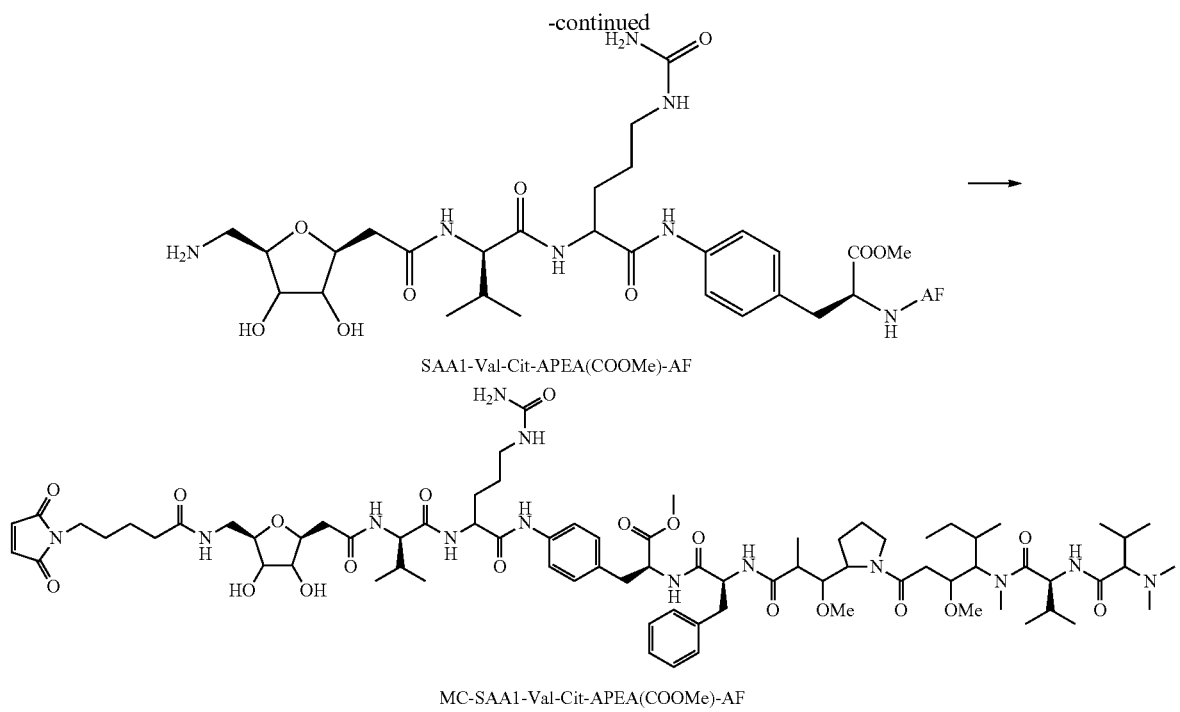

SAA1-Val-Cit-APEA(COOMe)-AF

MC-SAA1-Val-Cit-APEA(COOMe)-AF

Z-Val-Cit-OH (3.24 g, 7.93 mmol) was added into a mixture of dichloromethane and methanol (3:1, 80 mL). After APEA(COOMe)-Boc (2.8 g, 9.52 mmol) was added, the coupling reagent EEDQ (2.47 g, 9.52 mmol) was charged. The turbid solution was stirred at room temperature. The undissolved Z-Val-Cit was gradually disappeared and the solution gradually became clear. After 48 hours, the reaction was complete when checked with HPLC. The reaction mixture was evaporated under reduced pressure until a thick paste formed. The mixture was filtered off, washed with n-hexane (50 mL, 2 times), water (50 mL, 2 times) and diethyl ether (50 mL, 2 times). The solid product was finally dried under vacuum to afford Z-Val-Cit-APEA (COOMe)-Boc as brown powder (75.0 mg, 1.4%).

Z-Val-Cit-APEA(COOMe)-Boc (75.0 mg, 0.11 mmol) was added into dichloromethane (8 mL) and then treated with trifluoroacetic acid (0.09 mL) at room temperature. After 4 hours, the solvent was evaporated under reduced pressure. The residue was mixed with water (10 mL) and submitted to freeze-drying to afford Z-Val-Cit-APEA (COOMe) as white powder (96.0 mg).

Auristatin F (80.0 mg, 0.102 mmol) was dissolved in small amount of DMF (1 mL) and then diluted with DCM (10 mL). The solution was immersed in an ice-bath and then Z-Val-Cit-APEA(COOMe) (71.4 mg, 0.102 mmol) and HATU (43.0 mg, 0.113 mmol) were charged. After DIPEA (0.071 mL) was added, the ice-bath was removed. After the mixture was stirred at room temperature for 4 hours, the solvents were evaporated under reduced pressure and the residue was purified by preparative HPLC (43% acetonitrile in water with 0.1% TFA; UV 210 nm; ODS-3 column 30*250 mm; flow rate 24 mL/min) to afford Z-Val-Cit-APEA(COOMe)-AF as white solid (82.0 mg, 61%).

Z-Val-Cit-APEA(COOMe)-AF (82.0 mg, 0.062 mmol) was dissolved in ethanol (10 mL) containing hydrochloric acid (0.24 mmol). After Pd/C (10%, 10 mg) was charged, the reaction mixture was applied a hydrogen balloon and stirred overnight. The catalyst Pd/C was filtered off through a pad of celite and then the filtrate was evaporated under reduced pressure. The residue was mixed with water (10 mL) and submitted to freeze-drying to afford Val-Cit-APEA (COOMe)-AF as white powder (72.8 mg, 96%). LC-MS: Val-Cit-APEA(COOMe)-AF ($C_{61}H_{99}N_{11}O_{12}$) required [MH$^+$]=1178.8, found [MH$^+$]=1179.7.

Z-SAA1(X)-OH (22.0 mg, 0.06 mmol) was dissolved in dichloromethane (10 mL). After HATU (25.3 mg, 0.066 mmol) was added, the reaction mixture was immersed in an ice-bath followed by adding DIPEA (0.032 mL, 0.06 mmol). After 10 minutes, the ice-bath was removed and a solution of Val-Cit-APEA(COOMe)-AF (72.8 mg, 0.06 mmol) in DMF (3 mL) was added to the reaction mixture at room temperature. After 3 hours, the solvents were evaporated under reduced pressure and the crude product was purified by preparative HPLC (45% acetonitrile in water with 0.1% TFA; UV 210 nm; ODS-3 column 30×250 mm; flow rate 24 mL/min). After the removal of acetonitrile, the aqueous solution was left at room temperature overnight to allow the Z-SAA1(X)-Val-Cit-APEA(COOMe)-AF completely hydrolyzed. The aqueous solution was then submitted to freeze-drying to afford Z-SAA1-Val-Cit-APEA(COOMe)-AF as white solid (43.5 mg, 49% yield over two steps). LC-MS: Z-SAA1-Val-Cit-APEA(COOMe)-AF ($C_{79}H_{120}N_{12}O_{18}$) required [MH$^+$]=1525.9, found [MH$^+$]= 1526.8.

Z-SAA1-Val-Cit-APEA(COOMe)-AF (43.5 mg, 0.029 mmol) was dissolved in ethanol (5 mL) containing hydrochloric acid (0.06 mmol). After Pd/C (10%, 4.7 mg) was charged, the reaction mixture was applied a hydrogen balloon and stirred overnight. The catalyst Pd/C was filtered off through a pad of celite and then the filtrate was evaporated under reduced pressure. The residue was mixed with water (5 mL) and submitted to freeze-drying to afford SAA1-Val-Cit-APEA(COOMe)-AF as white powder (38.4 mg, 94%).

To a solution of SAA1-Val-Cit-APEA(COOMe)-AF (15.0 mg, 0.011 mmol) and MC-OPFP (4.5 mg, 0.012 mmol) in DMF (4 mL) was added DIPEA (0.004 mL). The mixture was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA1-Val-Cit-APEA(COOMe)-AF as white solid (10.0 mg; 60%). LC-MS: MC-SAA1-Val-Cit-APEA(COOMe)-AF ($C_{78}H_{121}N_{13}O_{19}$) required [MH$^+$]=1544.9, found [MH$^+$]=1545.8.

Example 14

Synthesis of MC-SAA1-SAA1-Val-Cit-APEA-AF

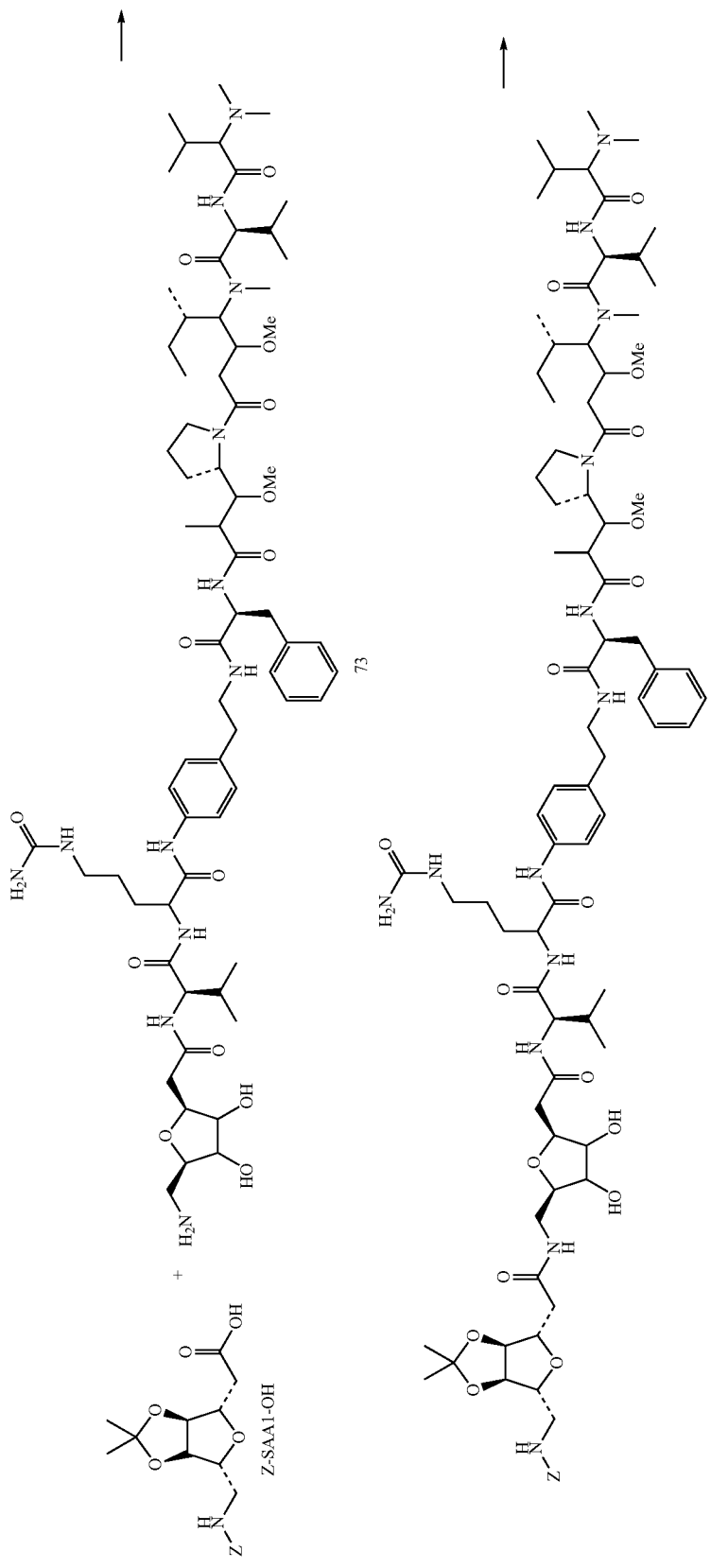

-continued
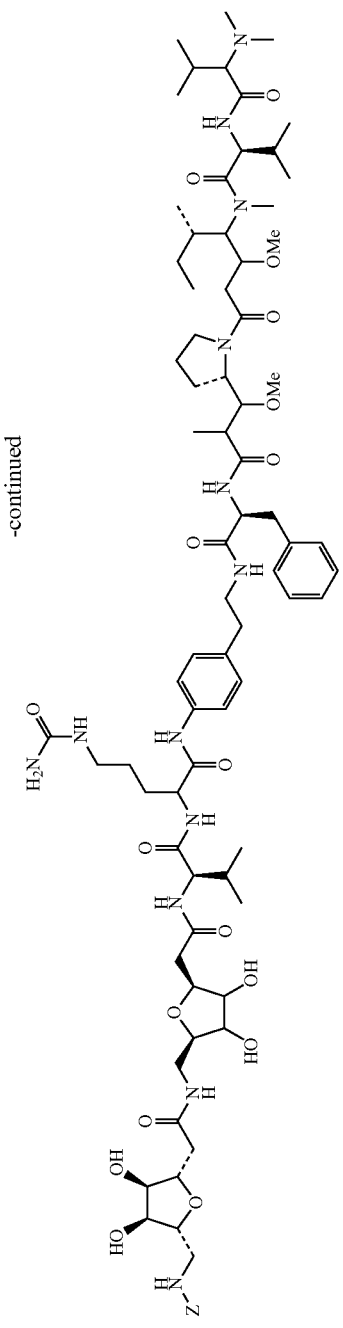
Z-SAA1-SAA1-Val-Cit-APEA-AF [WHY-43-OH]
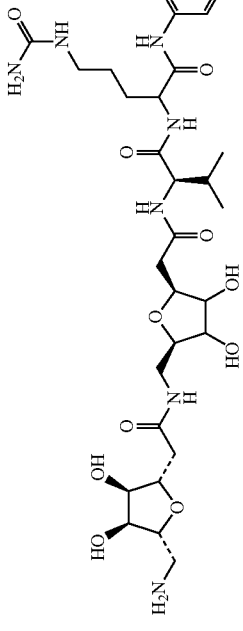
SAA1-SAA1-Val-Cit-APEA-AF [WHY-44]
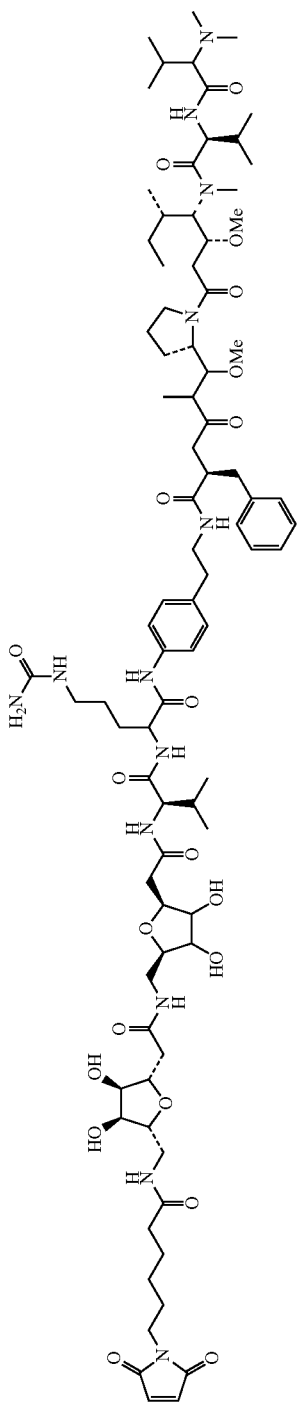
MC-SAA1-SAA1-Val-Cit-APEA-AF [WHY-46]

Z-SAA1(X)-OH (28.0 mg, 0.076 mmol) was dissolved in dichloromethane (1 mL). After HATU (23.4 mg, 0.0.061 mmol) was added, the reaction mixture was immersed in an ice-bath followed by adding DIPEA (7.9 mg, 0.061 mmol). After 10 minutes, the ice-bath was removed and a solution of SAA1-Val-Cit-APEA-AF (70.0 mg, 0.051 mmol) in DMF (3 mL) was added to the reaction mixture at room temperature. After 1 hour, the solvents were evaporated under reduced pressure and the crude product was purified by preparative HPLC (39% acetonitrile in water with 0.1% TFA; UV 210 nm; ODS-3 column 30×250 mm; flow rate 25 mL/min). After the removal of acetonitrile, the aqueous solution was left at room temperature overnight to allow the Z-SAA1(X)-SAA1-Val-Cit-APEA-AF to completely hydrolyzed. The aqueous solution was then submitted to freeze-drying to afford Z-SAA1-SAA1-Val-Cit-APEA-AF as white solid (64 mg, 78% yield over two steps). LC-MS: Z-SAA1-SAA1-Val-Cit-APEA-AF ($C_{81}H_{125}N_{13}O_{20}$) required $[MH^+]$= 1602.0, found $[MH^+]$=1601.5.

Z-SAA1-SAA1-Val-Cit-APEA-AF (64.0 mg, 0.042 mmol) was dissolved in ethanol (20 mL) containing hydrochloric acid (0.136 mmol). After Pd/C (10%, 6.5 mg) was charged, the reaction mixture was applied a hydrogen balloon and stirred overnight. The catalyst Pd/C was filtered off through a pad of celite and then the filtrate was evaporated under reduced pressure. The product was mixed with water (10 mL) and submitted to freeze-drying to afford SAA1-SAA1-Val-Cit-APEA-AF as white solid (60.0 mg, 97%). LC-MS: SAA1-SAA1-Val-Cit-APEA-AF ($C_{73}H_{119}N_{13}O_{18}$) required $[MH^+]$=1466.9, found $[MH^+]$=1467.5.

SAA1-SAA1-Val-Cit-APEA-AF (30.0 mg, 0.019 mmol) and DIPEA (7.4 mg, 0.057 mmol) were dissolved in DMF (2 mL). After the reaction mixture was immersed in an ice-bath, MC-OPFP (9.0 mg, 0.023 mmol) was added. After 10 minutes, the ice-bath was removed and the mixture was stirred at room temperature for 1 hour. The solvent was evaporated under reduced pressure and the crude product was purified by preparative HPLC (33% acetonitrile in water with 0.1% TFA; UV 210 nm; ODS-3 column 30×250 mm; flow rate 25 mL/min) to afford MC-SAA1-SAA1-Val-Cit-APEA-AF as white solid (18.5 mg, 53%). LC-MS: MC-SAA1-SAA1-Val-Cit-APEA-AF ($C_{83}H_{130}N_{14}O_{21}$) required $[MH^+]$=1660.0, found $[MH^+]$=1660.7.

Example 15

Synthesis of
Cl2MC-SAA1-SAA1-Val-Cit-APEA-AF

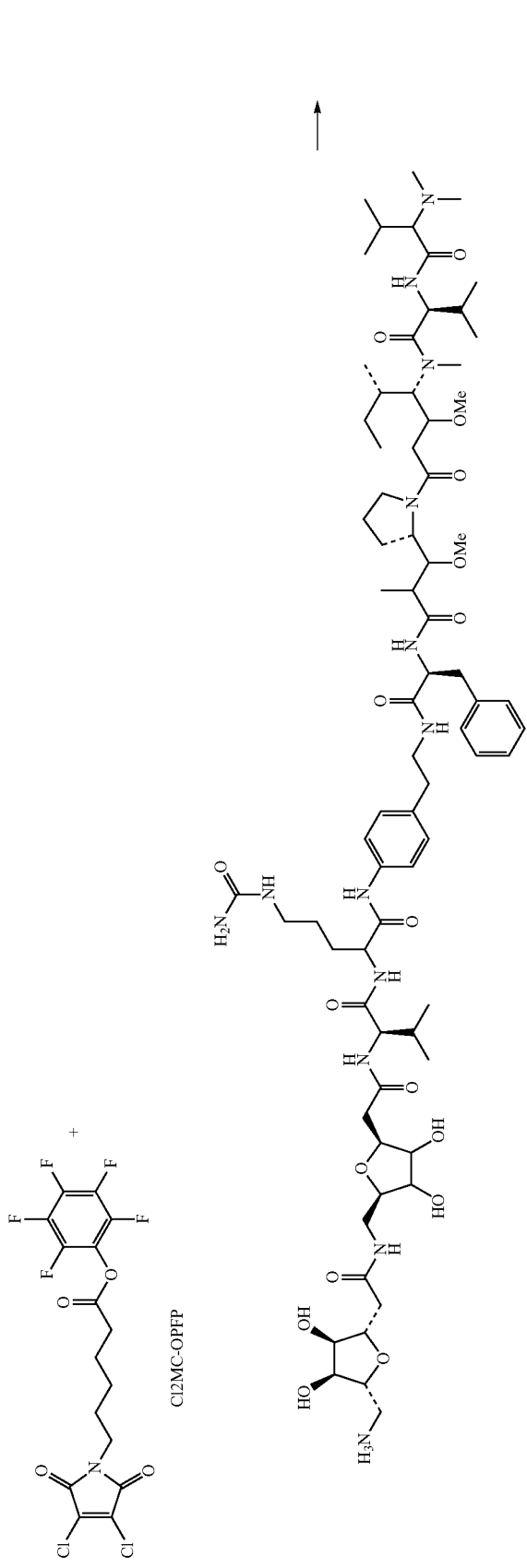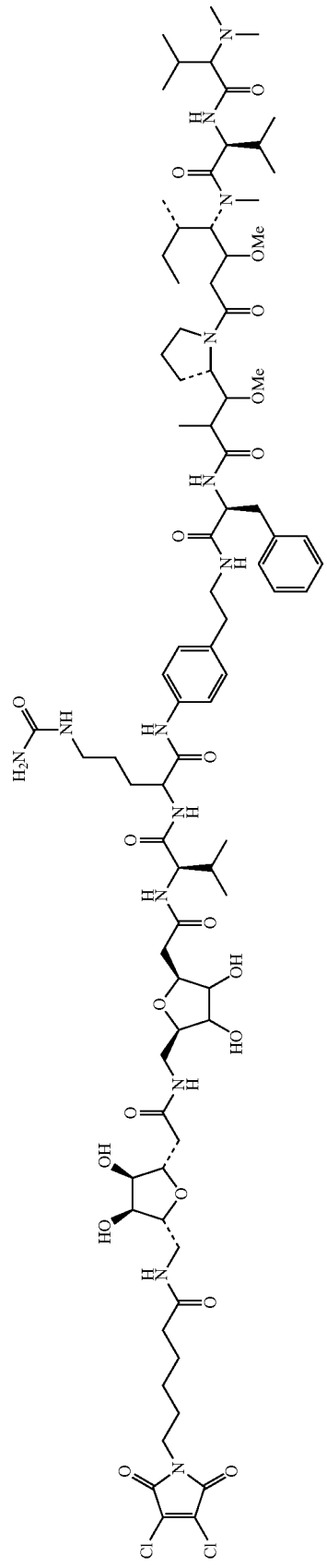

SAA1-SAA1-Val-Cit-APEA-AF (3.0 mg, 0.00065 mmol) and DIPEA (0.003 mL, 0.0164 mmol) were dissolved in DMF (1 mL). After the reaction mixture was immersed in an ice-bath, Cl2MC-OPFP (3.0 mg, 0.0065 mmol) was added. After 10 minutes, the ice-bath was removed and the mixture was stirred at room temperature for 1 hour. The solvent was evaporated under reduced pressure and the crude product was purified by preparative HPLC (33% acetonitrile in water with 0.1% TFA; UV 210 nm; ODS-3 column 30×250 mm; flow rate 25 mL/min) to afford Cl2MC-SAA1-SAA1-Val-Cit-APEA-AF as white solid (2.8 mg, 30%). LC-MS: Cl2MC-SAA1-SAA1-Val-Cit-APEA-AF ($C_{83}H_{128}Cl_2N_{14}O_{21}$) required [M+H]+=1727.9, found [M+H]+=1729.6.

Example 16

Synthesis of
Cl2MC-SAA1-SAA1-SAA1-Val-Cit-APEA-AF

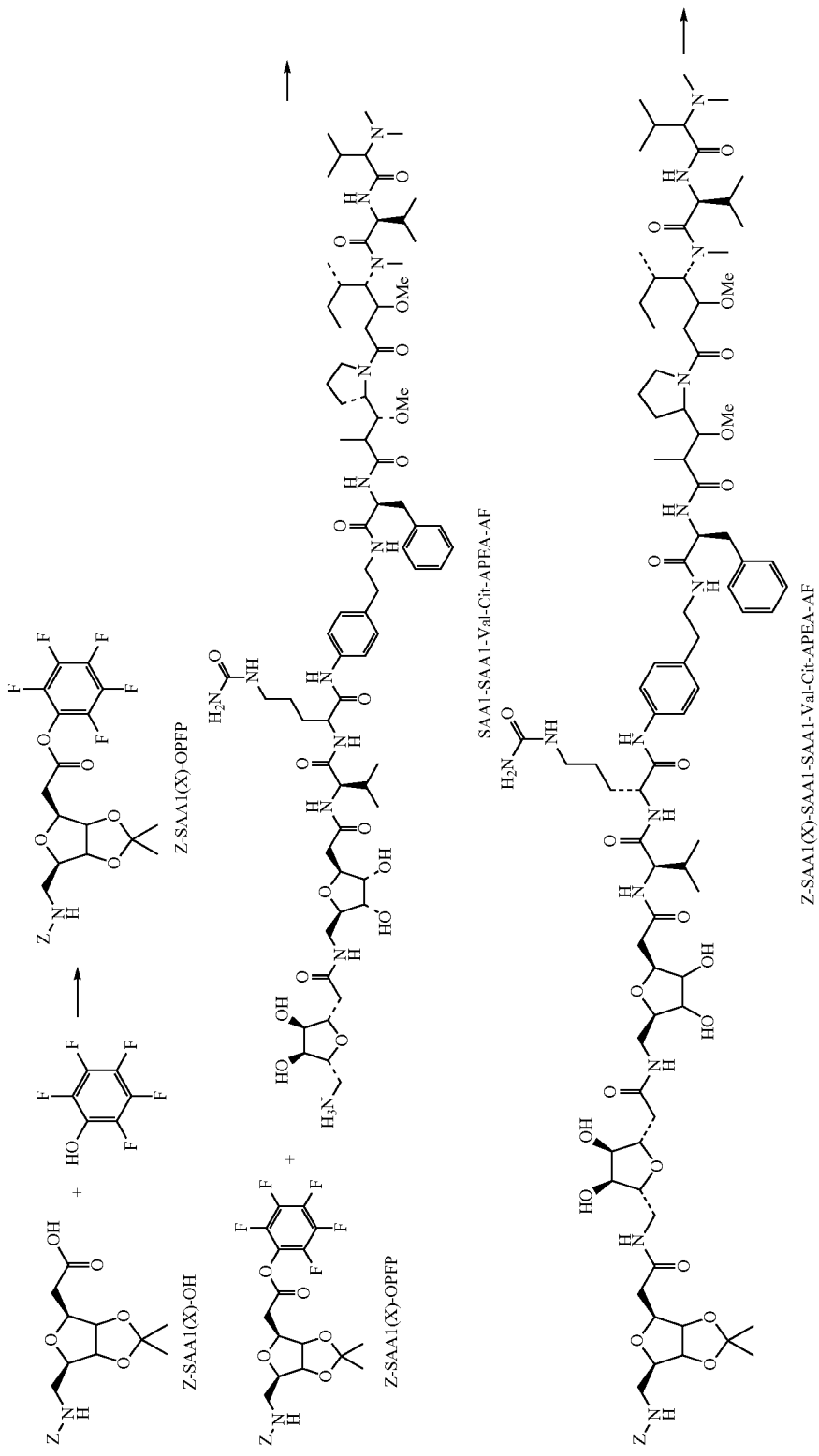

-continued
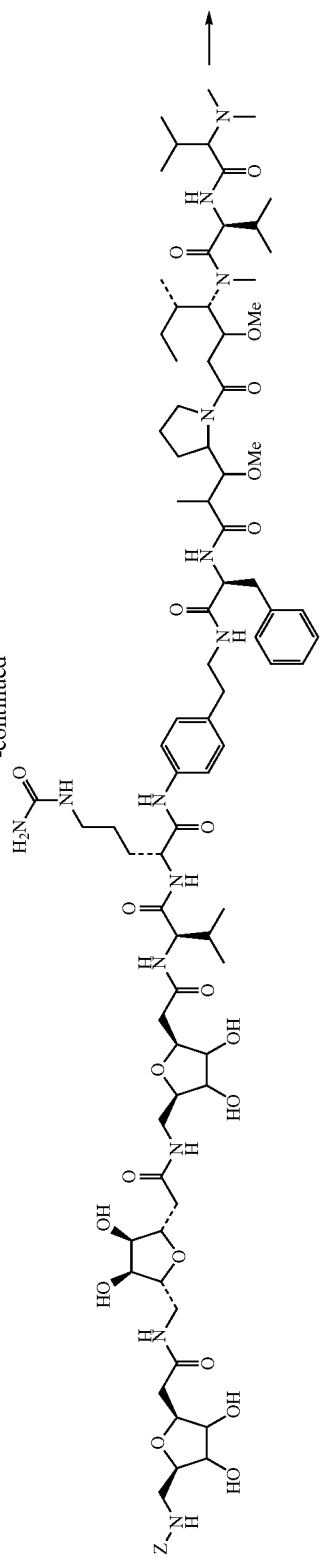
Z-SAA1-SAA1-SAA1-Val-Cit-APEA-AF
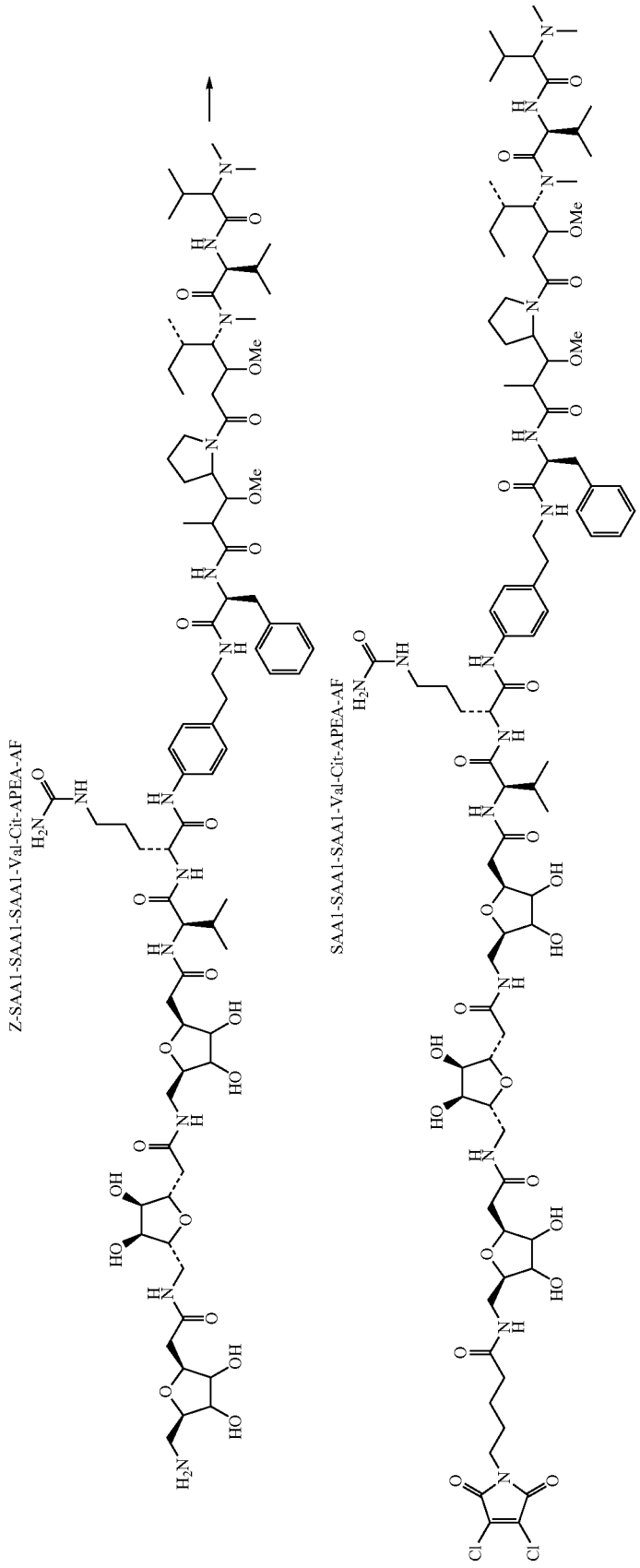
SAA1-SAA1-SAA1-SAA1-Val-Cit-APEA-AF
Cl2MC-SAA1-SAA1-SAA1-Val-Cit-APEA-AF To a solution of Z-SAA1(X)-OH (0.221 g, 0.6048 mmol) and pentafluorophenol (0.134 g, 0.7258 mmol) in dichloromethane (20 mL) was added DCC (0.133 g, 0.6411 mmol). The reaction mixture was stirred at room temperature for 12 hours and then filtered to remove the insoluble DCU. The reaction mixture was evaporated under reduced pressure until the volume reached about 10 ml. The solution was stored in a fridge at 4 degrees for 2 hours. The insoluble material was filtered off and the filtrate was purified by flash column chromatography (EA/Hexane=1/4 to 1/2) to afford Z-SAA1(X)-OPFP as white solids (0.201 g, 63%). LC-MS: Z-SAA1(X)-OPFP ($C_{24}H_{22}F_5NO_{17}$) required [M+H]+= 532.1, found [M+H]+=533.1.

SAA1-SAA1-Val-Cit-APEA-AF (4.8 mg, 0.0090 mmol) and DIPEA (0.004 mL, 0.0225 mmol) were dissolved in DMF (1 mL). After the reaction mixture was immersed in an ice-bath, Z-SAA1(X)-OPFP (4.8 mg, 0.009 mmol) was added. After 10 minutes, the ice-bath was removed and the mixture was stirred at room temperature for 3 hours. The solvent was evaporated under reduced pressure and the crude product was purified by preparative HPLC (33% acetonitrile in water with 0.1% TFA; UV 210 nm; ODS-3 column 30×250 mm; flow rate 25 mL/min). After the removal of acetonitrile, the aqueous solution was kept at room temperature overnight to hydrolysis the acetonide group. The aqueous solution was submitted to freeze-drying to afford Z-SAA1-SAA1-SAA1-Val-Cit-APEA-AF as white solid (13.0 mg, 97% yield over two steps). LC-MS: Z-SAA1-SAA1-SAA1-Val-Cit-APEA-AF ($C_{88}H_{136}N_{14}O_{24}$) required [M+H]+=1774.0, found [M+H]+= 1774.9.

Z-SAA1-SAA-SAA1-Val-Cit-APEA-AF [FCW-043] (13.0 mg, 0.0075 mmol) was dissolved in ethanol (10 mL) containing hydrochloric acid (0.0126 mmol). After Pd/C (10%, 0.8 mg) was charged, the reaction mixture was applied a hydrogen balloon and stirred overnight. The catalyst Pd/C was filtered off through a pad of celite and then the filtrate was evaporated under reduced pressure. The product was mixed with water (5 mL) and submitted to freeze-drying to afford SAA1-SAA1-SAA1-Val-Cit-APEA-AF as white solid (9.0 mg, 75%). LC-MS: SAA1-SAA1-SAA1-Val-Cit-APEA-AF ($C_{80}H_{130}N_{14}O_{22}$) required [M+H]+=1640.0, found [M+H]+=1640.9.

SAA1-SAA1-SAA1-Val-Cit-APEA-AF (5.0 mg, 0.0031 mmol) and DIPEA (0.002 mL, 0.0092 mmol) were dissolved in DMF (1 mL). After the reaction mixture was immersed in an ice-bath, Cl2MC-OPFP (2.0 mg, 0.0037 mmol) was added. After 10 minutes, the ice-bath was removed and the mixture was stirred at room temperature for 3 hours. The solvent was evaporated under reduced pressure and the crude product was purified by preparative HPLC (33% acetonitrile in water with 0.1% TFA; UV 210 nm; ODS-3 column 30×250 mm; flow rate 25 mL/min) to afford Cl2MC-SAA1-SAA1-SAA1-Val-Cit-APEA-AF as white solid (1.0 mg, 17%). LC-MS: Cl2MC-SAA1-SAA1-SAA1-Val-Cit-APEA-AF ($C_{90}H_{139}Cl_2N_{15}O_{25}$) required [M+H]+=1901.0, found [M+H]+=1902.8.

Example 17

Synthesis of MC-SAA3-Val-Cit-APEA-AF

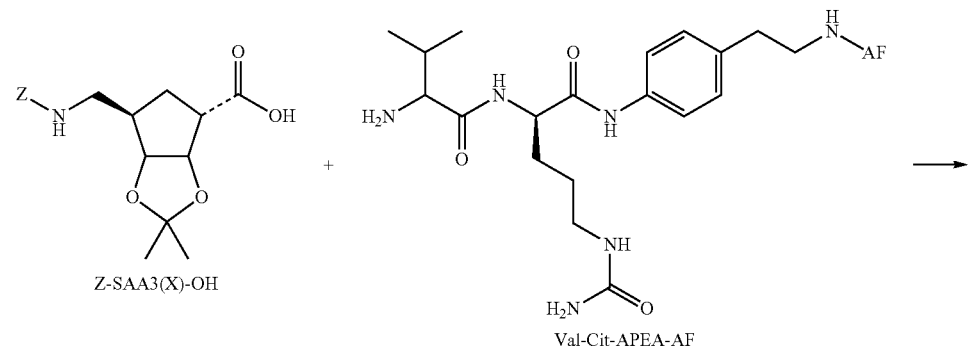

Z-SAA3(X)-OH

Val-Cit-APEA-AF

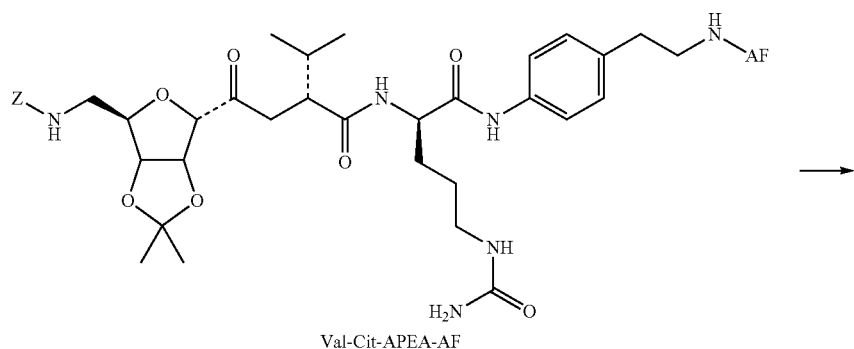

Val-Cit-APEA-AF

-continued

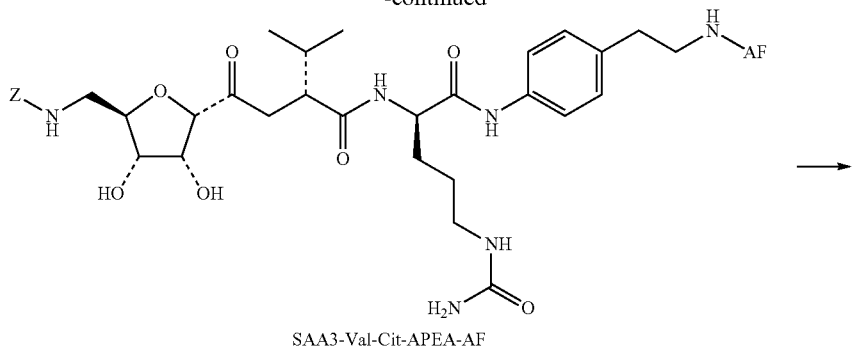
SAA3-Val-Cit-APEA-AF

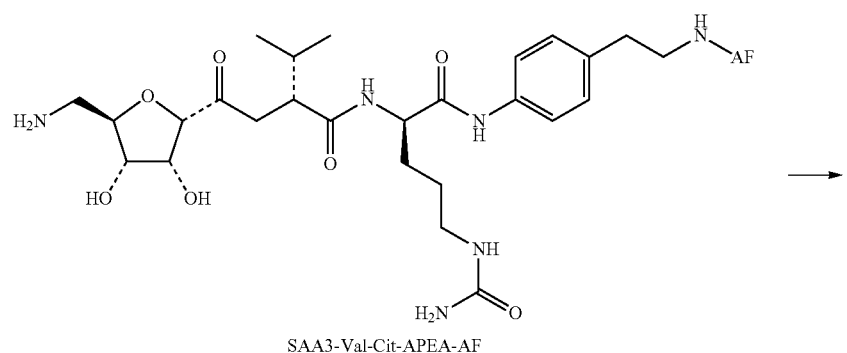
SAA3-Val-Cit-APEA-AF

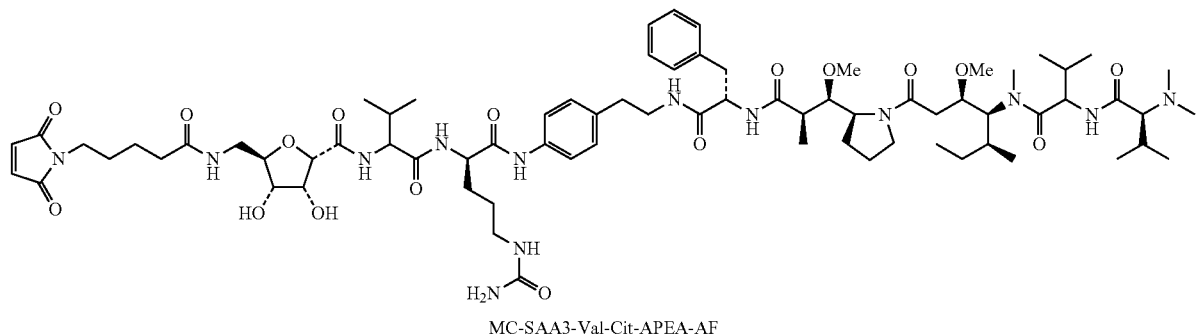
MC-SAA3-Val-Cit-APEA-AF

To a solution of Z-SAA3(X)-OH (18.2 mg, 0.052 mmol) and Val-Cit-APEA-AF (60.0 mg, 0.052 mmol) in a mixture of DCM and DMF (10:1, 6 mL) was added HATU (22.0 mg, 0.0572 mmol) and DIPEA (0.027 mL, 0.156 mmol) respectively. After 18 hours, the solvents were removed under reduced pressure and the crude product was purified by preparative HPLC (43% acetonitrile in water with 0.1% TFA; UV 210 nm; ODS-3 column 30×250 mm; flow rate 24 mL/min). After the removal of acetonitrile, the aqueous solution was stood at room temperature overnight until the acetonide group was completely removed. The aqueous solution was subjected to freeze-drying to afford Z-SAA3-Val-Cit-APEA-AF as white solid (48.0 mg, 65% yield over two steps).

Z-SAA3-Val-Cit-APEA-AF (48.0 mg, 0.034 mmol) was dissolved in ethanol (5 mL) containing hydrochloric acid (0.014 mL). After Pd/C (10%, 4.7 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA3-Val-Cit-APEA-AF as white solid (42.0 mg, 94%).

To a solution of SAA3-Val-Cit-APEA-AF (20.0 mg, 0.015 mmol) and MC-OPFP (6.3 mg, 0.0165 mmol) in DMF (4 mL) was added DIPEA (0.006 mL). The reaction was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA3-Val-Cit-APEA-AF as white solid (12.2 mg; 55%). LC-MS: MC-SAA3-Val-Cit-APEA-AF ($C_{75}H_{117}N_{13}O_{17}$) required [MH$^+$]=1473.8, found [MH$^+$]=1473.6.

Example 18
Synthesis of MC-SAA3-SAA3-Val-Cit-APEA-AF
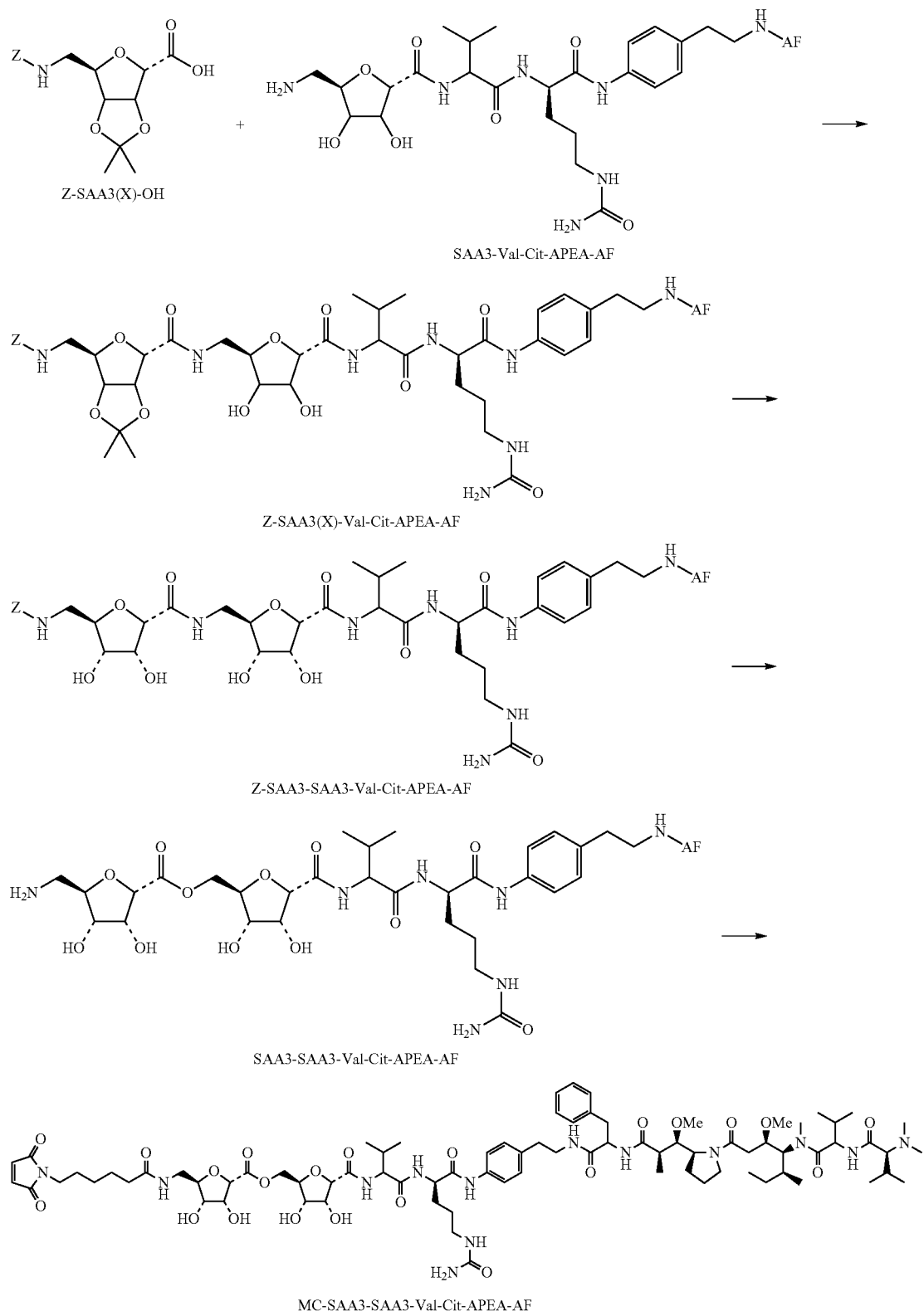

To a solution of Z-SAA3(X)-OH (14.5 mg, 0.041 mmol) and SAA3-Val-Cit-APEA-AF (54.5 mg, 0.041 mmol) in a mixture of DCM and DMF (10:1, 6 mL) was added HATU (17.3 mg, 0.045 mmol) and DIPEA (0.02 mL, 0.123 mmol) respectively. After 18 hours, the solvents were evaporated under reduced pressure and the crude product was purified by preparative HPLC (41% acetonitrile in water with 0.1% TFA; UV 210 nm; ODS-3 column 30×250 mm; flow rate 24 mL/min). After the removal of acetonitrile, the aqueous solution was stood at room temperature overnight until the ketal group was completely hydrolyzed. The aqueous solution was submitted to freeze-drying to afford Z-SAA3-SAA3-Val-Cit-APEA-AF as white solid (21.3 mg, 33% yield over two steps).

Z-SAA3-SAA3-Val-Cit-APEA-AF (21.3 mg, 0.0135 mmol) was dissolved in ethanol (5 mL) containing hydrochloric acid (0.052 mmol). After Pd/C (10%, 2.5 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA3-SAA3-Val-Cit-APEA-AF as white solid (16.1 mg, 81%).

To a solution of SAA3-SAA3-Val-Cit-APEA-AF (16.1 mg, 0.0109 mmol) and MC-OPFP (4.5 mg, 0.012 mmol) in DMF (5 mL) was added DIPEA (0.004 mL). The reaction mixture was stirred at room temperature for 1 hour and then evaporated under reduced pressure. The crude product was purified by preparative HPLC (33% acetonitrile in water with 0.1% TFA; UV 210 nm; ODS-3 column 30×250 mm; flow rate 24 mL/min) to afford MC-SAA3-SAA3-Val-Cit-APEA-AF as white solid (9.2 mg; 52%). LC-MS: MC-SAA3-SAA3-Val-Cit-APEA-AF ($C_{81}H_{126}N_{14}O_{21}$) required [MH$^+$]=1633.0, found [MH$^+$]=1633.2.

Example 19

Synthesis of MC-SAA4-Val-Cit-APEA-AF

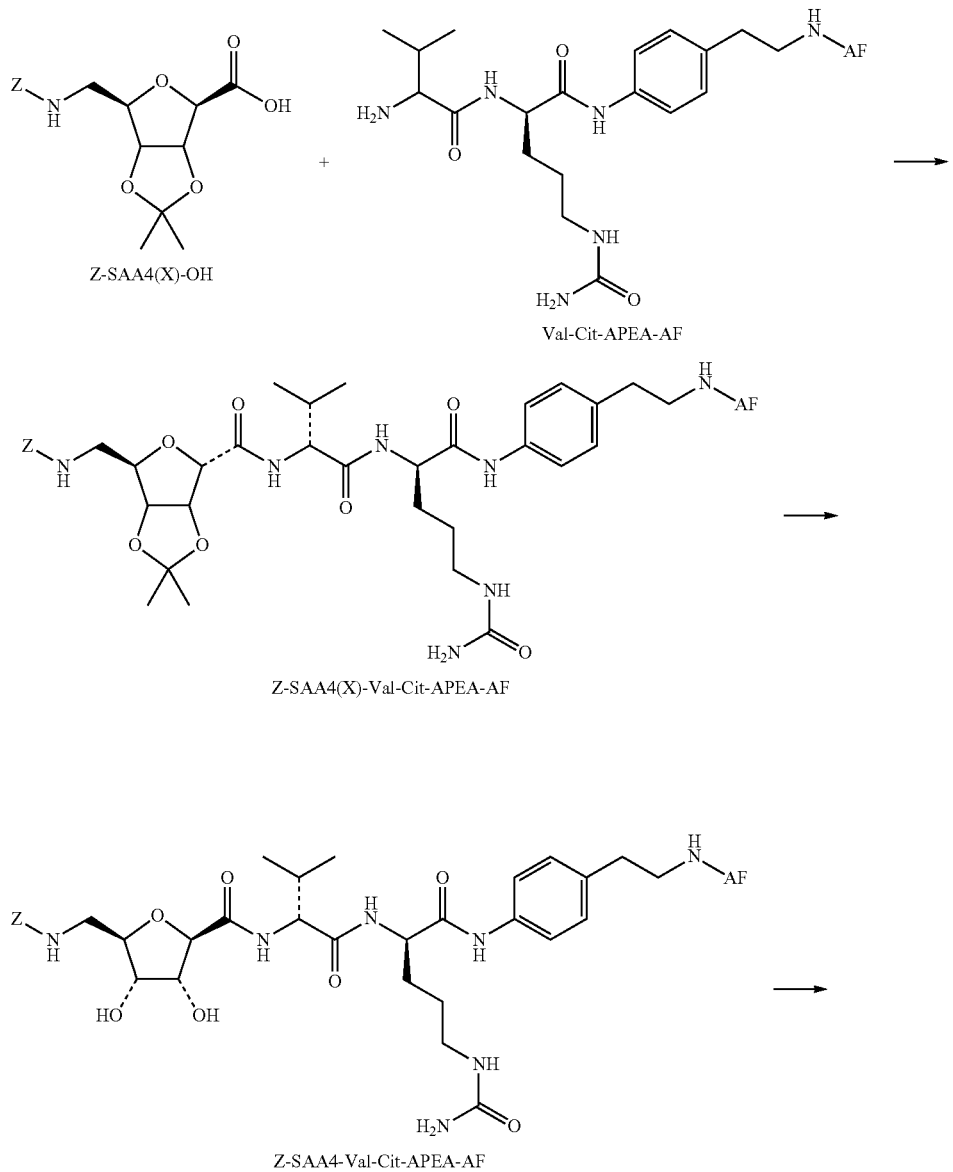

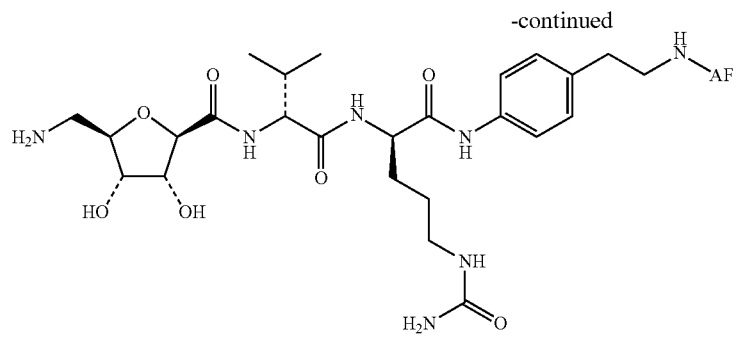

Z-SAA4-Val-Cit-APEA-AF

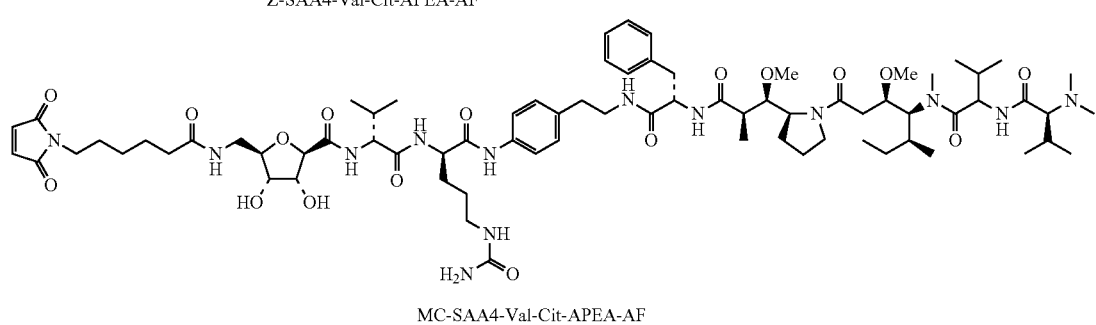

MC-SAA4-Val-Cit-APEA-AF

To a solution of Z-SAA4(X)-OH (15.2 mg, 0.043 mmol) and Val-Cit-APEA-AF (50.0 mg, 0.043 mmol) in a mixture of DCM and DMF (10:1, 6 mL) was added HATU (18.1 mg, 0.0473 mmol) and DIPEA (0.023 mL, 0.129 mmol) respectively. After 18 hours, the solvents were removed under reduced pressure and the crude product was purified by preparative HPLC (43% acetonitrile in water with 0.1% TFA; UV 210 nm; ODS-3 column 30×250 mm; flow rate 24 mL/min). After the removal of acetonitrile, the aqueous solution was stood at room temperature overnight until the removal of acetonide was complete. The aqueous solution was submitted to freeze-drying to afford Z-SAA3-Val-Cit-APEA-AF as white solid (32.4 mg, 53% yield over two steps).

Z-SAA3-Val-Cit-APEA-AF (32.4 mg, 0.0229 mmol) was dissolved in ethanol (5 mL) containing hydrochloric acid (0.09 mmol). After Pd/C (10%, 4.0 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA4-Val-Cit-APEA-AF as white solid (30.0 mg, 98%).

To a solution of SAA4-Val-Cit-APEA-AF (20.0 mg, 0.015 mmol) and MC-OPFP (6.3 mg, 0.0165 mmol) in DMF (4 mL) was added DIPEA (0.006 mL). The reaction was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA4-Val-Cit-APEA-AF as white solid (15.6 mg; 70%). LC-MS: MC-SAA4-Val-Cit-APEA-AF ($C_{75}H_{117}N_{13}O_{17}$) required [MH$^+$]=1473.8, found [MH$^+$]=1473.6.

Example 20

Synthesis of MC-SAA5-Val-Cit-APEA-AF

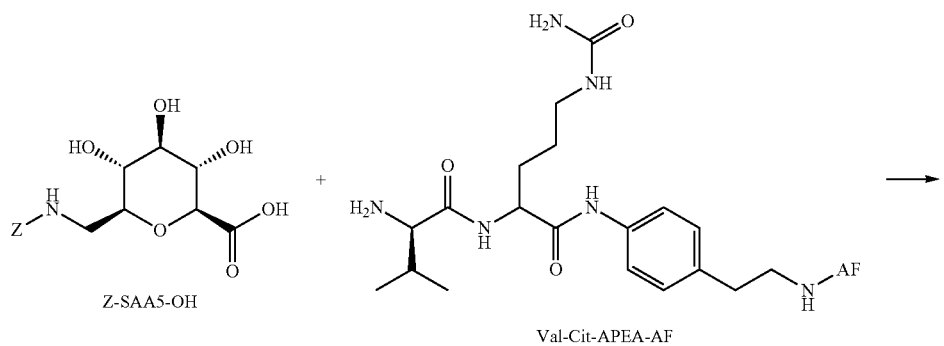

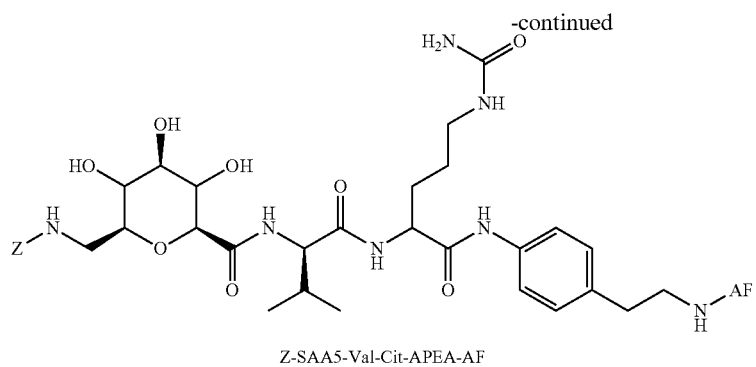

Z-SAA5-Val-Cit-APEA-AF

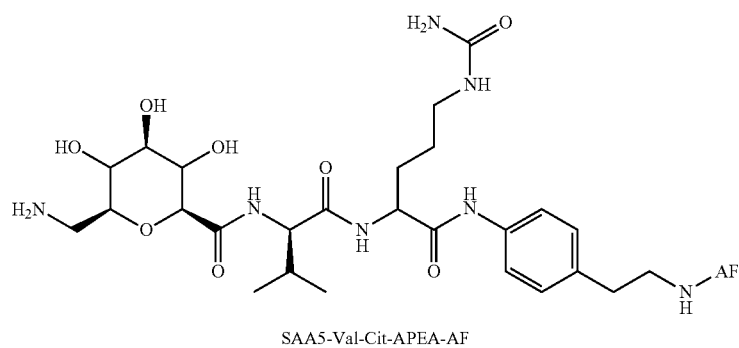

SAA5-Val-Cit-APEA-AF

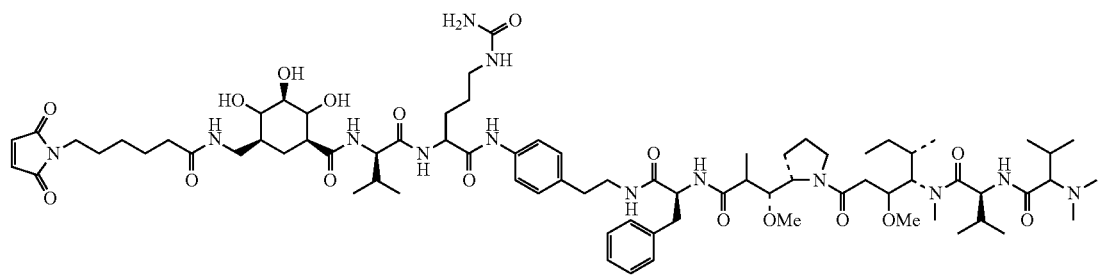

MC-SAA5-Val-Cit-APEA-AF

HATU (40 mg, 0.1060 mmol) was added to a stirred solution of Val-Cit-APEA-AF (99 mg, 0.0884 mmol), Z-SAA5-OH (36 mg, 0.1060 mmol) and DIPEA (0.046 mL, 0.2651 mmol) in a mixture of DMF (2 mL) and dichloromethane (20 mL). After stirring at room temperature for 12 hours, the solvents were evaporated and the residue was purified by preparative HPLC (43% acetonitrile in water with 0.1% TFA; UV 210 nm; ODS-3 column 30×250 mm; flow rate 24 mL/min) to afford Z-SAA5-Val-Cit-APEA-AF as white powder (33 mg, 26%). LC-MS: Z-SAA5-Val-Cit-APEA-AF ($C_{75}H_{115}N_{11}O_{17}$) required [M+2H]2+=721.9, found [M+2H]2+=723.6.

Z-SAA5-Val-Cit-APEA-AF (35.0 mg, 0.024 mmol) was dissolved in ethanol (8 mL) containing HCl (0.048 mmol). After Pd/C (10%, 2.6 mg) was charged, the reaction mixture was applied a hydrogen balloon and stirred for 16 hours. The catalyst Pd/C was filtered off through a pad of celite and then the filtrate was evaporated under reduced pressure. The product was mixed with water (10 mL) and submitted to freeze-drying to afford SAA5-Val-Cit-APEA-AF as white solid (30.0 mg, 95%). LC-MS: SAA5-Val-Cit-APEA-AF ($C_{67}H_{109}N_{11}O_{15}$) required [M+2H]2+=654.9, found [M+2H]2+=656.6.

To a solution of SAA5-Val-Cit-APEA-AF (16.5 mg, 0.0126 mmol) and MC-OPFP (5.7 mg, 0.0151 mmol) in DMF (3 mL) was added DIPEA (0.0066 mL, 0.0378 mmol). The reaction was stirred at room temperature for 3 hours and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA5-Val-Cit-APEA-AF as white solid (12.0 mg; 63%). LC-MS: MC-SAA5-Val-Cit-APEA-AF ($C_{77}H_{120}N_{12}O_{18}$) required [M+2H]2+=751.4, found [M+2H]2+=753.1.

Example 21
Synthesis of MC-SAA6-Val-Cit-APEA-AF
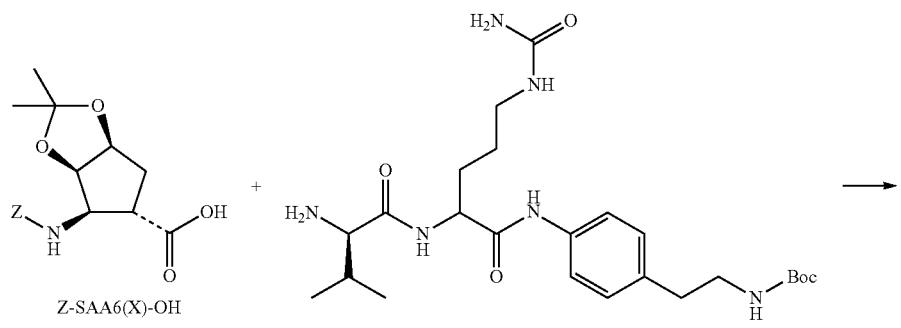
Z-SAA6(X)-OH + Val-Cit-APEA-Boc
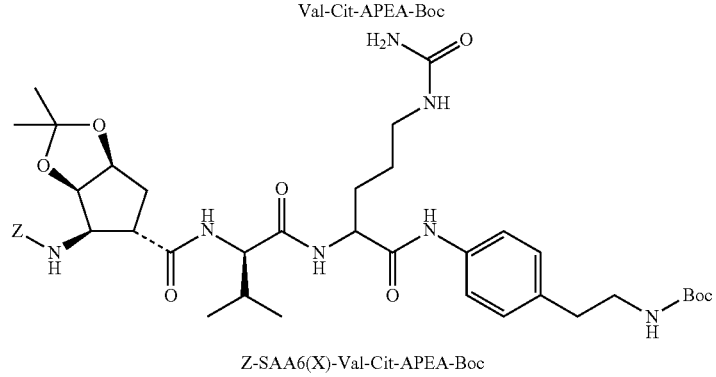
Z-SAA6(X)-Val-Cit-APEA-Boc
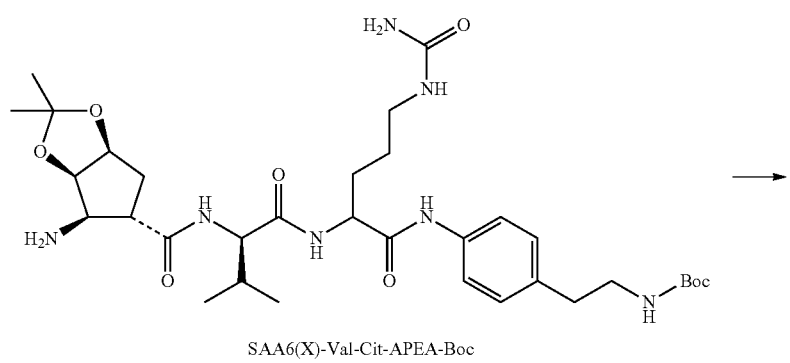
SAA6(X)-Val-Cit-APEA-Boc
MC-SAA6(X)-Val-Cit-APEA-Boc -continued

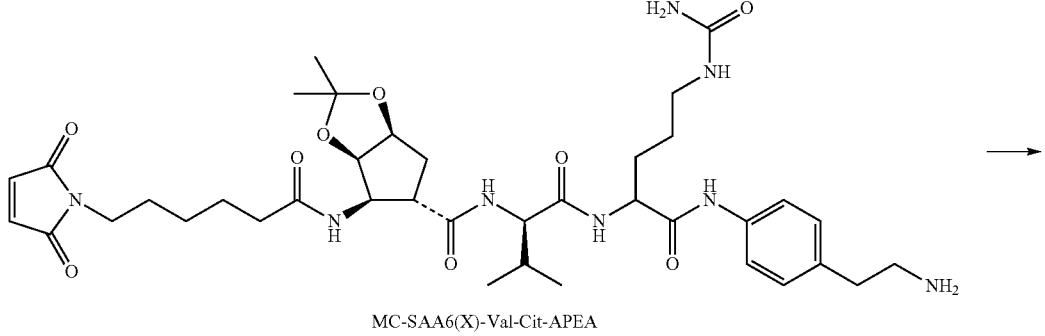

MC-SAA6(X)-Val-Cit-APEA

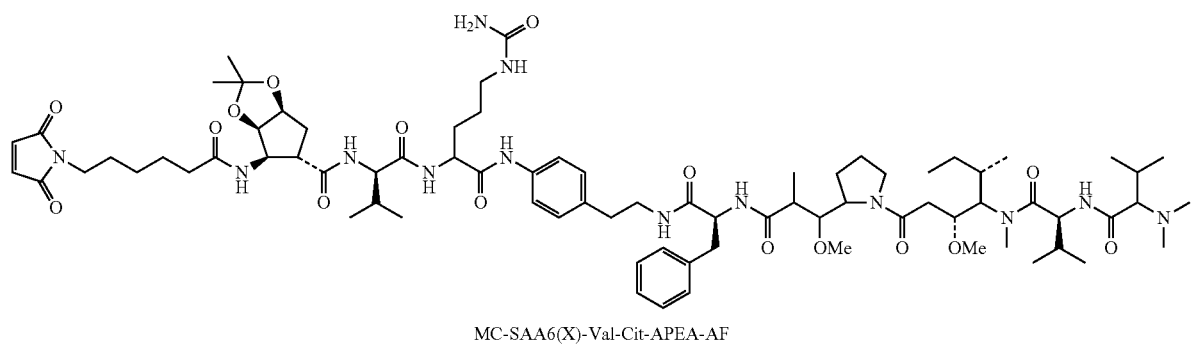

MC-SAA6(X)-Val-Cit-APEA-AF

To a solution of Z-SAA6(X)-OH (100 mg) in dichloromethane (10 mL) was added proton sponge (63 mg) and HBTU (170 mg). The solution of Val-Cit-APEA-Boc (150 mg) in DMF (1 mL) was then added and left overnight. After removal of solvents, the crude product was purified by preparative HPLC (50% acetonitrile in water with 0.1% TFA; UV 210 nm; ODS-3 column 30*500 mm; flow rate 70 mL/min; RT 15 min) to afford Z-SAA6(X)-Val-Cit-APEA-Boc as white solid (122.1 mg). LC-MS: Z-SAA6(X)-Val-Cit-APEA-Boc ($C_{40}H_{57}N_7O_{11}$) required [MH$^+$]=812.42, found [MH$^+$]=813.2.

Z-SAA6(X)-Val-Cit-APEA-Boc (50 mg) was dissolved in methanol (2 mL) followed by addition catalyst Pd/C. The reaction mixture was then applied a hydrogen balloon and left for 17 hours. The catalyst Pd/C was filtered off through a pad of celite, and the methanol was evaporated under reduced pressure to afford SAA6(X)-Val-Cit-APEA-Boc as white solid (37.4 mg).

SAA6(X)-Val-Cit-APEA-Boc (47 mg) and MC-OPFP (28 mg) were dissolved in DMF (4 mL). DIPEA (0.0141 mL) was added to the reaction mixture. After 5 hours, DMF and DIPEA were removed under reduced pressure. The crude product was purified by preparative HPLC (50% acetonitrile in water with 0.1% TFA; UV 210 nm; ODS-3 column 30*500 mm; flow rate 45-50 mL/min; RT 10.8 min) to afford MC-SAA6(X)-Val-Cit-APEA-Boc as white solid (42.5 mg). LC-MS: MC-SAA6(X)-Val-Cit-APEA-Boc ($C_{42}H_{62}N_8O_{12}$) required [MH$^+$]=871.46, found [MH$^+$]=871.5.

MC-SAA6(X)-Val-Cit-APEA-Boc (42.5 mg) in DCM (10 mL) was treated with TFA (0.1 mL) at room temperature. After 17 hours, the DCM and TFA were removed under reduced pressure and a light yellow solid MC-SAA6(X)-Val-Cit-APEA was obtained (40 mg). LC-MS: MC-SAA6(X)-Val-Cit-APEA ($C_{37}H_{54}N_8O_{10}$) required [MH$^+$]=771.40, found [MH$^+$]=771.9.

MC-SAA6(X)-Val-Cit-APEA (32 mg) and auristatin F (27 mg) were dissolved in a mixture of DCM and DMF (10:1, 12 mL). Then, HBTU (20.5 mg) and DIPEA (0.022 mL) were added respectively. After 17 hours, DCM and DMF were removed under reduced pressure. The crude product was purified by preparative HPLC (40% acetonitrile in water with 0.1% TFA; UV 210 nm; ODS-3 column 30*500 mm; flow rate 30 mL/min) to afford MC-SAA6(X)-Val-Cit-APEA-AF as white solid (15 mg). LC-MS: MC-SAA6(X)-Val-Cit-APEA-AF ($C_{77}H_{119}N_{13}O_{17}$) required [MH$^+$]=1498.89, found [MH$^+$]=1500.7.

Example 22
Synthesis of MC-SAA7-Val-Cit-APEA-AF
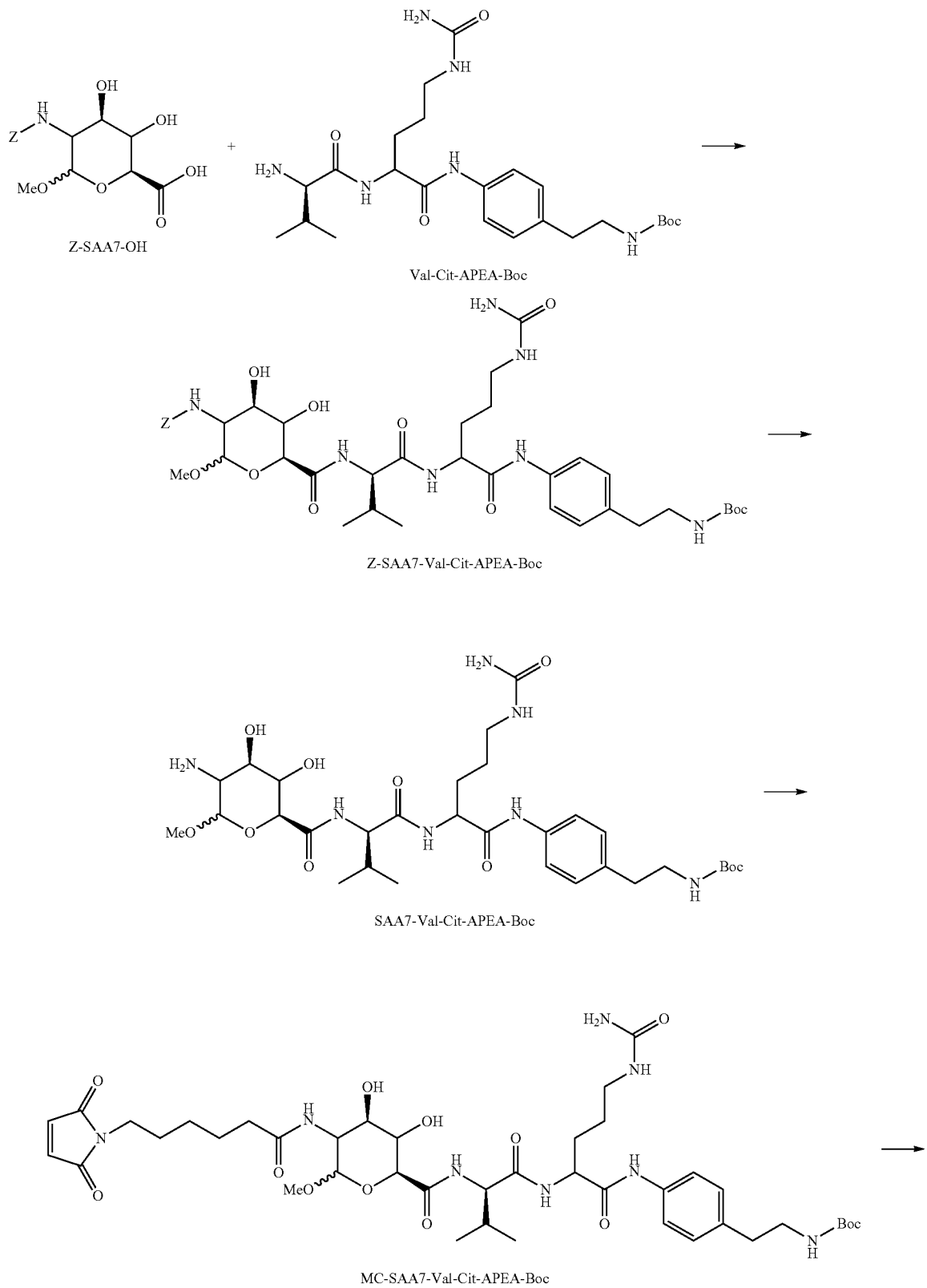

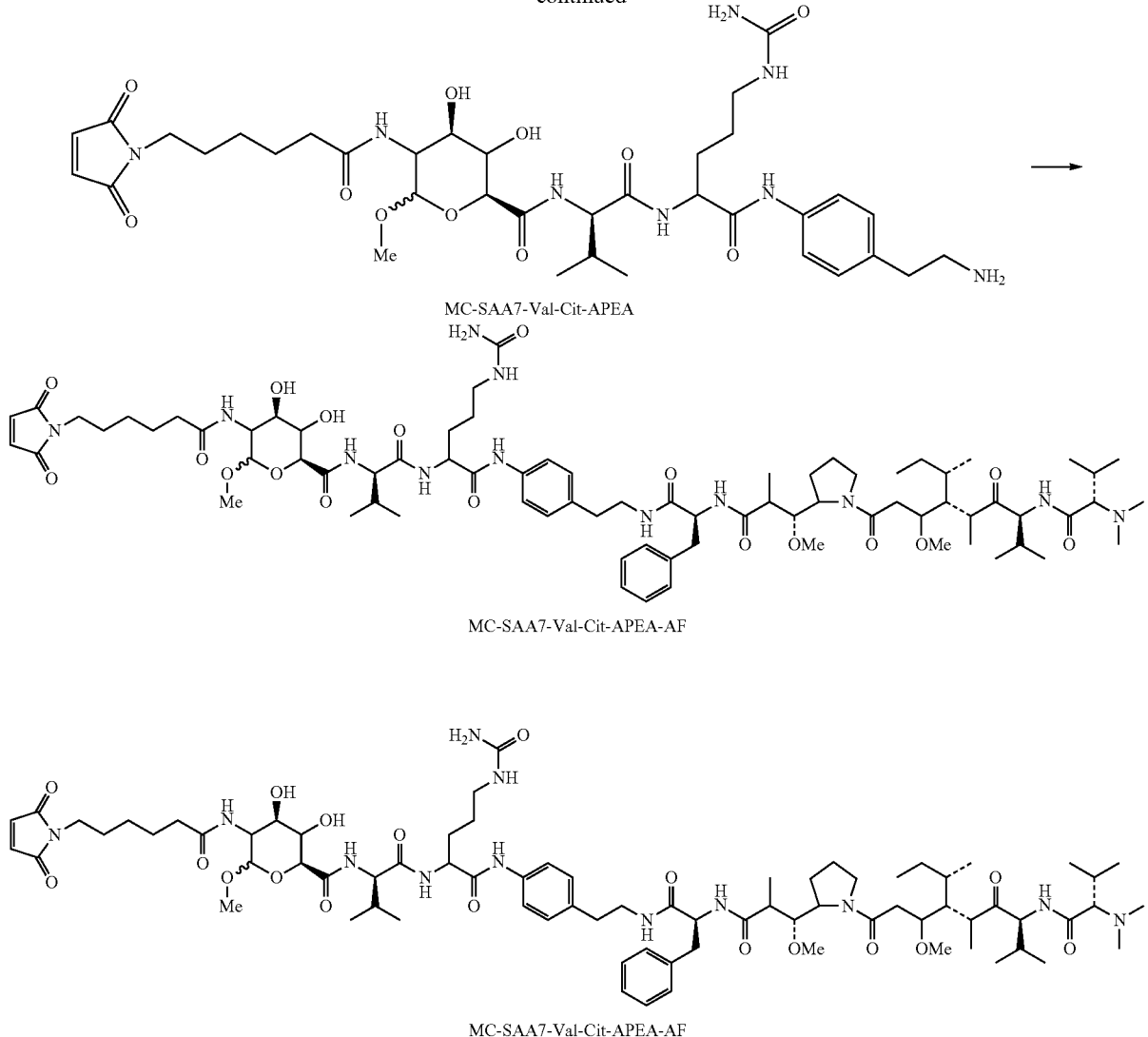

Val-Cit-APEA-Boc (2.46 g, 5 mmol) and Z-SAA7-OH (1.71 g, 5 mmol) were dissolved in DMF (100 mL). Then, DIPEA (646.2 mg, 5 mmol) and HATU (1.90 g, 5 mmol) were added to the reaction mixture. After the mixture was stirred at room temperature for 16 hours, the solvent was evaporated under reduced pressure. The residue was stirred with ethyl acetate (200 mL) for several hours until a fine white powder formed. The solid product was filtered off. The white powder was boiled in water (200 mL) for 15 minutes and then filtered while hot. The product was washed with hot water (50 mL, 2 times) and finally dried under vacuum to afford Z-SAA7-Val-Cit-APEA-Boc.

Z-SAA7-Val-Cit-APEA-Boc (200 mg) was dissolved in methanol (50 mL) followed by addition of catalyst Pd/C. The reaction was then applied a hydrogen balloon and left for 17 hours. The catalyst was filtered off through a pad of celite. The methanol was evaporated under reduced pressure to afford SAA7-Val-Cit-APEA-Boc as white solid (148 mg).

SAA7-Val-Cit-APEA-Boc (240 mg), MC-OPFP (144 mg) and DIPEA (0.072 mL) were dissolved in DMF (20 mL). After 5 hours, DMF and DIPEA were removed under reduced pressure. The residue was mixed with 45% acetonitrile in H$_2$O (20 mL) and then centrifuged. After the removal of the liquid part, MC-SAA7-Val-Cit-APEA-Boc was obtained as white solid (200 mg). LC-MS: MC-SAA7-Val-Cit-APEA-Boc (C$_{41}$H$_{62}$N$_8$O$_{13}$) required [MH$^+$]=875.5, found [MH$^+$]=875.8.

MC-SAA7-Val-Cit-APEA-Boc (200 mg) in DCM (30 mL) was treated with TFA (0.5 mL) at room temperature. After 17 hours, DCM and TFA were removed under reduced pressure and a light yellow solid MC-SAA7-Val-Cit-APEA was obtained (180 mg). LC-MS: MC-SAA7-Val-Cit-APEA (C$_{36}$H$_{54}$N$_8$O$_{11}$) required [MH$^+$]=775.4, found [MH$^+$]=776.0.

MC-SAA7-Val-Cit-APEA (80 mg) and auristatin F (77 mg) were dissolved in a mixture of DCM and DMF (10:1, 16.6 mL). Then, HBTU (64 mg) and DIPEA (0.064 mL) were added respectively. After 17 hours, DCM and DMF were removed under reduced pressure. The crude product was purified by preparative HPLC (40% acetonitrile in water with 0.1% TFA; UV 210 nm; ODS-3 column 30*250 mm; flow rate 25 mL/min; RT 10.42 min) to afford MC-SAA7-Val-Cit-APEA-AF as white solid (50.9 mg). LC-MS: MC-SAA7-Val-Cit-APEA-AF (C$_{77}$H$_{120}$N$_{12}$O$_{18}$) required [MH$^+$]=1503.0, found [MH$^+$]=1504.1.

Example 23
Synthesis of MC-SAA8-Val-Cit-APEA-AF
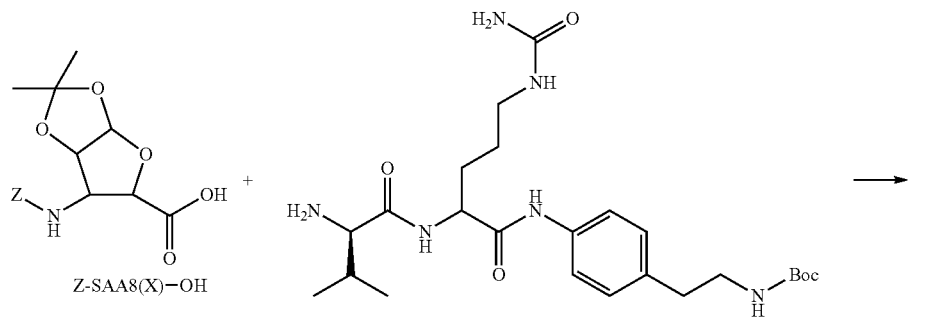
Z-SAA8(X)—OH + Val-CH-APEA-AF
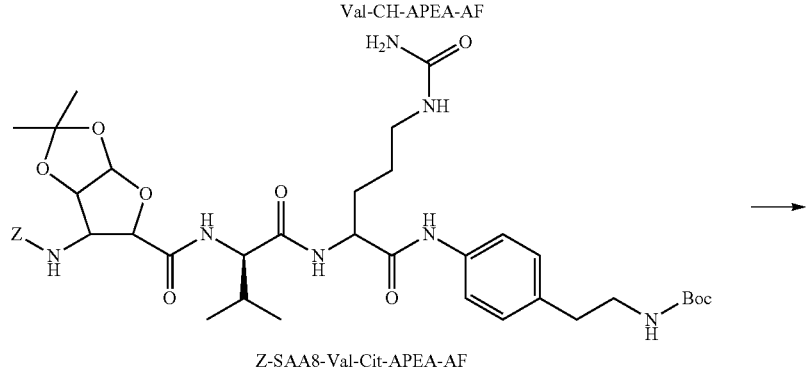
Z-SAA8-Val-Cit-APEA-AF
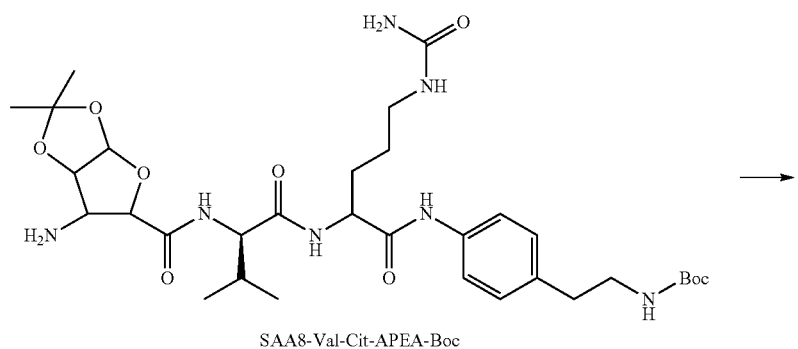
SAA8-Val-Cit-APEA-Boc
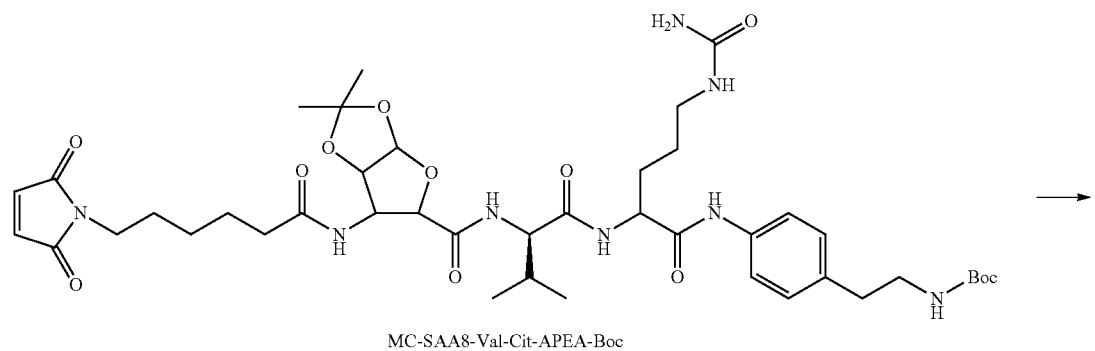
MC-SAA8-Val-Cit-APEA-Boc -continued

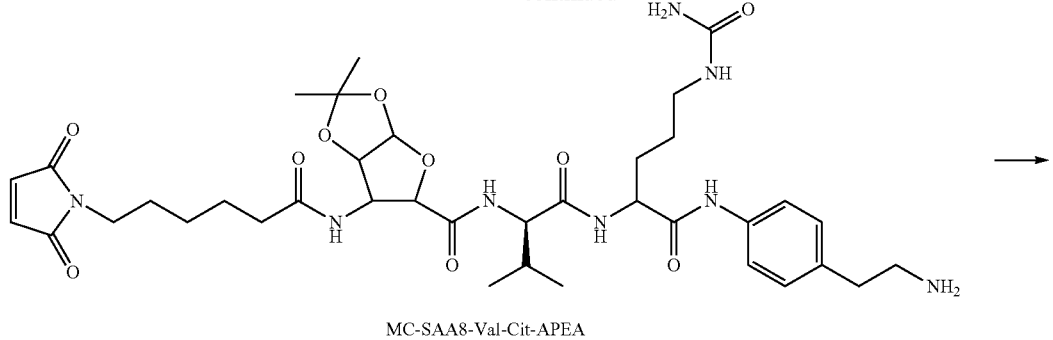

MC-SAA8-Val-Cit-APEA

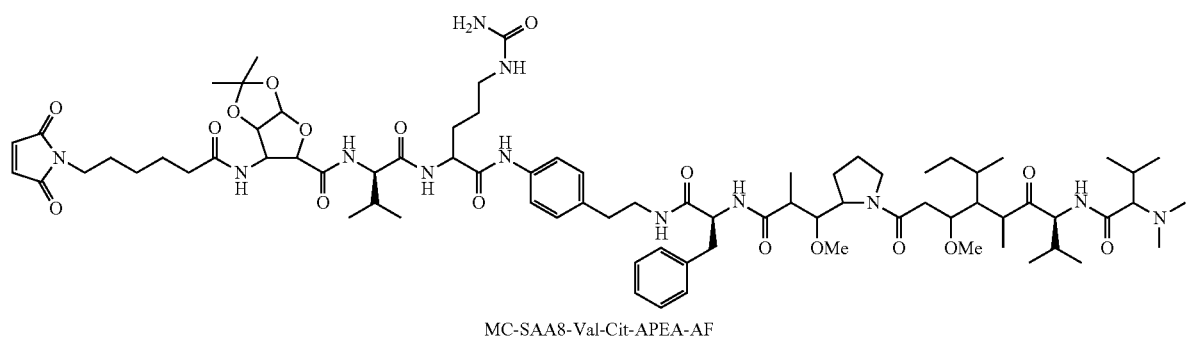 [SMILES: CCC(C)C(C(CC(=O)N1CCCC1C(OC)C(C)C(=O)N[C@@H](Cc1ccccc1)C(=O)NCCc1ccc(NC(=O)C(CCCNC(N)=O)NC(=O)[C@H](NC(=O)C2OC3OC(C)(C)OC3C2NC(=O)CCCCCN2C(=O)C=CC2=O)C(C)C)cc1)OC)C(C)C(=O)[C@@H](NC(=O)C(C(C)C)N(C)C)C(C)C]

MC-SAA8-Val-Cit-APEA-AF

To a solution of Z-SAA8(X)-OH (100 mg) in DCM (10 mL) was added proton sponge (63 mg) and HBTU (170 mg). The solution of Val-Cit-APEA-Boc (150 mg) in DMF (1 mL) was then added and the reaction mixture was left overnight. After removal of solvents, the residue was purified by preparative HPLC (55% acetonitrile in water with 0.1% TFA; UV 210 nm; ODS-3 column 30*500 mm; flow rate 60 mL/min; RT 13 min) to afford Z-SAA8(X)-Val-Cit-APEA-Boc as white solid (144.6 mg). LC-MS: Z-SAA8(X)-Val-Cit-APEA-Boc ($C_{40}H_{57}N_7O_{11}$) required [MH$^+$]=812.4, found [MH$^+$]=813.4.

Z-SAA8(X)-Val-Cit-APEA-Boc (70 mg) was dissolved in MeOH (10 mL) followed by addition of the catalyst Pd/C. The reaction was then applied a hydrogen balloon and left for 17 hours. Then, the catalyst was filtered through a pad of celite. The filtrate was evaporated under reduced pressure to afford SAA8(X)-Val-Cit-APEA-Boc as white solid (54 mg).

SAA8(X)-Val-Cit-APEA-Boc (44 mg) and MC-OPFP (24.2 mg) were dissolved in DMF (4 mL) and then DIPEA (0.0141 mL) was added. After 5 hours, DMF and DIPEA were removed under reduced pressure and the residue was purified by preparative HPLC (45% acetonitrile in water with 0.1% TFA; UV 210 nm; ODS-3 column 30*250 mm; flow rate 35-40 mL/min; RT 13 min) to afford MC-SAA8 (X)-Val-Cit-APEA-Boc as white solid (40 mg). LC-MS: MC-SAA8(X)-Val-Cit-APEA-Boc ($C_{42}H_{62}N_8O_{12}$) required [MH$^+$]=871.5, found [MH$^+$]=872.0.

MC-SAA8(X)-Val-Cit-APEA-Boc (40 mg) in DCM (2 mL) was treated with TFA (0.1 mL) at room temperature. After 17 hours, DCM and TFA were removed under reduced pressure and a light yellow solid MC-SAA8(X)-Val-Cit-APEA was obtained (40 mg). LC-MS: MC-SAA8(X)-Val-Cit-APEA ($C_{37}H_{54}N_8O_{10}$) required [MH$^+$]=771.4, found [MH$^+$]=771.9.

MC-SAA8(X)-Val-Cit-APEA (25.6 mg) and auristatin F (24.5 mg) were dissolved in a mixture of DCM and DMF (10:1, 5.5 mL). Then, HBTU (20.5 mg) and DIPEA (0.022 mL) were added respectively. After 17 hours, DCM and DMF were removed under reduced pressure. The residue was purified by preparative HPLC (40% acetonitrile in water with 0.1% TFA; UV 210 nm; ODS-3 column 30*250 mm; flow rate 35-40 mL/min) to afford compound MC-SAA8 (X)-Val-Cit-APEA-AF as white solid (3.3 mg). LC-MS: MC-SAA8(X)-Val-Cit-APEA-AF ($C_{78}H_{120}N_{12}O_{17}$) required [MH$^+$]=1497.9, found [MH$^+$]=1500.5.

Example 24
Synthesis of MC-Val-Cit-AAF-3AQ
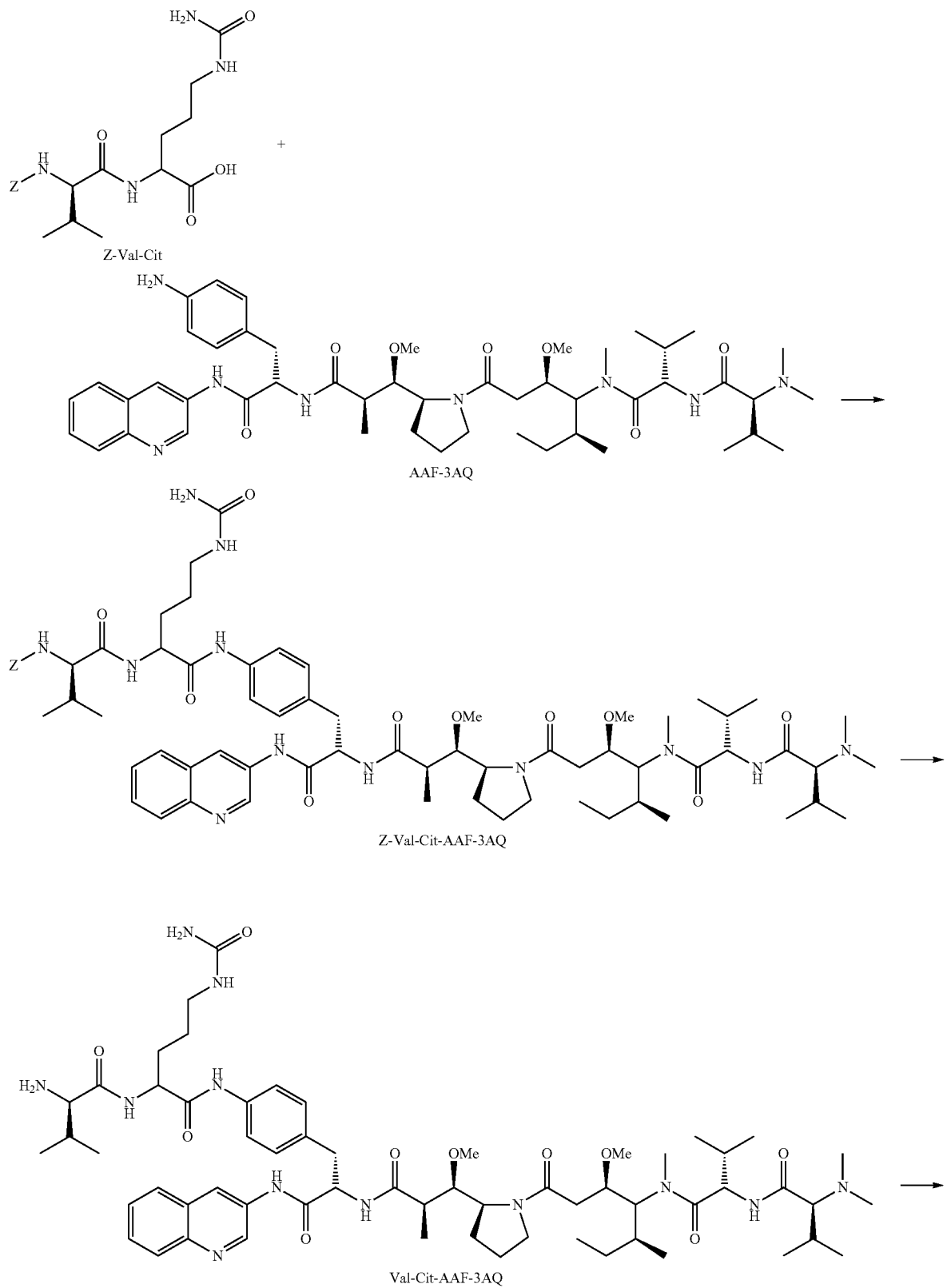

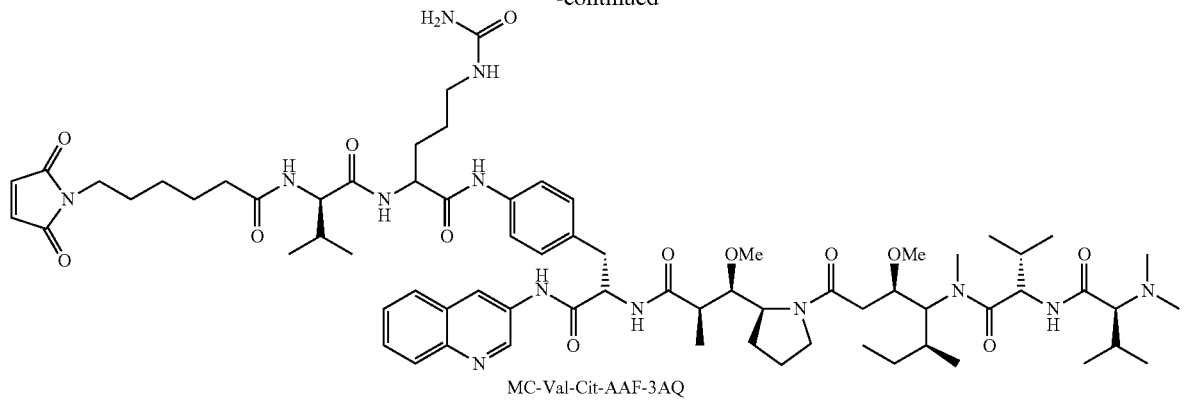

MC-Val-Cit-AAF-3AQ

AAF-3AQ (30.8 mg, 0.035 mmol) was dissolved in a mixture of EtOH (10 mL) and DCM (10 mL). After Z-Val-Cit (15.7 mg, 0.038 mmol) and EEDQ (13 mg, 0.052 mmol) were added, the mixture was stirred at room temperature for 7 days. The reaction mixture was evaporated under reduced pressure and then purified by preparative HPLC (34% acetonitrile in water with 0.1% TFA; UV 210 nm; ODS-3 column 30*250 mm; flow rate 24 mL/min) to afford Z-Val-Cit-AAF-3AQ as white solid (4.83 mg, 10.7%). LC-MS: Z-Val-Cit-AAF-3AQ ($C_{69}H_{101}N_{11}O_{12}$) required [MH$^+$]=1277.6, found [MH$^+$]=1278.9.

Z-Val-Cit-AAF-3AQ (4.8 mg, 0.00376 mmol) was dissolved in ethanol (10 mL). After Pd/C (10%, 16 mg) was charged, the reaction mixture was applied a hydrogen balloon and stirred for 4 hours. The catalyst Pd/C was filtered off through a pad of celite and then the filtrate was evaporated under reduced pressure. The product was mixed with water (5 mL) and submitted to freeze-drying to afford Val-Cit-AAF-3AQ as white solid (4.2 mg, 98%). LC-MS: Val-Cit-AAF-3AQ ($C_{61}H_{95}N_{11}O_{10}$) required [MH$^+$]=1143.5, found [MH$^+$]=1144.7.

Val-Cit-AAF-3AQ (4.8 mg, 0.00367 mmol) and MC-OPFP (1.67 mg, 0.0044 mmol) were dissolved in DMF (0.5 mL). DIPEA (1.9 mg, 0.0147 mL) was added to the reaction mixture. After 3 hours, DMF and DIPEA were removed under reduced pressure. The crude product was purified by preparative HPLC (32% acetonitrile in water with 0.1% TFA; UV 210 nm; ODS-3 column 30*250 mm; flow rate 24 mL/min) to afford MC-Val-Cit-AAF-3AQ as white solid. LC-MS: MC-Val-Cit-AAF-3AQ ($C_{71}H_{106}N_{12}O_{13}$) required [MH$^+$]=1336.7, found [MH$^+$]=1337.7.

<Potency Test>

Example 25

Potency of AF Derivatives

FaDu cells were seeded in Corning CellBIND 96-well plates at densities of 2500 cells/well. After incubation for 24 hours, the old medium was removed and the cells were incubated in MMAE, AF, or AF-derivatives containing media at concentrations ranging from 1e-12 M to 1e-6 M (log serial dilutions) for 120 hours. Then, the cells were rinsed once and assayed for cell viability with the MTT method. The old medium was aspirated and 100 uL of 0.5 mg/mL MTT containing medium was added into each well. After incubation for 4 hours, the MTT reagent was removed and the precipitate was dissolved in DMSO. The photometry intensity of the cells was measured by the microplate reader (Multiskan Ascent, Thermo Labsystems) of absorbance wavelength at 570 nm. Cell viability was calculated by the following equation.

Cell Viability (%)=(Ins−Inb)/(Inc−Inb)×100%

In this equation, "Ins" is the photometry intensity of the cells incubated with a given toxin, "Inb" is the intensity of a blank well without cell seeding, and "Inc" is the intensity of the cells incubated with the culture medium only (positive control).

The in vitro viability of FaDu cells after exposure to toxins for 120 hours at various drug concentrations (n=6) were recorded, and the data were fitted to obtain IC$_{50}$ values using Sigmoidal model of Origin software.

Table 2 shows that the potency of APEA-AF, PEA-AF, PEA-ANF, PEA-AAF, 3AQ-ANF, 3AQ-AAF, NPEA(COOMe)-AF, and APEA(COOMe)-AF in FaDu cells are comparable to the well-known toxin MMAE and significantly more potent than another well-known toxin auristatin F (AF). It demonstrates that the novel derivatives of AF of the disclosure not only improve the permeability to the cell membrane, but also maintain the inhibitory effects to tubulin polymerization. Furthermore, NPEA(COOH)-AF having similar potency to AF and APEA(COOH)-AF shows the least potency, these results indicating that the COOH group may interfere with the permeability of the toxin to across the cell membrane. This behavior of the novel toxins of the disclosure is further used to construct a novel drug without the by-stander effect.

TABLE 2

| Toxin | IC$_{50}$ (nM) |
|---|---|
| MMAE | 0.38 |
| AF | 15.2 |
| APEA-AF | 0.70 |
| PEA-AF | 0.43 |
| PEA-ANF | 1.26 |
| PEA-AAF | 0.39 |
| 3AQ-ANF | 0.35 |
| 3AQ-AAF | 0.49 |
| NPEA(COOMe)-AF | 0.44 |
| NPEA(COOH)-AF | 23.2 |
| APEA(COOMe)-AF | 0.93 |
| APEA(COOH)-AF | >>100 |

<Antibody Drug Conjugates (ADCs)>

Example 26

Preparation of Erbitux Derived ADCs

Erbitux was treated with 2.4 molar equivalent of TCEP in 0.025 M sodium borate, 0.025 M NaCl, 1 mM DTPA (pH=8) for 2 hours at 37° C. Without further purification, the reaction mixture was then cooled to 0° C. Then, the partially reduced Erbitux was alkylated with 5.5 molar equivalent of linker-toxins at 0° C. for 30 minutes. Cysteine (1 mM final) was used to quench any unreacted, excess linker-toxins. The ADCs were purified by desalting column (ThermoFisher Scientific, MWCO: 40K). During elution, the buffer was changed to Dulbecco's phosphate-buffered saline (Thermo-Fisher Scientific, PBS). The ADCs were analyzed by HIC for conjugates distribution and average DAR (Drug-to-Antibody Ratio) was calculated.

FIG. 1 shows that the novel linker-toxin MC-SAA1-Val-Cit-APEA-AF of the disclosure was successfully conjugated on to Erbitux and the average DAR determined by HIC was 3.8.

<Thermal Stress Test>

Example 27

Thermal Stress Test of ADCs

500 μL of 3 mg/mL Erbitux and ADCs in PBS were incubated in a water bath at 50° C. Then the antibody and ADCs were sampled at 0, 4, 7 and 24 hours for SEC analysis. A Waters PDA 996 HPLC with the Yarra 3 μm SEC-3000 (300×7.8 mm) column was used to separate antibody monomer and aggregation products by size. The mobile phase consisted of 0.020 M potassium phosphate, 0.025 M potassium chloride, and isopropanol 5% (v/v), pH 6.95. 30 μL of samples were injected into the column at a flow rate of 0.5 mL/min and separated under isocratic conditions. Absorbance was detected at 280 nm. All species eluting prior to the main peak were integrated together and are reported as high molecular weight species (HMWS).

Figure 2:
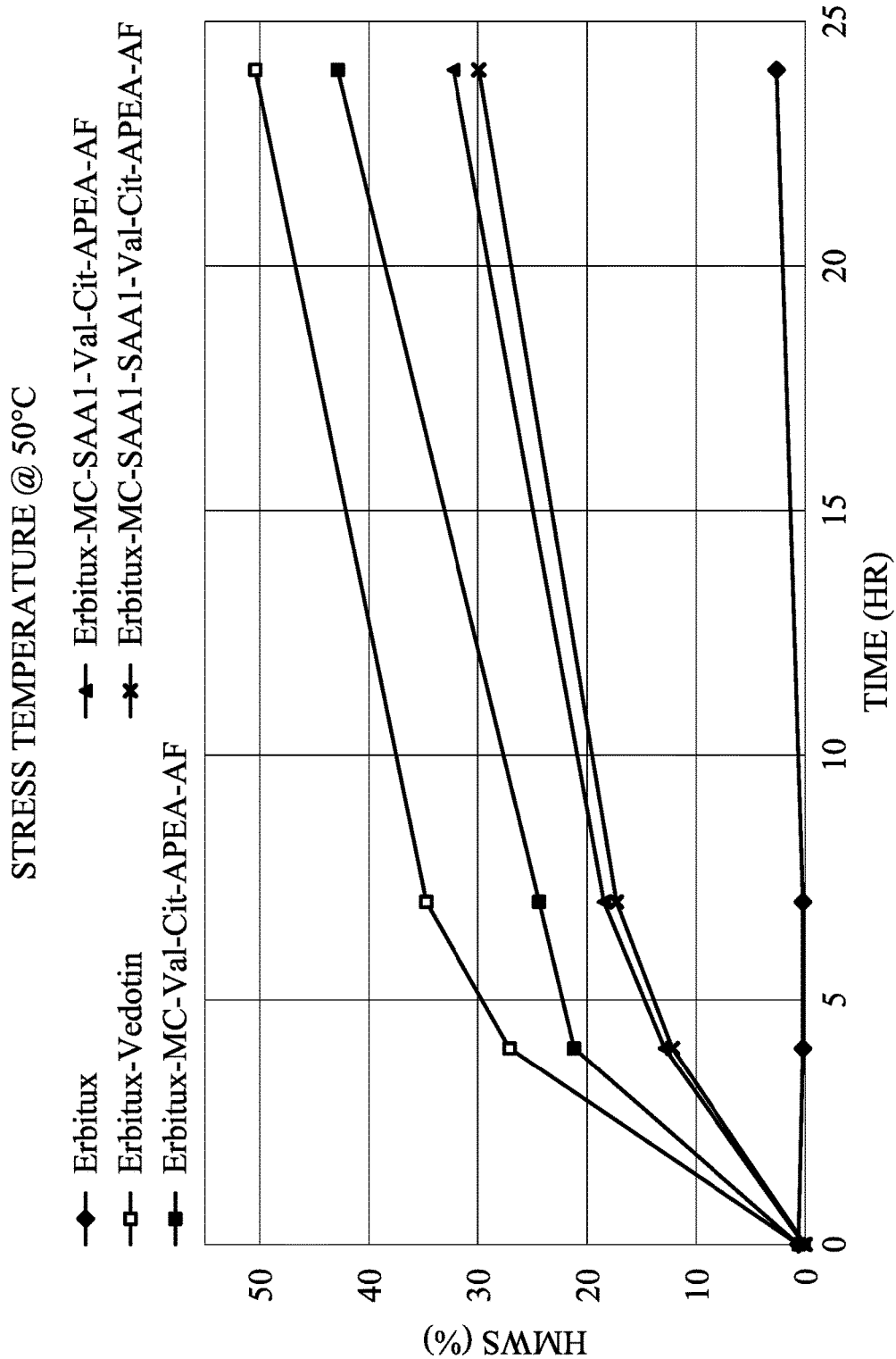
FIG. 2 shows results of a thermal-stress stability test at 50° C. for Erbitux and Erbitux-ADCs.

FIG. 2 showed that Erbitux-MC-SAA1-Val-Cit-APEA-AF and Erbitux-MC-SAA1-SAA1-Val-Cit-APEA-AF whose linkers contain sugar amino acid unit(s) had lower percentages of HMWS than Erbitux-Vedotin and Erbitux-Val-Cit-APEA-AF whose linkers do not contain any sugar amino acid unit. Therefore, this experiment demonstrated that the linkers with sugar amino acid unit(s) not only increase the hydrophilicity but also significantly improve the thermal stability of ADCs.

<Peptide Drug Conjugates (PDCs)>

Example 28

Synthesis of Zoptarelin-GA-SAA1-Val-Cit-APEA-AF

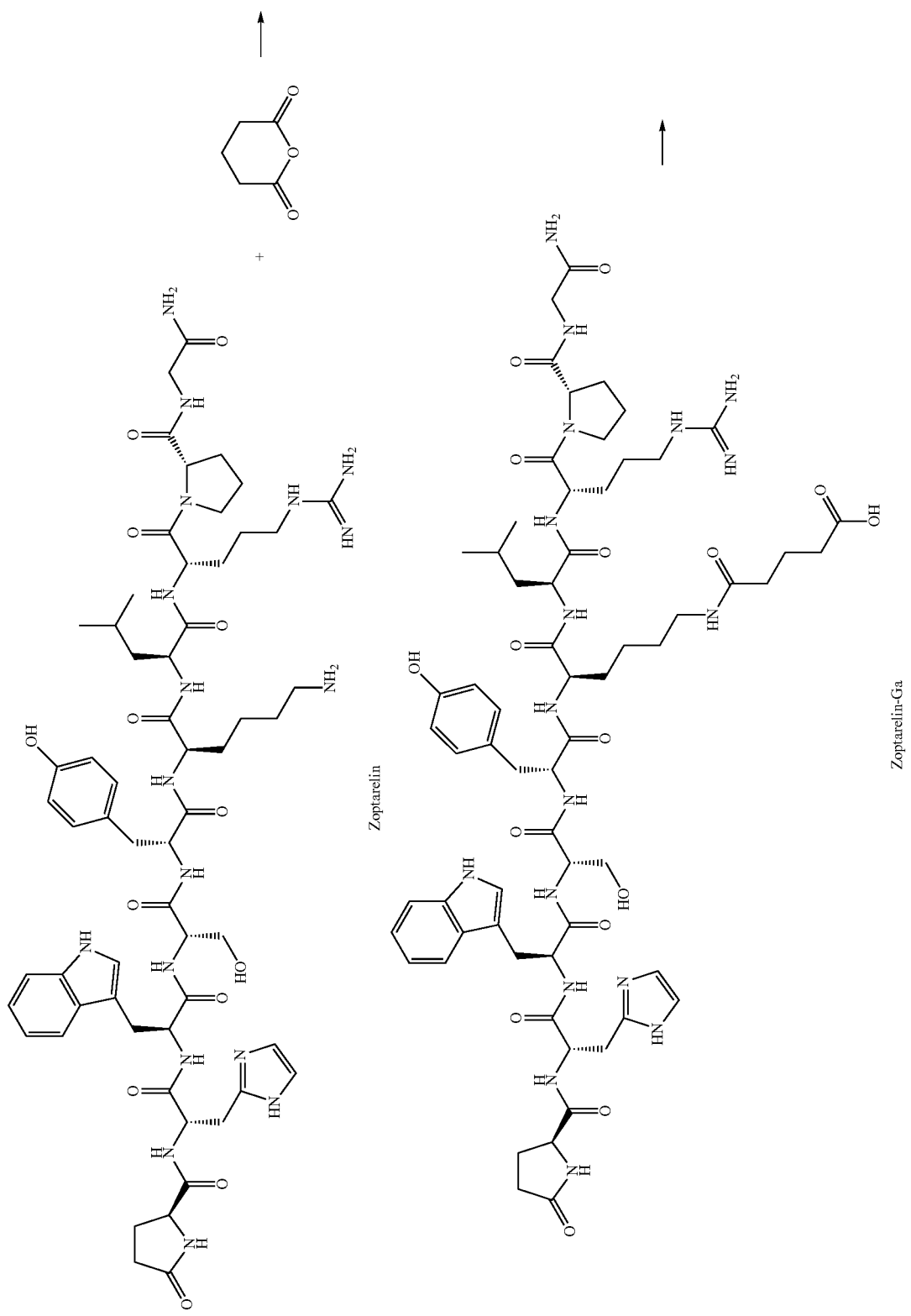

-continued
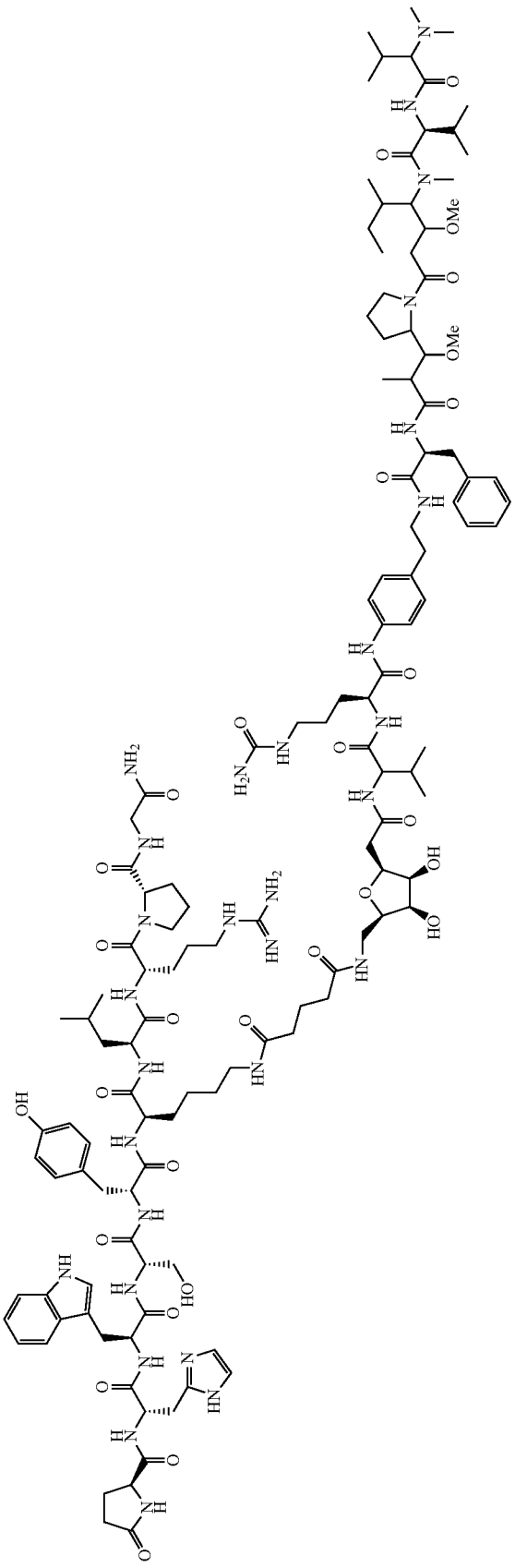
Zoptarelin-GA-SAA1-Val-Cit-APEA-AF

DIPEA (0.071 mL, 0.4070 mmol) was added to a stirred solution of zoptarelin (170 mg, 0.1356 mmol) and glutaric anhydride (17 mg, 0.1492 mmol) in DMF (4 mL). After stirring at room temperature for 12 hours, the solvent was removed and the residue was purified by preparative HPLC to afford Zoptarelin-GA as white powder (100 mg, 54%). LC-MS: Zoptarelin-GA ($C_{64}H_{90}N_{18}O_{16}$), required [MH$^+$]= 1367.7, [M+2H$^+$]=684.4; found [MH$^+$]=1368.7, [M+2H$^+$]=685.5.

To a solution of Zoptarelin-GA (10 mg, 0.0073 mmol) and pentafluorophenol (1.6 mg, 0.0088 mmol) in DMF (1 mL) was added DCC (1.8 mg, 0.0088 mmol). The reaction mixture was stirred at room temperature for 12 hours, then SAA1-Val-Cit-APEA-AF (9 mg, 0.0072) and DIPEA (0.0038 mL, 0.0216 mmol) in DMF (1 mL) was added. After another 12 hours, the solvent was removed and the residue was purified by preparative HPLC to afford Zoptarelin-GA-SAA1-Val-Cit-APEA-AF as white powder (8 mg, 43%). LC-MS: Zoptarelin-GA-SAA1-Val-Cit-APEA-AF ($C_{130}H_{196}N_{30}O_{29}$), required [M+2H$^+$]=1322.6, [M+3H$^+$]= 882.1, [M+4H$^+$]=661.8; found [M+2H$^+$]=1323.7, [M+3H$^+$]= 882.7, [M+4H$^+$]=662.6.

<Small Molecule Drug Conjugates (SMDCs)>

Example 29

Synthesis of FA-C-APEA-AF

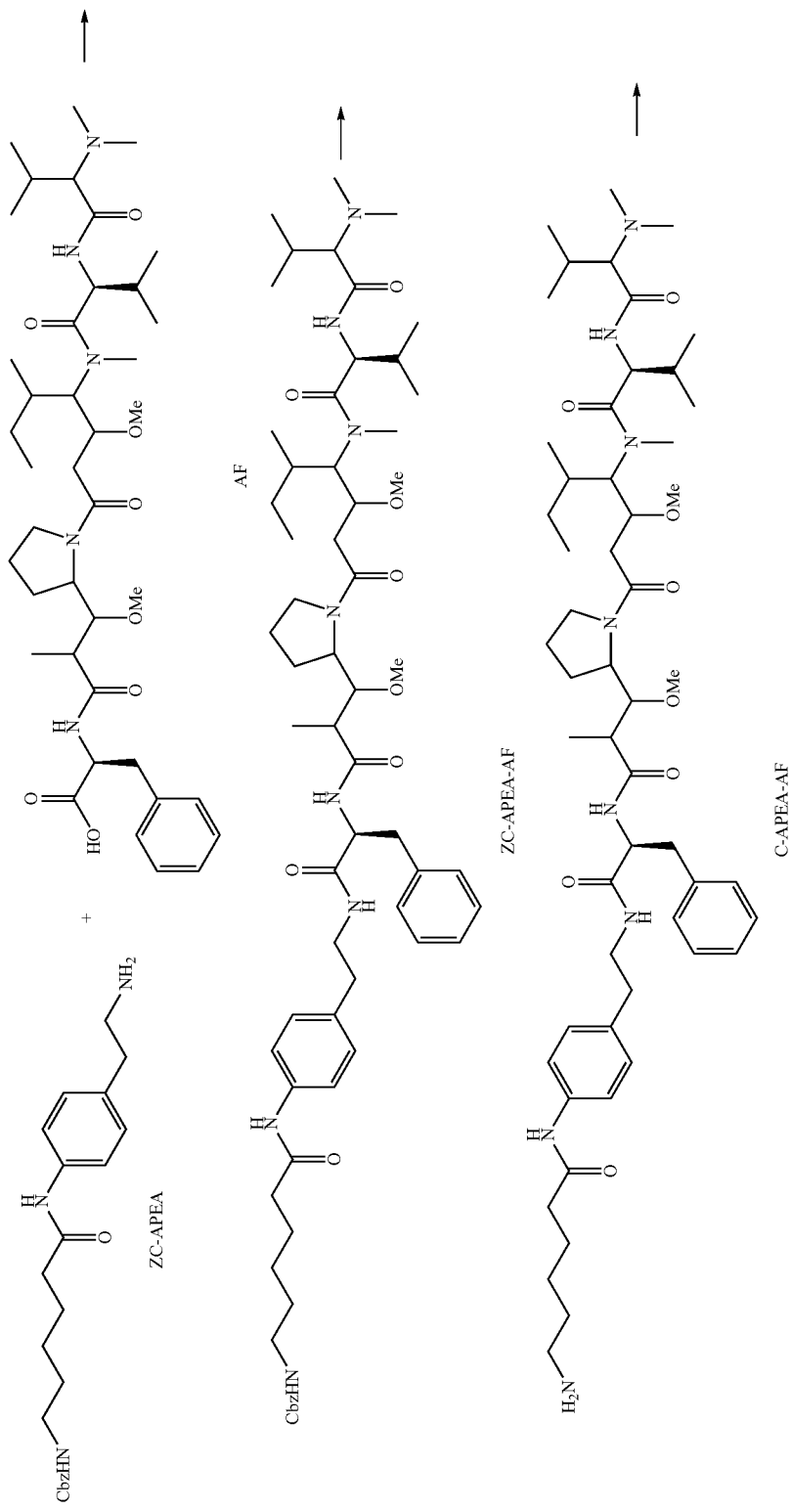

-continued
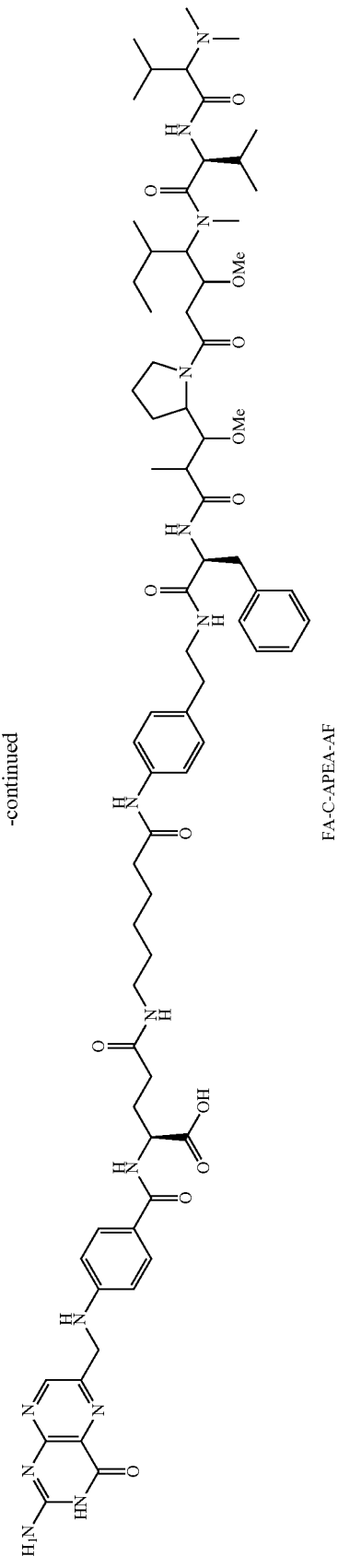
FA-C-APEA-AF

To a solution of AF (20.8 mg, 0.027 mmol) in DMF (0.5 ml) and DCM (1 ml) was added ZC-APEA (10.2 mg, 0.027 mmol). Additional DMF (1 ml) and HATU (10.7 mg, 0.028 mmol) were added to the reaction mixture. The mixture was cooled in an ice-bath, and DIPEA (8.03 mg, 0.062 mmol) was added. After reaction at room temperature for 2 hours, the mixture was evaporated under reduced pressure. The residue was purified by preparative HPLC (45% acetonitrile in water with 0.1% TFA; UV 210 nm; ODS-3 column 30*250 mm; flow rate 24 mL/min) to afford ZC-APEA-AF as white solid (18.2 mg, 51.1%). LC-MS: ZC-APEA-AF ($C_{62}H_{94}N_8O_{10}$) required [MH$^+$]=1111.7, found [MH$^+$]=1112.5.

To a solution of ZC-APEA-AF (18.2 mg, 0.014 mmol) in EtOH (5 mL) was added 10% Pd/C (3 mg) and 2M HCl (0.016 mL, 0.032 mmol). Air in the system was replaced by hydrogen gas. The reaction was carried under ambient atmosphere. When ZC-APEA-AF consumed completely, catalyst was removed from reaction mixture by a filter paper and the filtrate was concentrated followed by mixing with water (5 mL) and lyophilization to afford C-APEA-AF (14.5 mg, 99%).

Folic acid (8.0 mg, 0.018 mmol) was reacted with EDCI (6.2 mg, 0.040 mmol) and NHS (2.6 mg, 0.026 mmol) in DMF (2 ml) in an ice bath. Then, C-APEA-AF (17.4 mg, 0.017 mmol) and DIPEA (8.8 mg, 0.068 mmol) were added after 30 min. After HPLC indicated the C-APEA-AF was almost consumed, DMF was removed from the mixture and the residue was purified by preparative HPLC (36% acetonitrile in water with 0.1% TFA; UV 210 nm; ODS-3 column 30*250 mm; flow rate 24 mL/min). Certain fractions were concentrated and lyophilized to afford FA-C-APEA-AF as yellow solid (5.4 mg, 23.3%). LC-MS: FA-C-APEA-AF ($C_{73}H_{105}N_{15}O_{13}$) required [MH$^+$]=1400.8, found [MH$^+$]=1401.8.

Example 30

Synthesis of FA-Val-Cit-APEA-AF

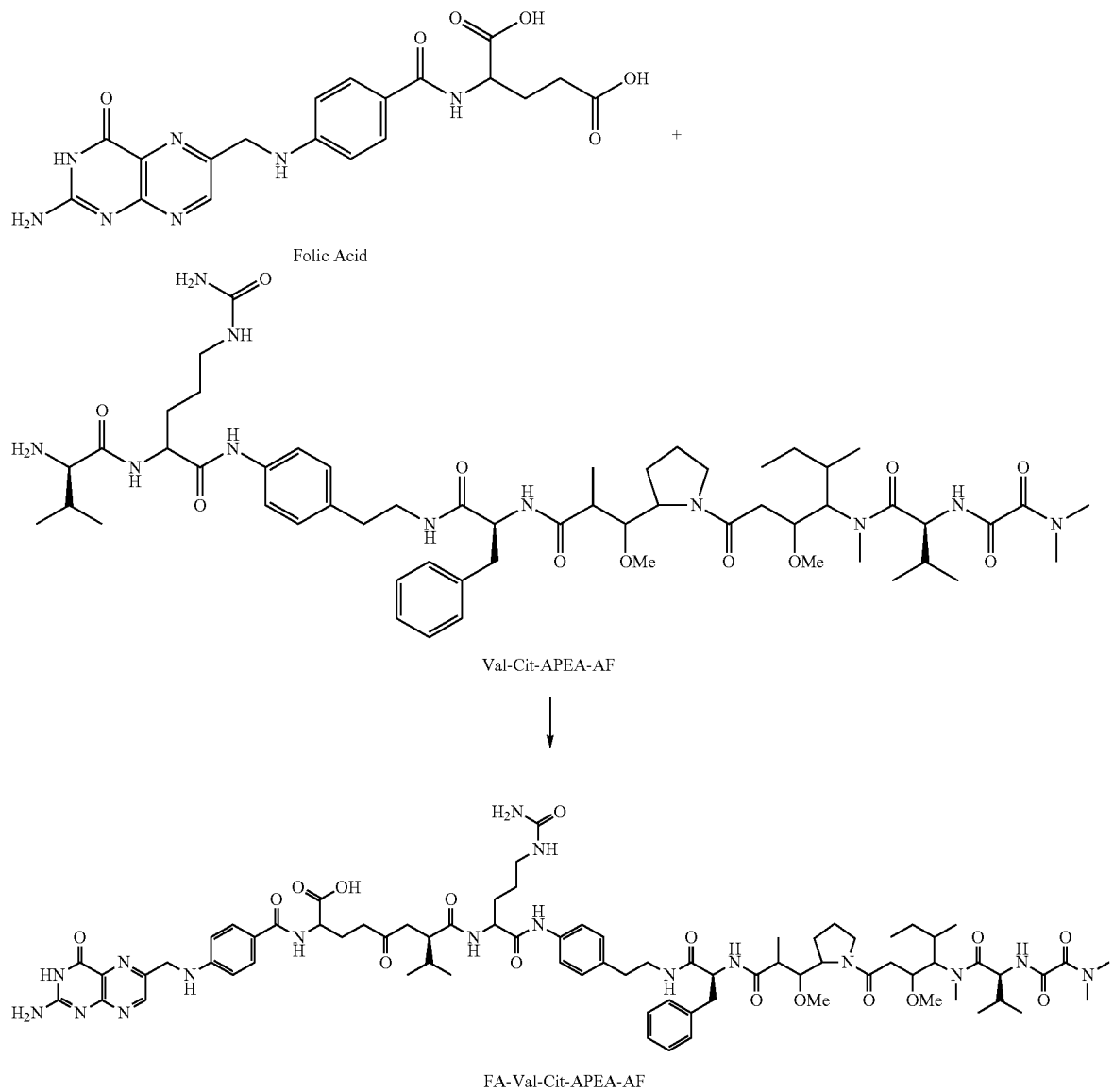

To a solution of folic acid (11.5 mg, 0.026 mmol) in DMF (1.5 ml) was added DIPEA (6.5 mg, 0.050 mmol), Val-Cit-APEA-AF (20.9 mg, 0.018 mmol), NHS (3.0 mg, 0.026 mmol) and EDCI (4.0 mg, 0.026 mmol). The reaction mixture was stirred overnight. After removal of DMF from the reaction mixture, the residue was purified by preparative HPLC (33% acetonitrile in water with 0.1% TFA; UV 210 nm; ODS-3 column 30*250 mm; flow rate 24 mL/min). Certain fractions were concentrated and lyophilized to afford FA-Val-Cit-APEA-AF as yellow solid (11.6 mg, 37.4%). LC-MS: FA-Val-Cit-APEA-AF ($C_{78}H_{114}N_{18}O_{14}$) required [MH$^+$]=1543.9, found [MH$^+$]=1544.8.

Example 31

Synthesis of FA-C-Val-Cit-APEA-AF

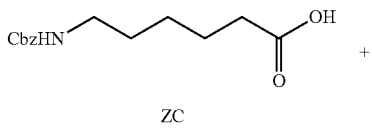

ZC

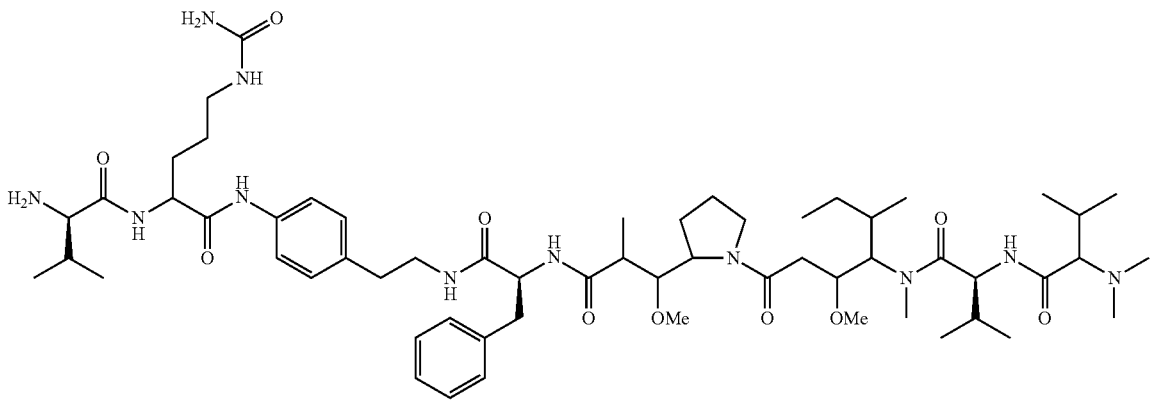

Val-Cit-APEA-AF

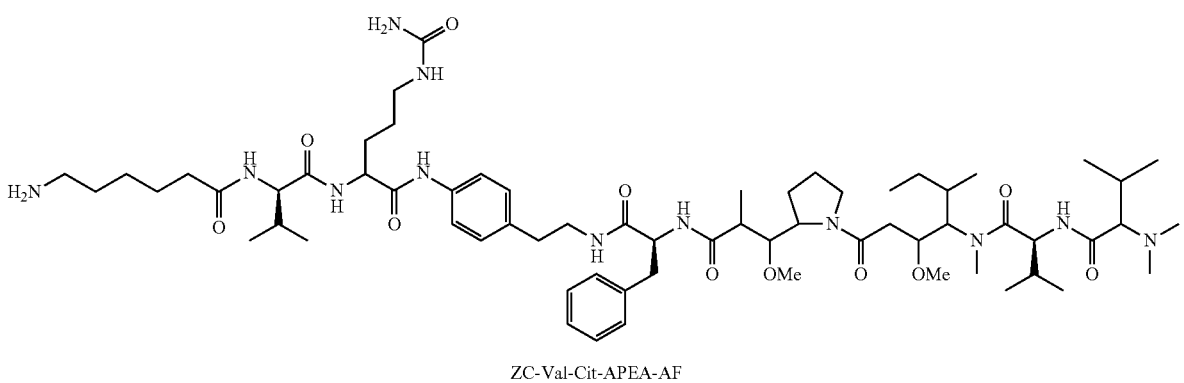

ZC-Val-Cit-APEA-AF

-continued

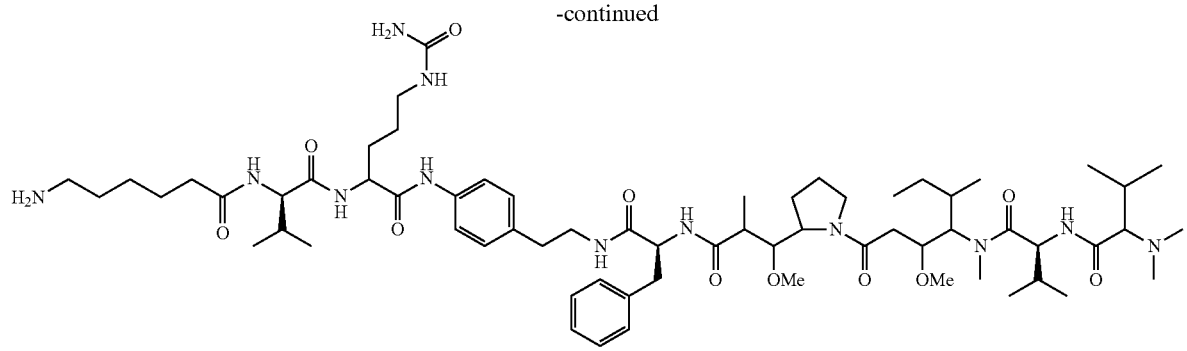

C-Val-Cit-APEA-AF

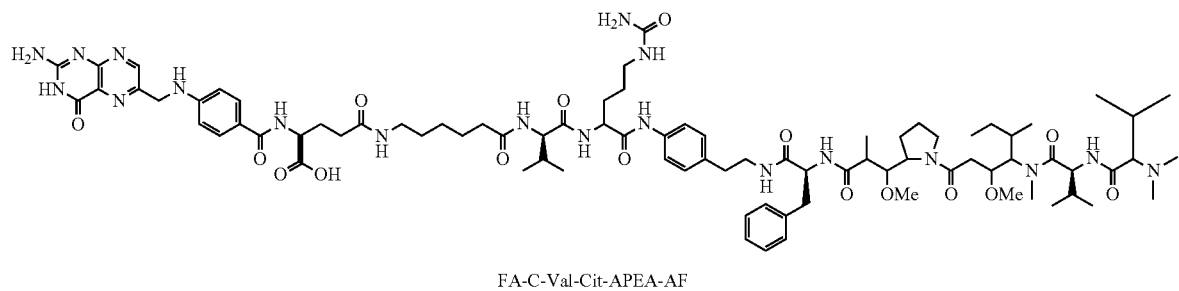 [SMILES: CCC(C)C(C(CC(=O)N1CCCC1C(OC)C(C)C(=O)N[C@@H](Cc1ccccc1)C(=O)NCCc1ccc(NC(=O)C(CCCNC(N)=O)NC(=O)[C@H](NC(=O)CCCCCNC(=O)CC[C@H](NC(=O)c2ccc(NCc3cnc4nc(N)[nH]c(=O)c4n3)cc2)C(=O)O)C(C)C)cc1)OC)N(C)C(=O)[C@@H](NC(=O)C(C(C)C)N(C)C)C(C)C]

FA-C-Val-Cit-APEA-AF

To a solution of Val-Cit-APEA-AF (35.6 mg, 0.029 mmol) in DMF (1 ml) and DCM (3 ml) was added ZC (9.2 mg, 0.037 mmol), HATU (16.0 mg, 0.042 mmol) and DIPEA (9.0 mg, 0.069 mmol). The mixture was stirred at room temperature overnight. The solvents were removed and the residue was purified by preparative HPLC (43% acetonitrile in water with 0.1% TFA; UV 210 nm; ODS-3 column 30*250 mm; flow rate 24 mL/min). Certain fractions were concentrated and lyophilized to afford ZC-Val-Cit-APEA-AF as yellow solid (19.0 mg, 42.9%). LC-MS: ZC-Val-Cit-APEA-AF ($C_{73}H_{114}N_{12}O_{13}$) required [MH$^+$]= 1367.9, found [MH$^+$]=1368.9.

To a solution of ZC-Val-Cit-APEA-AF (19.0 mg, 0.014 mmol) in EtOH (5 mL) was added 5% Pd/C (4.4 mg) and 2M HCl (0.015 mL, 0.030 mmol). Air in the system was replaced by hydrogen gas. The reaction was carried under ambient atmosphere overnight. When ZC-Val-Cit-APEA-AF consumed completely, catalyst was removed from reaction mixture by a filter paper and the filtrate was concentrated on a rotary vapor followed by lyophilization to afford C-Val-Cit-APEA-AF (17.7 mg, 99%).

To a solution of FA (5.0 mg, 0.011 mmol) in DMF (0.75 ml) was added DIPEA (2.7 mg, 0.021 mmol), C-Val-Cit-APEA-AF (9.0 mg, 0.069 mmol), NHS (1.2 mg, 0.010 mmol) and EDCI (1.6 mg, 0.010 mmol). The reaction mixture was stirred overnight. Progress of the reaction was monitored by HPLC. After removal of DMF from the reaction mixture, the residue was purified by preparative HPLC (33% acetonitrile in water with 0.1% TFA; UV 210 nm; ODS-3 column 30*250 mm; flow rate 24 mL/min). Certain fractions were concentrated and lyophilized to afford FA-C-Val-Cit-APEA-AF as yellow solid (4.5 mg, 34.7%). LC-MS: FA-C-Val-Cit-APEA-AF ($C_{84}H_{125}N_{19}O_{16}$) required [MH$^+$]=1657.0, found [MH$^+$]=1657.9.

Example 32

Synthesis of FA-SAA1-Val-Cit-APEA-AF

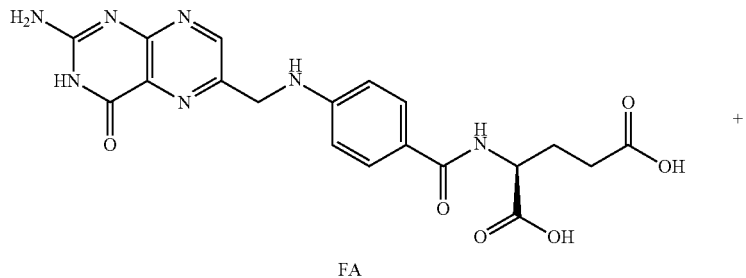

FA

-continued

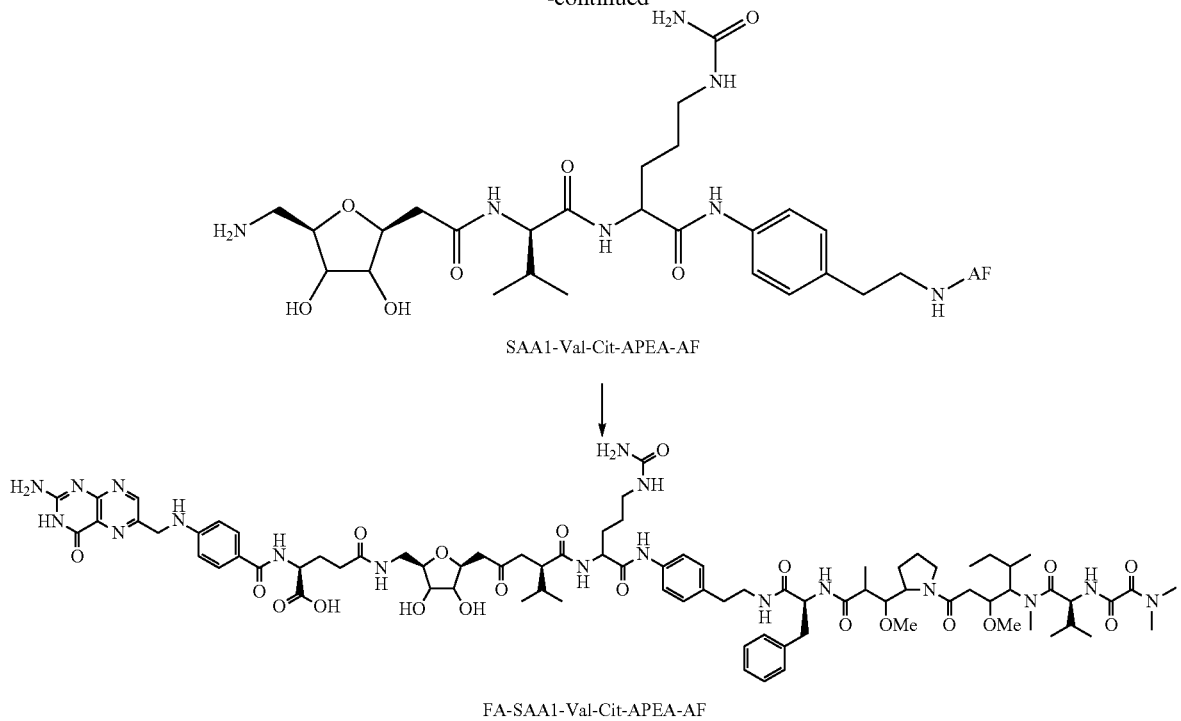

SAA1-Val-Cit-APEA-AF

↓

FA-SAA1-Val-Cit-APEA-AF

To a solution of folic acid (11.2 mg, 0.025 mmol) in DMF (1.5 ml) was added DIPEA (5.8 mg, 0.0 45 mmol), SAA1-Val-Cit-APEA-AF (22.3 mg, 0.018 mmol), NHS (3.0 mg, 0.026 mmol) and EDCI (4.0 mg, 0.026 mmol). The reaction mixture was stirred overnight. Progress of the reaction was monitored by HPLC. After removal of DMF from the reaction mixture, the residue was purified by preparative HPLC (33% acetonitrile in water with 0.1% TFA; UV 210 nm; ODS-3 column 30*250 mm; flow rate 24 mL/min). Certain fractions were concentrated and lyophilized to afford FA-SAA1-Val-Cit-APEA-AF as yellow solid (11.8 mg, 37.4%). LC-MS: FA-SAA1-Val-Cit-APEA-AF ($C_{85}H_{125}N_{19}O_{19}$) required [MH$^+$]=1716.9, found [MH$^+$]=1717.9 (M+H).

Example 33

Synthesis of FA-C-SAA1-Val-Cit-APEA-AF

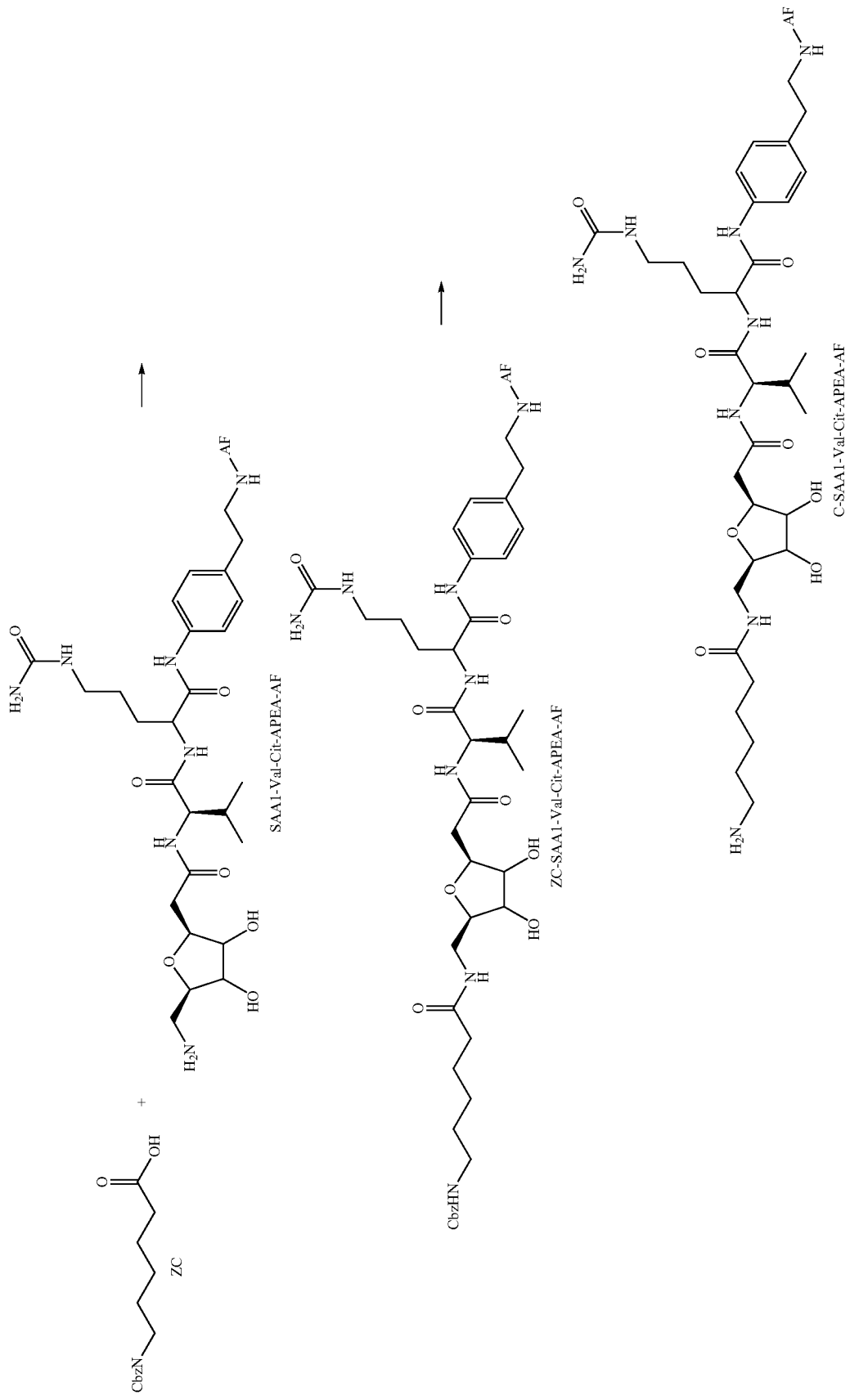

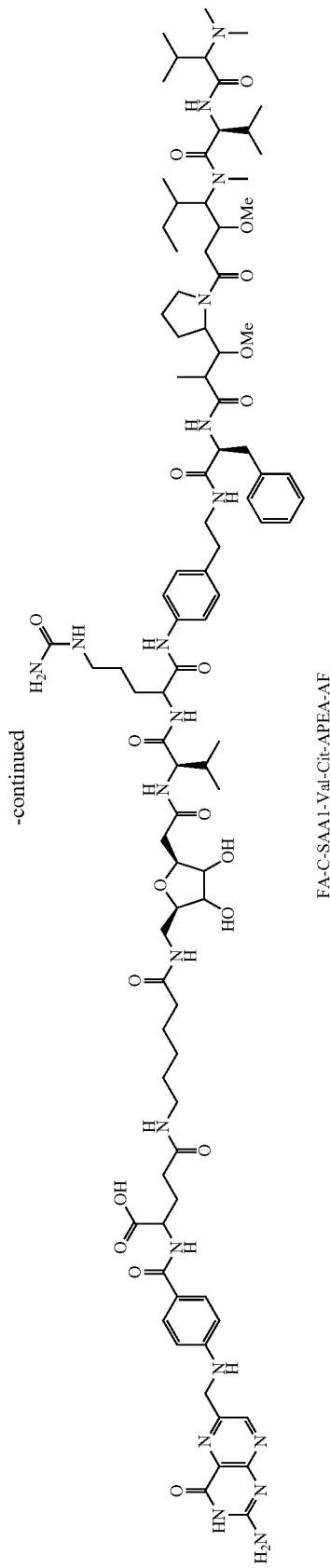
FA-C-SAA1-Val-Cit-APEA-AF

To a solution of SAA1-Val-Cit-APEA-AF (44.0 mg, 0.029 mmol) in DMF (1 ml) and DCM (3 ml) was added ZC (15.0 mg, 0.057 mmol), HATU (16.8 mg, 0.044 mmol) and DIPEA (11.5 mg, 0.089 mmol). The mixture was stirred overnight. Solvents were removed on a rotary vapor and the residue was purified by preparative HPLC (43% acetonitrile in water with 0.1% TFA; UV 210 nm; ODS-3 column 30*250 mm; flow rate 24 mL/min). Fractions were collected, concentrated, and lyophilized to afford ZC-SAA1-Val-Cit-APEA-AF as white solid (30.0 mg, 62.5%). LC-MS: ZC-SAA1-Val-Cit-APEA-AF ($C_{80}H_{125}N_{13}O_{17}$) required [MH$^+$]=1540.9, found [MH$^+$]=1541.8.

To a solution of ZC-SAA1-Val-Cit-APEA-AF (30.0 mg, 0.018 mmol) in EtOH was added 5% Pd/C (5.2 mg) and 2M HCl (0.019 mL, 0.038 mmol). Air in the system was replaced by hydrogen gas. The reaction was carried out under ambient atmosphere overnight. When ZC-SAA1-Val-Cit-APEA-AF consumed completely, catalyst was removed from the reaction mixture by a filter paper and the filtrate was concentrated on a rotary vapor followed by lyophilization to afford C-SAA1-Val-Cit-APEA-AF (24.9 mg, 92.8%). LC-MS: C-SAA1-Val-Cit-APEA-AF ($C72H_{119}N_{13}O_{15}$) required [M+2H]2+=704.0, found [M+2H]2+=705.1.

To a solution of folic acid (4.5 mg, 0.013 mmol) in DMF (0.7 ml) was added DIPEA (2.70 mg, 0.021 mmol), C-SAA1-Val-Cit-APEA-AF (11.0 mg, 0.007 mmol), NHS (1.2 mg, 0.010 mmol) and EDCI (1.6 mg, 0.010 mmol). The reaction mixture was stirred overnight. Progress of the reaction was monitored by HPLC. After removal of DMF from the reaction mixture, the residue was purified by preparative HPLC (31% acetonitrile in water with 0.1% TFA; UV 210 nm; ODS-3 column 30*250 mm; flow rate 24 mL/min). Certain fractions were concentrated and lyophilized to afford FA-C-SAA1-Val-Cit-APEA-AF as yellow solid (3.9 mg, 25.5%). LC-MS: FA-C-SAA1-Val-Cit-APEA-AF ($C_{91}H_{136}N_{20}O_{20}$) required [MH$^+$]=1830.1, found [MH$^+$]=1831.0.

It will be apparent to those skilled in the art that various modifications and variations may be made to the disclosed embodiments. It is intended that the specification and examples be considered as exemplary only, with the true scope of the disclosure being indicated by the following claims and their equivalents.

What is claimed is:

1. A ligand-drug conjugate of formula (VI) or a pharmaceutically acceptable salt thereof:

L-(C-SAAs-AAs-D)p    (VI)

wherein p is an integer ranging from 1 to 20;

L- is a ligand unit selected from the group consisting of full-length antibodies, antibody fragments, proteins, smaller molecular weight proteins, polypeptides, oligopeptides, aptamers, lectins, glycoproteins, lipoproteins, glycolipids, vitamins, nutrient-transport molecules, hormones, monosaccharides, disaccharides, oligosaccharides, polysaccharides and any other cell binding molecules or substance;

C- is a conjugating unit forming selected from the group consisting of

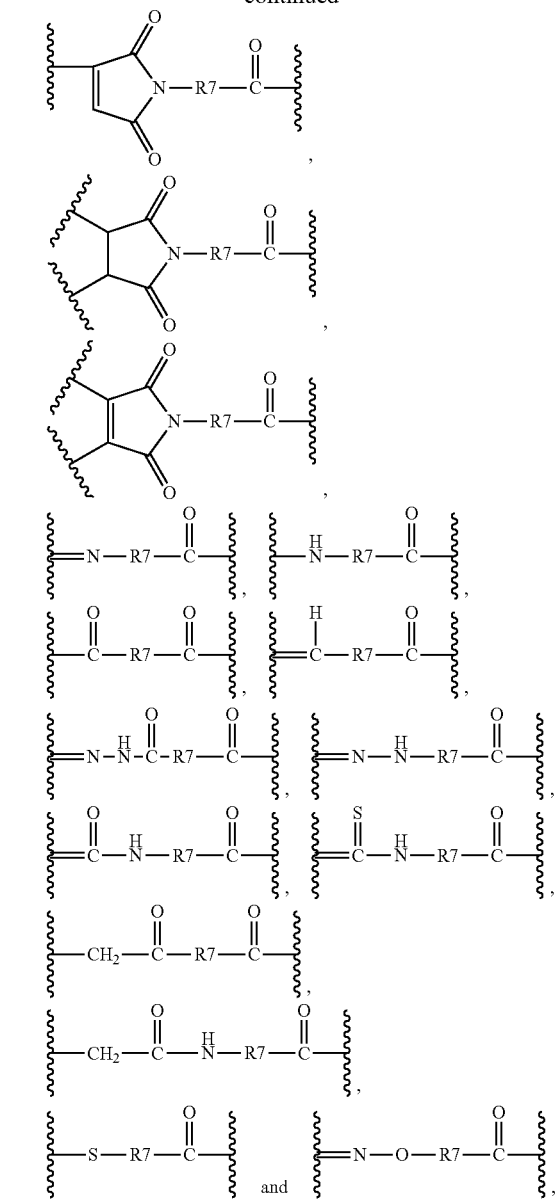

wherein R7 is selected from the group consisting of —C1-C10 alkylene-, —C3-C8 carbocyclo-, —O—(C1-C8 alkyl)-, -arylene-, —C1-C10 alkylene-arylene-, -arylene-C1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, —(C3-C8 heterocyclo-C1-C10 alkylene-, —(CH$_2$CH$_2$O)$_r$— and —(CH$_2$CH$_2$O)$_r$—CH$_2$—, and r is an integer ranging from 1 to 10;

-SAAs- is a sugar amino acid unit of formula (IV):

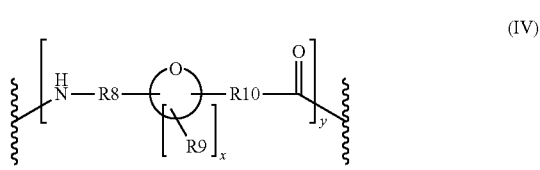

wherein x is an integer ranging from 1 to 8, y is an integer ranging from 1 to 4,

is tetrahydrofuran, dihydrofuran, tetrahydropyran or dihydropyran ring, R8 and R10 are each, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 is, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring;

-AAs- is a peptide unit of formula (V):

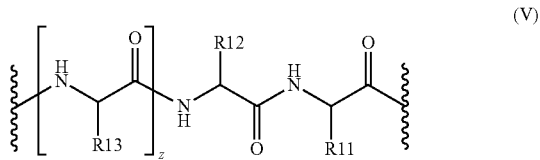

(V)

wherein z is an integer ranging from 0 to 10, R11 is $-(CH_2)_3NHC(=NH)NH_2$, $-(CH_2)_3NH_2$, $-(CH_2)_3NHCONH_2$, $-(CH_2)_4NHC(=NH)NH_2$, $-(CH_2)_4NH_2$ or $-(CH_2)_4NHCONH_2$, R12 is H, methyl, ethyl, propyl, isopropyl, cyclopropyl, butyl, sec-butyl, isobutyl, tert-butyl, cyclobutyl, phenyl or benzyl, R13 is hydrogen, methyl, isopropyl, cyclopropyl, butyl, sec-butyl, isobutyl, tert-butyl, cyclobutyl, cyclohexyl, phenyl, benzyl, p-hydroxybenzyl, $-CH_2OH$, $-CH(OH)CH_3$, $-CH_2CH_2SCH_3$, $-CH_2CONH_2$, $-CH_2COOH$, $-CH_2CH_2CONH_2$, $-CH_2CH_2COOH$, $-(CH_2)_3NHC(=NH)NH_2$, $-(CH_2)_3NH_2$, $-(CH_2)_3NHCOCH_3$, $-(CH_2)_3NHCHO$, $-(CH_2)_4NHC(=NH)NH_2$, $-(CH_2)_4NH_2$, $-(CH_2)_4NHCOCH_3$, $-(CH_2)_4NHCHO$, $-(CH_2)_3NHCONH_2$, $-(CH_2)_4NHCONH_2$, $-CH_2CH(OH)CH_2NH_2$, 2-pyridylmethyl, 3-pyridylmethyl or 4-pyridylmethyl; and -D is a cytotoxic agent selected from the group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

2. The ligand-drug conjugate as claimed in claim 1, wherein the ligand unit is an antibody that binds to an antigen.

3. The ligand-drug conjugate as claimed in claim 2, wherein the antibody is a chimeric antibody, a humanized antibody or a functionally active fragment thereof.

4. The ligand-drug conjugate as claimed in claim 2, wherein the antibody is attached to a conjugating unit through a cysteine residue of the antibody.

5. The ligand-drug conjugate as claimed in claim 1, wherein p is an integer ranging from 2 to 8.

6. The ligand-drug conjugate as claimed in claim 5, wherein p is an integer of 4.

7. The ligand-drug conjugate as claimed in claim 1, wherein the ligand unit is folate, methotrexate or a folate receptor binding ligand that binds to a folate receptor.

8. The ligand-drug conjugate as claimed in claim 1, wherein the ligand unit is a luteinizing hormone-releasing hormone (LHRH), a luteinizing hormone-releasing hormone agonist, a luteinizing hormone-releasing hormone antagonist or a luteinizing hormone-releasing hormone receptor binding ligand that binds to a luteinizing hormone-releasing hormone receptor.

9. The ligand-drug conjugate as claimed in claim 1, wherein C- is the conjugating unit selected from the group consisting of

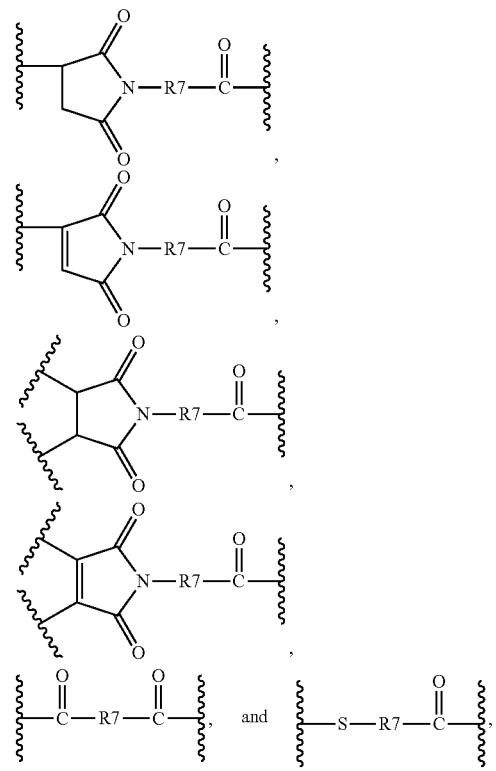

wherein R7 is selected from the group consisting of -1,5-pentylene-, -1,6-hexylene-, -1,4-cyclohexylene-, $-(CH_2CH_2O)_r-CH_2-$ and $-(CH_2CH_2O)_r-CH_2-CH_2-$, and r is an integer ranging from 2-5.

10. The ligand-drug conjugate as claimed in claim 1, wherein -SAAs- is the sugar amino acid unit selected from the group consisting of

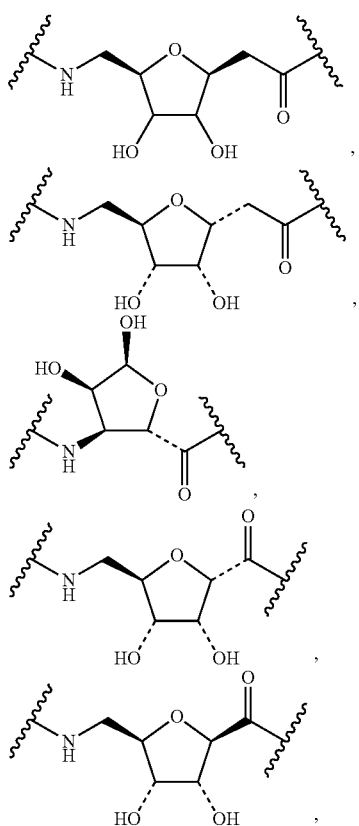
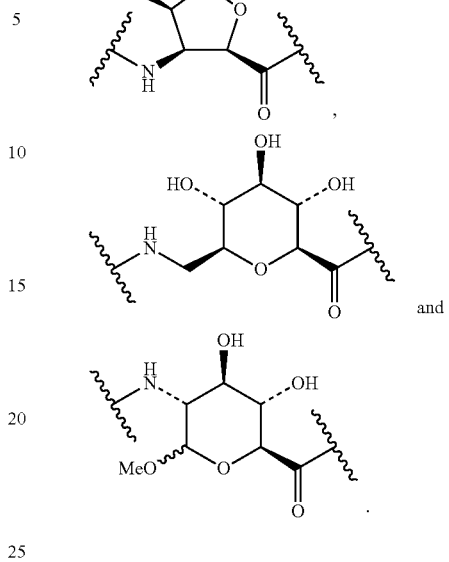
11. The ligand-drug conjugate as claimed in claim 1, wherein -AAs- is the peptide unit selected from the group consisting of -Val-Cit-, -Val-Lys-, -Val-Arg-, -Phe-Cit-, -Phe-Lys- and -Phe-Arg-.
12. The ligand-drug conjugate as claimed in claim 1, wherein -D is the cytotoxic agent selected from the group consisting of
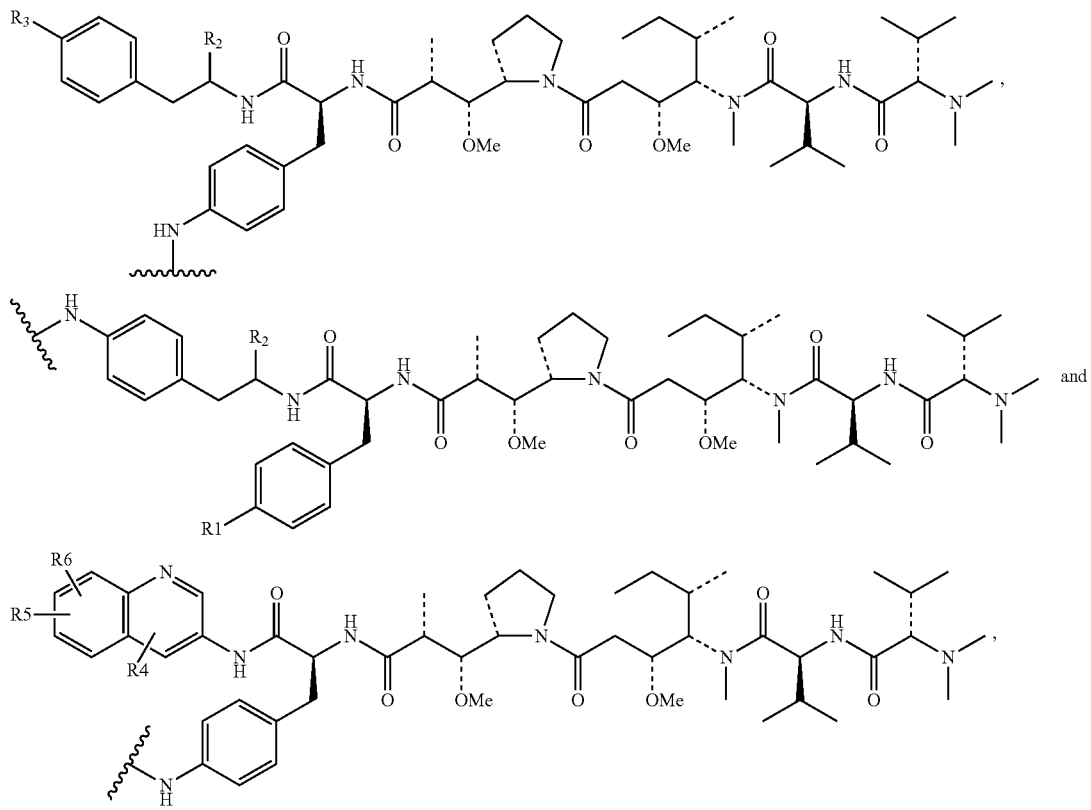

wherein R1, R2, R3, R4, R5 and R6 are each, independently, hydrogen, amino, nitro, halogen, hydroxyl, methoxy, ethoxy, carboxylic acid, methoxycarbonyl, ethoxycarbonyl, methylamino, dimethylamino, ethylamino, diethylamino, 1-pyrrolidinyl, 1-piperidinyl, 1-piperazinyl, aminocarbonyl, methylaminocarbonyl, dimethylaminocarbonyl, ethylaminocarbonyl, diethylaminocarbonyl, 1-pyrrolidinylcarbonyl, 1-piperidinylcarbonyl, 1-piperazinylcarbonyl, methyl, ethyl, propyl, isopropyl or phenyl.

* * * * *